US007728110B2

(12) United States Patent
Babcook et al.

(10) Patent No.: US 7,728,110 B2
(45) Date of Patent: Jun. 1, 2010

(54) ANTIBODIES TO SARS CORONAVIRUS

(75) Inventors: John S. Babcook, Vancouver (CA); Bellur S. Prabhakar, Oakbrook, IL (US); Melissa Coughlin, Chicago, IL (US)

(73) Assignee: Amgen, Inc., Thousand Oaks, CA (US)

( * ) Notice: Subject to any disclaimer, the term of this patent is extended or adjusted under 35 U.S.C. 154(b) by 174 days.

(21) Appl. No.: 11/805,129

(22) Filed: May 21, 2007

(65) Prior Publication Data

US 2008/0248043 A1 Oct. 9, 2008

Related U.S. Application Data

(60) Provisional application No. 60/801,951, filed on May 19, 2006.

(51) Int. Cl.
C12P 21/08 (2006.01)
C07K 16/00 (2006.01)
(52) U.S. Cl. ............... 530/387.3; 530/388.8; 530/388.3
(58) Field of Classification Search ...................... None
See application file for complete search history.

(56) References Cited

U.S. PATENT DOCUMENTS

| 5,849,992 | A | 12/1998 | Meade et al. | |
|---|---|---|---|---|
| 5,959,177 | A | 9/1999 | Hein et al. | |
| 2005/0069869 | A1* | 3/2005 | Ambrosino et al. | 435/5 |
| 2005/0249739 | A1* | 11/2005 | Marasco et al. | 424/159.1 |

FOREIGN PATENT DOCUMENTS

| WO | WO2005/018538 | 3/2005 |
|---|---|---|
| WO | WO/2005/054469 | 6/2005 |
| WO | WO2005/056585 | 6/2005 |
| WO | WO2005/060520 | 7/2005 |
| WO | WO2006/051091 | 5/2006 |

OTHER PUBLICATIONS

Nara PL, Lin G."HIV-1: the confounding variables of virus neutralization."Curr Drug Targets Infect Disord. Jun. 2005;5(2):157-70.*
Green LL. "Antibody engineering via genetic engineering of the mouse: XenoMouse strains are a vehicle for the facile generation of therapeutic human monoclonal antibodies." J Immunol Methods. Dec. 10, 1999;231(1-2):11-23.*
Kashmiri SV, et al. "SDR grafting-a new approach to antibody humanization" Methods. May 2005;36(1):25-34.*
Rudikoff S, "Single amino acid substitution altering antigen-binding specificity." Proc Natl Acad Sci U S A. Mar. 1982;79(6):1979-83.*
Ko and Koprowski, Plant biopharming of monoclonal antibodies, Virus Res. 111:93-100 (2005).
Lai et al., Characterization of neutralizing monoclonal; antibodies recognizing a 15-residues epitope on the spike protein HR2 region of severe acute respiratory syndrome coronavirus (SARS-CoV), J. Biol. Sci. 12:711-727 (2005).
Qiu et al., Antibody responses to individual proteins of SARS coronavirus and their neutralization activities, Microbes and Inf. 7:882-889 (2005).
Sola et al., Transgenic mice secreting coronavirus neutralizing antibodies into the milk, J. Virol. 3762-3772 (1998).
Ter Meulen et al., Human monoclonal antibody as prophylaxis for SARA coronavirus infection in ferrets, The Lancet 363:2139-2141 (2004).
Tripp et al., Monoclonal antibodies to SARS-associated coronavirus (SARS-CoV): Identification of neutralizing and antibodies reactive to S, N, M and E viral proteins, J. Virol. Meth. 128:21-28 (2005).
Zhang et al., Human monoclonal antibodies to the S glycoprotein and related proteins as potential therapeutics for SARS, Curr. Op. Mol. Ther. 7(2):151-156.
Babcook et al., 1996, A novel strategy for generating monoclonal antibodies from single, isolated lymphocytes producing antibodies of defined specificities, Proc. Natl. Acad. Sci. USA 93:7843-7848.
Baker, 2004, Coronaviruses: from common colds to severe acute respiratory syndrome, Pediatr. Infect. Dis. J. 23:1049-1050.
Berry et al., 2004, Development and characterisation of neutralising monoclonal antibody to the SARS-coronavirus, J. Virol. Meth. 120:87-96.
Bisht et al., 2004, Severe acute respiratory syndrome coronavirus spike protein expressed by attenuated vaccinia virus protectively immunizes mice, Proc. Natl. Acad. Sci. USA 101:6641-6646.
Buchholz et al., 2004, Contributions of the structural proteins of severe acute respiratory syndrome coronavirus to protective immunity, Proc. Natl. Acad. Sci. USA 101:9804-9809.
Chan et al., 2006, SARS: clinical presentation, transmission, pathogenesis and treatment options, Clin. Sci. 110:193-204.
Cheng et al., 2005, Use of convalescent plasma therapy in SARS patients in Hong Kong, Eur. J. Clin. Microbiol. 24:44-46.
Coughlin et al., 2007, Generation and characterization of human monoclonal neutralizing antibodies with distinct binding and sequence features against SARS coronavirus using XenoMouse, Virol. 361(1):93-102.
Davis et al., 2004, Production of human antibodies from transgenic mice, Meth. Mol. Biol. 248:191-200.

(Continued)

Primary Examiner—Bo Peng
(74) Attorney, Agent, or Firm—Ropes & Gray LLP; Jane T. Gunnison; Ryan D. Murphey

(57) ABSTRACT

The present invention relates to antibodies including human antibodies and antigen-binding portions thereof that specifically bind to human SARS-CoV S protein, and that function to neutralize SARS-CoV. The invention also relates to antibodies that are bispecific, derivatized, single chain antibodies or portions of fusion proteins. The invention also relates to isolated heavy and light chain immunoglobulins derived from human anti-SARS-CoV S protein antibodies and nucleic acid molecules encoding such immunoglobulins. The present invention also relates to methods of using the antibodies and compositions for diagnosis and treatment. The invention also provides gene therapy methods using nucleic acid molecules encoding the heavy and/or light immunoglobulin molecules that comprise the human anti-SARS-CoV S protein antibodies. The invention also relates to transgenic animals or plants comprising nucleic acid molecules of the present invention.

15 Claims, 10 Drawing Sheets

OTHER PUBLICATIONS

Gallo et al., 2000, The human immunoglobulin loci introduced into mice: V(D) and J gene segment usage similar to that of adult humans, Eur. J. Immunol. 30:534-540.

Greenough et al., 2005, Development and characterization of a severe acute respiratory syndrome-associated coronavirus-neutralizing human monoclonal antibody that provides effective immunoprophylaxis in mice, J. Infect. Dis. 191:507-514.

Griffiths et al., Human anti-self antibodies with high specificity from phage display libraries, EMBO J. 12:725-734.

Griffiths et al., 1994, Isolation of high affinity human antibodies directly from large synthetic repertoires EMBO J. 13:3245-3260.

Hanauer and Present, 2003, The state of the art in the management of inflammatory bowel disease, Rev. Gastroenterol. Disord. 3:81-92.

He et al., 2004, Receptor-binding domain of SARS-CoV spike protein induces highly potent neutralizing antibodies: implication for developing subunit vaccine, Biochem. Biophys. Res. Commun. 324:773-781.

He et al., 2005, Receptor-binding domain of severe acute respiratory syndrome coronavirus spike protein contains multiple conformation-dependent epitopes that induce highly potent neutralizing antibodies, J. Immunol. 174:4908-4915.

He et al., 2005, Identification of a critical neutralization determinant of severe acute respiratory syndrome (SARS)-associated coronavirus: importance for designing SARS vaccines, Virology 334:74-82.

Hofmann et al., 2004, S protein of severe acute respiratory syndrome-associated coronavirus mediates entry into hepatoma cell lines and is targeted by neutralizing antibodies in infected patients, J. Virol. 78:6134-6142.

Huang et al., 2002, Fully humanized neutralizing antibodies to interleukin-8 (ABX-IL8) inhibit angiogenesis, tumor growth, and metastasis of human melanoma, Am. J. Pathol. 161:125-134.

Li et al., 2003, Angiotensin-converting enzyme 2 is a functional receptor for the SARS coronavirus, Nature 426:450-454.

Li et al., 2005, Structure of SARS coronavirus spike receptor-binding domain complexed with receptor, Science 309:1864-1868.

Li et al., 2005, Bats are natural reservoirs of SARS-like coronaviruses, Science 310:676-679.

Lonberg, 2005, Human antibodies from transgenic animals, Nat. Biotech. 23:1117-1125.

Marks et al., 1991, Eur. J. Immunol. 21:980-991.

Nissim et al., 1994, Antibody fragments from a 'single pot' phage display library as immunochemical reagents, 13(3):692-698.

Piedimonte et al., 2000, A humanized monoclonal antibody against respiratory syncytial virus (palivizumab) inhibits RSV-induced neurogenic-mediated inflammation in rat airways, Pediatr. Res. 47:351-356.

Rathanaswami et al., 2005, Demonstration of an in vivo generated sub-picomolar affinity fully human monoclonal antibody to interleukin-8, Biochem. Biophys. Res. Commun. 334:1004-1013.

Ross et al., 2003, The Her-2/neu gene and protein in breast cancer 2003: biomarker and target of therapy, Oncologist 8:307-325.

Subbarao et al., 2004, Prior infection and passive transfer of neutralizing antibody prevent replication of severe acute respiratory syndrome coronavirus in the respiratory tract of mice, J. Virol. 78:3572-3577.

Sui et al., 2005, Evaluation of human monoclonal antibody 80R for immunoprophylaxis of severe acute respiratory syndrome by an animal study, epitope mapping, and analysis of spike variants, J. Virol. 79:5900-5906.

Sui, 2004, Potent neutralization of severe acute respiratory syndrome (SARS) coronavirus by a human mAb to S1 protein that blocks receptor association, Proc. Natl. Acad. Sci. USA 101(8):2536-2541.

Ter Meulen et al., 2006, Human monoclonal antibody combination against SARS coronavirus: synergy and coverage of escape mutants, PLoS Med. 3(7):1071-1079.

The Chinese SARS Molecular Epidemiology Consortium, 2004, Molecular evolution of the SARS coronavirus during the course of the SARS epidemic in China, Science 303:1666-1669.

Traggiai et al., 2004, An efficient method to make human monoclonal antibodies from memory B cells: potent neutralization of SARS coronavirus, Nat. Med. 10:871-875.

Van Den Brink et al., 2005, Molecular and biological characterization of human monoclonal antibodies binding to the spike and nucleocapsid proteins of severe acute respiratory syndrome coronavirus, J. Virol. 79(3):1635-1644.

Wong et al., 2004, A 193-amino acid fragment of the SARS coronavirus S protein efficiently binds angiotensin-converting enzyme 2, J. Biol. Chem. 279:3197-3201.

Yang et al., 2004, A DNA vaccine induces SARS coronavirus neutralization and protective immunity in mice, Nature 428:561-564.

Yang et al., 2005, Evasion of antibody neutralization in emerging severe acute respiratory syndrome coronaviruses, Proc. Natl. Acad. Sci. USA 102:797-801.

Yi et al., 2005, Single amino acid substitutions in the severe acute respiratory syndrome coronavirus spike glycoprotein determine viral entry and immunogenicity of a major neutralizing domain, J. Virol. 79:11638-11646.

Zhang et al., 2004, Identification of an antigenic determinant on the S2 domain of the severe acute respiratory syndrome coronavirus spike glycoprotein capable of inducing neutralizing antibodies, J, Virol. 78:6938-6945.

* cited by examiner

Figure 4

| SEQ ID NOS | H Chain | CDR1 | CDR2 | CDR3 |
|---|---|---|---|---|
| | VH1-18, D1-26, JH4B | | | |
| 99 | Germline | GYTFTSYGIS | WISAYNGNTNYAQKLQG | GRYLDY |
| 99 | 5D6 | ---------- | ----------------- | ----- |
| 99 | 5D3 | ---------- | ----------------- | ----- |
| 99 | 6B8 | ---------- | ----------------- | ----- |
| 99 | 3A7 | ---------- | ----------------- | ----- |
| 99 | 5A7 | ---------- | ----------------- | ----- |
| | VH1-2, N/A, JH4B | | | |
| 100 | Germline | GYTFTGYYMH | WINPNSGGTNYAQKFQG | GTYLDY |
| 101 | 5E4 | -----V--- | ----------------- | -R--- |
| | VH1-2, D3-10, JH4B | | | |
| 102 | Germline | GYTFTGYYMH | WINPNSGGTNYAQKFQG | GPHTFGSGSYPFDY |
| 102 | 3F3 | -FP--D--- | ---S------------- | -------------- |
| 102 | 6C2 | -FP--D--- | ---S------------- | -------------- |
| 103 | 6C1 | ---------- | ---S------------- | ---S---------- |
| 103 | 4G2 | ---------- | ---S------------- | ---S---------- |
| 104 | 4E2 | ---------- | ---------------- | ---S---------- |
| 102 | 5A5 | ---------- | ---------------- | -------------- |
| 102 | 4A10 | ---------- | ---------------- | -------------- |
| 102 | 6B5 | ---------- | ---------------- | -------------- |
| | VH3-33, N/A, JH5B | | | |
| 105 | Germline | GFTFSSYGMH | VIWYDGSNKYYADSVKG | GDFYWFDP |
| 105 | IB5 | ---------- | ----------------- | -------- |
| | VH3-33, D2-2, JH4B | | | |
| 106 | Germline | GFTFSSYGMH | VIWYDGSNKYYADSVKG | DPLGYCSSTSCSYFDY |
| 107 | 6B1 | ---------- | ---------FH------ | ---------------- |
| 108 | 3C7 | ---------- | -------F--------- | ---------------- |
| | VH4-33, D4-17, JH4B | | | |
| 109 | Germline | GFTFSSYGMH | VIWYDGSNKYYADSVKG | GGDGERFDY |
| 109 | 4D4 | ---------- | ----------------- | --------- |
| | VH4-59, D3-9, JH6B | | | |
| 110 | Germline | GGSISSYYWS | YIYYSGSTNYNPSLKS | DYDILTGYSNYYGMDV |
| 111 | 3H12 | D----F--- | ---------------- | ---------------- |

| SEQ ID NOS | L Chain | CDR1 | CDR2 | CDR3 |
|---|---|---|---|---|
| | A1, JK2 | | | |
| 112 | Germline | RSSQSLVYSDGNTYLN | KVSNWDS | MQGTHWPPYVQ |
| 113 | 4D4 | ------R-------- | ------- | ----------- |
| | A30, JK3 | | | |
| 114 | Germline | RASQGIRNDLG | AASSLQS | LQHNSYPFT |
| 114 | 3H12 | ----------- | ------- | --------- |
| | A30, JK4 | | | |
| 115 | Germline | RASQGIRNDLG | AASSLQS | LQHNSYPLT |
| 116 | 5D6 | ---D------- | ------- | --Y------ |
| 116 | 5D3 | ---D------- | ------- | --Y------ |
| 116 | 6B8 | ---D------- | ------- | --Y------ |
| 116 | 3A7 | ---D------- | ------- | --Y------ |
| 116 | 5A7 | ---D------- | ------- | --Y------ |
| 117 | 4A10 | -------S--- | ------- | Q-Y------ |
| 117 | 5A5 | -------S--- | ------- | Q-Y------ |
| 117 | 3F3 | -------S--- | ------- | Q-Y------ |
| 117 | 6C2 | -------S--- | ------- | Q-Y------ |
| 117 | 1B5 | -------S--- | ------- | Q-Y------ |
| 117 | 6C1 | -------S--- | ------- | Q-Y------ |
| 117 | 4G2 | -------S--- | ------- | Q-Y------ |
| 117 | 6B5 | -------S--- | ------- | Q-Y------ |
| 117 | 4E2 | -------S--- | ------- | Q-Y------ |
| | A30, JK5 | | | |
| 118 | Germline | RASQGIRNDLG | AASSLQS | LQHNSYPIT |
| 119 | 5E4 | ----------- | ------- | --Y------ |
| | L5, JK4 | | | |
| 120 | Germline | RASQGISSWLA | AASSLQS | QQANSF##T |
| 121 | 6B1 | ---------N- | ------- | ----N-PL- |
| 121 | 3C7 | ---------N- | ------- | ----N-PL- |

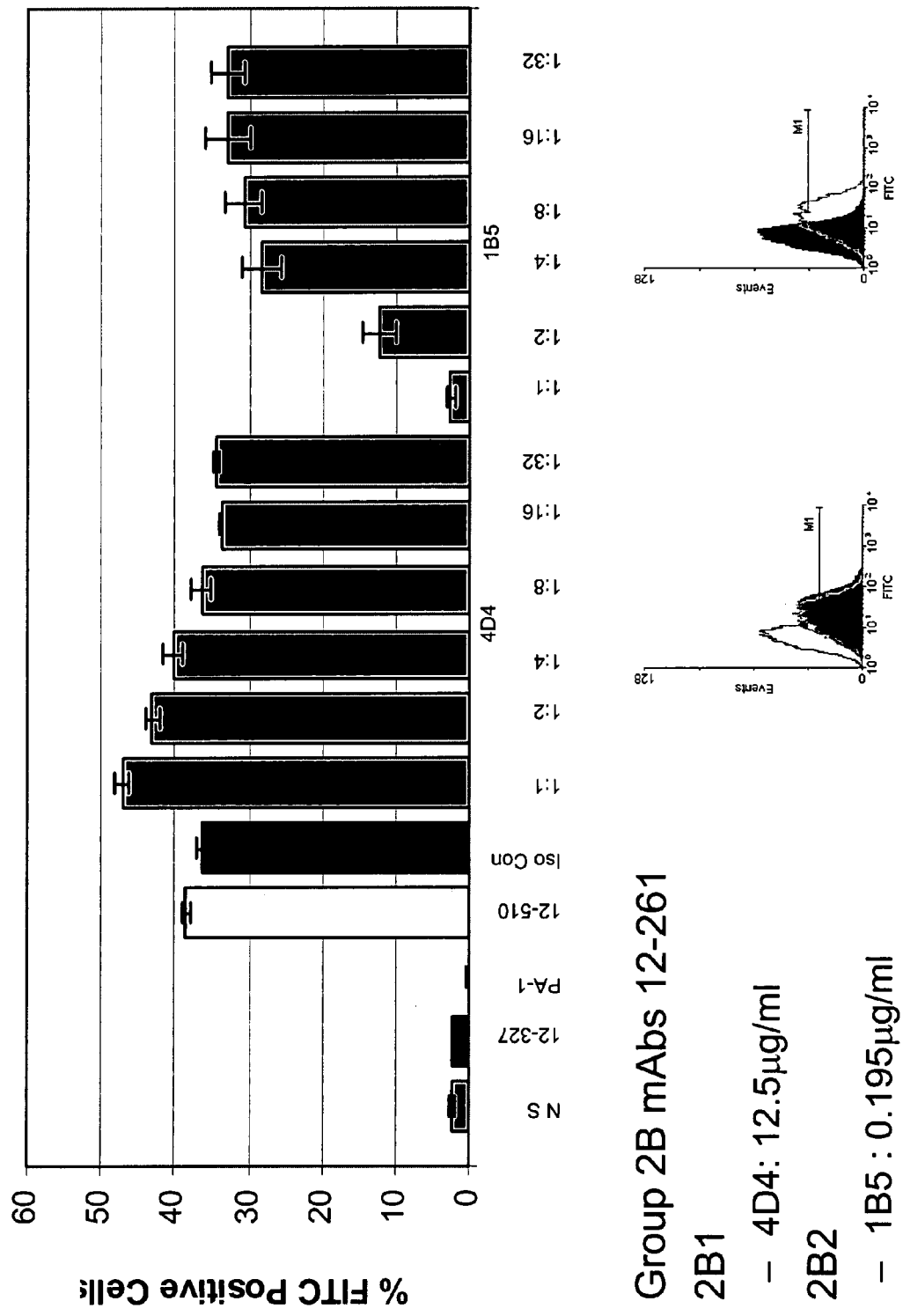

SEQUENCE LISTING

<160> NUMBER OF SEQ ID NOS: 134

<210> SEQ ID NO 1
<211> LENGTH: 345
<212> TYPE: DNA
<213> ORGANISM: Homo sapiens

<400> SEQUENCE: 1
caggttcagc tggtgcagtc tggagctgag gtgaagaagc ctggggcctc agtgaaggtc 60

```
tcctgcaagg cttctggtta caccttacc agctatggta tcagctgggt gcgacaggcc    120
cctggacaag ggcttgagtg gatgggatgg atcagcgctt ataatggtaa cacaaactat    180
gcacagaagc tccagggcag agtcaccatg accacagaca catccactaa cacagcctac    240
atggagctga ggagcctgag atctgacgac acggccgtgt attactgtgc ggttgggagg    300
taccttgact actggggcca gggaaccctg gtcaccgtct cctca                   345

<210> SEQ ID NO 2
<211> LENGTH: 115
<212> TYPE: PRT
<213> ORGANISM: Homo sapiens

<400> SEQUENCE: 2

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Trp Ile Ser Ala Tyr Asn Gly Asn Thr Asn Tyr Ala Gln Lys Leu
         50                  55                  60

Gln Gly Arg Val Thr Met Thr Thr Asp Thr Ser Thr Asn Thr Ala Tyr
 65                  70                  75                  80

Met Glu Leu Arg Ser Leu Arg Ser Asp Asp Thr Ala Val Tyr Tyr Cys
                 85                  90                  95

Ala Val Gly Arg Tyr Leu Asp Tyr Trp Gly Gln Gly Thr Leu Val Thr
                100                 105                 110

Val Ser Ser
        115

<210> SEQ ID NO 3
<211> LENGTH: 321
<212> TYPE: DNA
<213> ORGANISM: Homo sapiens

<400> SEQUENCE: 3
gacatccaga tgacccagtc tccatcctcc ctgtctgcat ctgtaggaga cagagtcacc    60
atcacttgcc gggcaagtca ggacattaga aatgatttag ctggtatca gcagaaacca    120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caactattta ctgtctacag tataatagtt accctctcac tttcggcgga    300
gggaccaagg tggagatcaa a                                              321

<210> SEQ ID NO 4
<211> LENGTH: 107
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Arg Asn Asp
                 20                  25                  30

Leu Gly Trp Tyr Gln Gln Lys Pro Gly Lys Ala Pro Lys Arg Leu Ile
             35                  40                  45
```

Tyr Ala Ala Ser Ser Leu Gln Ser Gly Val Pro Ser Arg Phe Ser Gly
                50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Asn Ser Tyr Pro Leu
                 85                  90                  95

Thr Phe Gly Gly Gly Thr Lys Val Glu Ile Lys
            100                 105

<210> SEQ ID NO 5
<211> LENGTH: 345
<212> TYPE: DNA
<213> ORGANISM: Homo sapiens

<400> SEQUENCE: 5
caggttcagc tggtgcagtc tggagctgag gtgaagaagc ctggggcctc agtgaaggtc        60
tcctgcaagg cttctggtta cacctttacc agctatggta tcagctgggt gcgacaggcc       120
cctggacaag gtcttgagtg gatgggatgg atcagcgcat ataatggtaa cacaaactat       180
gcacagaagc tccagggcag agtcaccatg accacagaca catccacgag cacagcctac       240
atggagctga ggagcctgag atctgacgac acggccgtgt attactgtgc ggttgggagg       300
taccttgact actggggcca gggaaccctg gtcaccgtct cctca                      345

<210> SEQ ID NO 6
<211> LENGTH: 115
<212> TYPE: PRT
<213> ORGANISM: Homo sapiens

<400> SEQUENCE: 6

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
         50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Val Gly Arg Tyr Leu Asp Tyr Trp Gly Gln Gly Thr Leu Val Thr
            100                 105                 110

Val Ser Ser
        115

<210> SEQ ID NO 7
<211> LENGTH: 321
<212> TYPE: DNA
<213> ORGANISM: Homo sapiens

<400> SEQUENCE: 7
gacatccaga tgacccagtc tccatcctcc ctgtctgcat ctgtaggaga cagagtcacc        60
atcacttgcc gggcaagtca ggacattaga aatgatttag ctggtatca gcagaaacca       120 gggaaagccc ctaagcgcct gatctatgct gcatccagtt tgcaaagtgg ggtcccatca       180

-continued

```
aggttcagcg gcagtggatc tgggacagaa ttcactctca caatcagcag cctgcagcct    240
gaagattttg caacttatta ctgtctacag tataatagtt accctctcac tttcggcgga    300
gggaccaagg tggagatcaa a                                              321
```

<210> SEQ ID NO 8
<211> LENGTH: 107
<212> TYPE: PRT
<213> ORGANISM: Homo sapiens

<400> SEQUENCE: 8

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Leu
                85                  90                  95

Thr Phe Gly Gly Gly Thr Lys Val Glu Ile Lys
            100                 105
```

<210> SEQ ID NO 9
<211> LENGTH: 345
<212> TYPE: DNA
<213> ORGANISM: Homo sapiens

<400> SEQUENCE: 9

```
caggtacacc tggtgcagtc tggggctgag gtgaagaagc ctggggcctc agtgaaggtc    60
tcctgcaagg cttctggata caccttcacc ggctactatg tacactgggt gcgacaggcc    120
cctggacagg gcttgagtg gatgggatgg atcaaccctaa acagtggtgg cacaaactat    180
gcacagaagt tcagggcag ggtcaccatg accagggaca cgtccatcag cacagcctac    240
atggagctga gcaggctgag atctgacgac acggccgtgt attctgtgc gggtgggcgc    300 tacttggact actggggcca gggaaccctg gtcaccgtct cctca                   345
```

<210> SEQ ID NO 10
<211> LENGTH: 115
<212> TYPE: PRT
<213> ORGANISM: Homo sapiens

<400> SEQUENCE: 10

```
Gln Val His Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Val His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Phe Cys
```

```
            85                  90                  95
Ala Gly Gly Arg Tyr Leu Asp Tyr Trp Gly Gln Gly Thr Leu Val Thr
            100                 105                 110

Val Ser Ser
        115

<210> SEQ ID NO 11
<211> LENGTH: 321
<212> TYPE: DNA
<213> ORGANISM: Homo sapiens

<400> SEQUENCE: 11
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct gatctatgct gcatccagtt tgcaaagtgg ggtcccatca    180
aggttcagcg gcagcggatc tgggacagaa ttcactctca caatcagcag cctgcagcct    240
gaagattttg caacttatta ctgtctacag tataatagtt acccgatcac cttcggccaa    300
gggacacgac tggagattaa a                                              321

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Ile
                85                  90                  95

Thr Phe Gly Gln Gly Thr Arg Leu Glu Ile Lys
            100                 105

<210> SEQ ID NO 13
<211> LENGTH: 345
<212> TYPE: DNA
<213> ORGANISM: Homo sapiens

<400> SEQUENCE: 13
caggtgcagc tggtgcagtc tggggctgag gtgaagaagc ctggggcctc agtgaaggtc      60
tcctgcaagg cttctggata caccttcacc ggctactata tgcactgggt gcgacaggcc    120
cctggacaag gcttgagtg gatgggatgg atcaaccta acagtggtgg cacaaactat      180
gcacagaagt tcagggcag ggtcaccatg accaggaca cgtccatcag cacagcctac     240
atggagctga gcaggctgag atctgacgac acggccgtgt tttactgtgc gggtgggacc    300
tacttggact actgggggcca gggaaccctg gtcaccgtct cctca                    345

<210> SEQ ID NO 14
```

```
<211> LENGTH: 115
<212> TYPE: PRT
<213> ORGANISM: Homo sapiens

<400> SEQUENCE: 14

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Phe Tyr Cys
                 85                  90                  95

Ala Gly Gly Thr Tyr Leu Asp Tyr Trp Gly Gln Gly Thr Leu Val Thr
            100                 105                 110

Val Ser Ser
        115

<210> SEQ ID NO 15
<211> LENGTH: 321
<212> TYPE: DNA
<213> ORGANISM: Homo sapiens

<400> SEQUENCE: 15
gacatccaga tgacccagtc tccatcctcc ctgtctgcat ctgtaggaga cagagtcacc      60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag tataatagtt acccgatcac cttcggccaa    300
gggacacgac tggagattaa a                                              321

<210> SEQ ID NO 16
<211> LENGTH: 107
<212> TYPE: PRT
<213> ORGANISM: Homo sapiens

<400> SEQUENCE: 16

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Asn Ser Tyr Pro Ile
                 85                  90                  95

Thr Phe Gly Gln Gly Thr Arg Leu Glu Ile Lys
            100                 105
```

<210> SEQ ID NO 17
<211> LENGTH: 345
<212> TYPE: DNA
<213> ORGANISM: Homo sapiens

<400> SEQUENCE: 17
caggtgcagc tggtgcagtc tggggctgag gtgaagaagc ctggggcctc agtgaaggtc     60
tcctgcaagg cttctggata caccttcacc ggctactata tgcactgggt gcgacaggcc    120
cctggacaag gcttgagtg gatgggatgg atcaaccctaacagtggtgg cacaaactat    180 gcacagaagt tcagggcag gtcaccatg accaggaca cgtccatcag cacagcctac    240
atggagctga gcaggctgag atctgacgac acggccgtgt tttactgtgc gggtgggacc    300
tacttggact actggggcca gggaaccctg gtcaccgtct cctca                    345

<210> SEQ ID NO 18
<211> LENGTH: 115
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Phe Tyr Cys
                85                  90                  95

Ala Gly Gly Thr Tyr Leu Asp Tyr Trp Gly Gln Gly Thr Leu Val Thr
            100                 105                 110

Val Ser Ser
        115

<210> SEQ ID NO 19
<211> LENGTH: 339
<212> TYPE: DNA
<213> ORGANISM: Homo sapiens

<400> SEQUENCE: 19
gacatcgtga tgacccagtc tccagactcc ctggctgtgt ctctgggcga gagggccacc     60
atcaactgca gtccagcca gagtgtttta tacagctcca acaataagaa ctacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
cctcggacgt tcggccaagg gaccaaggtg gaaatcaaa                           339

<210> SEQ ID NO 20
<211> LENGTH: 113
<212> TYPE: PRT
<213> ORGANISM: Homo sapiens

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys

<210> SEQ ID NO 21
<211> LENGTH: 369
<212> TYPE: DNA
<213> ORGANISM: Homo sapiens

<400> SEQUENCE: 21
caggtgcaac tggtgcagtc tggggctgag gtgaagaagc ctggggcctc agtgaaggtc      60
tcctgcaagg cttctggata caccttcacc ggctactata tgcactgggt gcgacaggcc     120
cctggacaag ggcttgagtg gatgggatgg atcaaccta acagtggtgg cacaaactat     180
gcacagaagt tcagggcag ggtcaccatg accagggaca cgtccatcag ctcggcctac     240
atggaactga gcagcctgag atctgacgac acggccgttt attactgtgc gagagggccc     300
cataccttcg gttcggggag ttacccctt gactactggg gccagggaac cctggtcacc     360
gtctcctca                                                             369

<210> SEQ ID NO 22
<211> LENGTH: 123
<212> TYPE: PRT
<213> ORGANISM: Homo sapiens

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Ser Ala Tyr
65                  70                  75                  80

Met Glu Leu Ser Ser Leu Arg Ser Asp Asp Thr Ala Val Tyr Tyr Cys
                85                  90                  95

Ala Arg Gly Pro His Thr Phe Gly Ser Gly Ser Tyr Pro Phe Asp Tyr
            100                 105                 110

Trp Gly Gln Gly Thr Leu Val Thr Val Ser Ser
        115                 120

<210> SEQ ID NO 23
<211> LENGTH: 321
<212> TYPE: DNA
<213> ORGANISM: Homo sapiens

<400> SEQUENCE: 23
gacatccaga tgacccagtc tccatcctcc ctgtctgcat ctgtaggaga cagagtcacc    60
atcacttgcc gggcaagtca gggcattaga agtgatttag ctggtatca gcagagacca   120 gggaacaccc ctaagcgcct gatctatgct gcatccagtt tacaaagtgg ggtcccatca   180
aggttcagcg gcagtggatc tgggacagaa ttcactctca caatcagcag cctgcagcct   240
gaagattttg caacttatta ctgtcaacag tataatagtt acccgctcac tttcggcgga   300
gggaccaagg tggagatcaa a                                             321

<210> SEQ ID NO 24
<211> LENGTH: 107
<212> TYPE: PRT
<213> ORGANISM: Homo sapiens

<400> SEQUENCE: 24

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Ser Asp
            20                  25                  30

Leu Gly Trp Tyr Gln Gln Arg Pro Gly Asn Thr Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 25
<211> LENGTH: 369
<212> TYPE: DNA
<213> ORGANISM: Homo sapiens

<400> SEQUENCE: 25
caggtgcagc tggtgcagtc tggggctgag gtgaagaagc ctggggcctc agtgaaggtc    60
tcctgcaagg cttctggatt ccccttcacc gactactata tgcactgggt gcgacaggcc   120
cctggacaag gcttgagtg gatgggatgg atcaactcta cagtggtgg cacaaactat    180 gcacagaagt tcagggcag ggtcaccatg accagggaca cgtccatcag cacagcctac    240
atggagctga gcaggctgag atctgacgac acggccgtgt attactgtgc gagagggccc   300
cattcctttg gttcggggag ttaccccttt gactactggg gccagggaac cctggtcacc   360
gtctcctca                                                           369

<210> SEQ ID NO 26
<211> LENGTH: 123
<212> TYPE: PRT
<213> ORGANISM: Homo sapiens

<400> SEQUENCE: 26

Gln Val Gln Leu Val Gln Ser Gly Ala Glu Val Lys Lys Pro Gly Ala

```
                1               5                   10                  15
Ser Val Lys Val Ser Cys Lys Ala Ser Gly Phe Pro Phe Thr Asp Tyr
                    20                  25                  30

Tyr Met His Trp Val Arg Gln Ala Pro Gly Gln Gly Leu Glu Trp Met
            35                  40                  45

Gly Trp Ile Asn Ser Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Pro His Ser Phe Gly Ser Gly Ser Tyr Pro Phe Asp Tyr
            100                 105                 110

Trp Gly Gln Gly Thr Leu Val Thr Val Ser Ser
        115                 120

<210> SEQ ID NO 27
<211> LENGTH: 321
<212> TYPE: DNA
<213> ORGANISM: Homo sapiens

<400> SEQUENCE: 27
gacatccaga tgacccagtc tccatcctcc ctgtctgcat ctgtaggaga cagagtcacc        60
atcacttgcc gggcaagtca gggcattaga agtgatttag ctggtatcag cagagacca       120 gggaaaaccc ctaagcgcct gatctatgct gcatccagtt tgcaaagtgg ggtcccatca      180
aggttcagcg gcagtggatc tgggacagaa ttcactctca caatcagcag cctgcagcct      240
gaagattttg caacttatta ctgtcaacag tataatagtt acccgctcac tttcggcgga     300
gggaccaagg tggagatcaa a                                                 321

<210> SEQ ID NO 28
<211> LENGTH: 107
<212> TYPE: PRT
<213> ORGANISM: Homo sapiens

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Asp
                20                  25                  30

Leu Gly Trp Tyr Gln Gln Arg Pro Gly Lys Thr Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 29
<211> LENGTH: 369
<212> TYPE: DNA
<213> ORGANISM: Homo sapiens

<400> SEQUENCE: 29
```

```
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaactcta acagtggtgg cacaaactat      180
gcacagaagt tcagggcag gtcaccatg accagggaca cgtccatcag cacagcctac       240
atggagctga gcaggctgag atctgacgac acggccgtgt attactgtgc gagagggccc     300
cattcctttg gttcggggag ttacccctt gactactggg gccagggaac cctggtcacc      360
gtctcctca                                                             369
```

<210> SEQ ID NO 30
<211> LENGTH: 123
<212> TYPE: PRT
<213> ORGANISM: Homo sapiens

<400> SEQUENCE: 30

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Ser Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Pro His Ser Phe Gly Ser Gly Ser Tyr Pro Phe Asp Tyr
            100                 105                 110

Trp Gly Gln Gly Thr Leu Val Thr Val Ser Ser
        115                 120
```

<210> SEQ ID NO 31
<211> LENGTH: 321
<212> TYPE: DNA
<213> ORGANISM: Homo sapiens

<400> SEQUENCE: 31

```
gacatccaga tgacccagtc tccatcctcc ctgtctgcat ctgtaggaga cagagtcacc      60
atcacttgcc gggcaagtca gggcattaga agtgatttag ctggtatca gcagagacca     120 gggaaacccc ctaagcgcct gatctatgct gcatccagtt tgcaaagtgg ggtcccatca     180
aggttcagcg gcagtggatc tgggacagaa ttcactctca caatcagcag cctgcagcct    240
gaagattttg caactatta ctgtcaacag tataatagtt acccgctcac tttcggcgga     300
gggaccaagg tggagatcaa a                                               321
```

<210> SEQ ID NO 32
<211> LENGTH: 107
<212> TYPE: PRT
<213> ORGANISM: Homo sapiens

<400> SEQUENCE: 32

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Ser Asp
```

```
                    20                  25                  30
Leu Gly Trp Tyr Gln Gln Arg Pro Gly Lys Thr Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys
            100                 105
```

<210> SEQ ID NO 33
<211> LENGTH: 369
<212> TYPE: DNA
<213> ORGANISM: Homo sapiens

<400> SEQUENCE: 33

```
caggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atcaaccct a acagtggtgg cacaaactat   180
gcacagaagt tcagggcag gtcaccatg accaggact cgtccatcag cacagcctac   240
atggaactga gcaggctgag atctgacgac acggccgtgt attactgtgc gagagggccc   300
cataccttg gttcggggag ttacccctt gactactggg gccagggaac cctggtcccc   360
gtctcctca                                                           369
```

<210> SEQ ID NO 34
<211> LENGTH: 123
<212> TYPE: PRT
<213> ORGANISM: Homo sapiens

<400> SEQUENCE: 34

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Ser Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Pro His Thr Phe Gly Ser Gly Ser Tyr Pro Phe Asp Tyr
            100                 105                 110

Trp Gly Gln Gly Thr Leu Val Pro Val Ser Ser
        115                 120
```

<210> SEQ ID NO 35
<211> LENGTH: 321
<212> TYPE: DNA
<213> ORGANISM: Homo sapiens

<400> SEQUENCE: 35

```
gacatccagt tgacccagtc tccatcttcc ctgtctgcat ctgtaggaga cagagtcacc    60
atcacttgcc gggcaagtca gggcattaga agtgatttag gctggtatca gcagagacca   120
gggaaaaccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtcaacag tataatagtt acccgctcac tttcggcgga   300
gggaccaagg tggagatcaa a                                             321

<210> SEQ ID NO 36
<211> LENGTH: 107
<212> TYPE: PRT
<213> ORGANISM: Homo sapiens

<400> SEQUENCE: 36

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Arg Ser Asp
             20                  25                  30

Leu Gly Trp Tyr Gln Gln Arg Pro Gly Lys Thr Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys
            100                 105

<210> SEQ ID NO 37
<211> LENGTH: 369
<212> TYPE: DNA
<213> ORGANISM: Homo sapiens

<400> SEQUENCE: 37
caggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg atgggatgg atcaaccta acagtggtgg cacaaactat   180
gcacagaagt tcagggcag ggtcaccatg accagggaca cgtccatcag cacagcctac   240
atggagctga gcaggctgag atctgacgac acggccgtgt attactgtgc gagagggccc   300
catacctttg gttcggggag ttaccccttt gactactggg gccagggaac cctggtcacc   360
gtctcctca                                                          369

<210> SEQ ID NO 38
<211> LENGTH: 123
<212> TYPE: PRT
<213> ORGANISM: Homo sapiens

<400> SEQUENCE: 38

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45
```

Gly Trp Ile Asn Pro Asn Ser Gly Thr Asn Tyr Ala Gln Lys Phe
        50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Pro His Thr Phe Ser Gly Ser Tyr Pro Phe Asp Tyr
            100                 105                 110

Trp Gly Gln Gly Thr Leu Val Thr Val Ser Ser
        115                 120

<210> SEQ ID NO 39
<211> LENGTH: 321
<212> TYPE: DNA
<213> ORGANISM: Homo sapiens

<400> SEQUENCE: 39
gacatccaga tgacccagtc tccatcctcc ctgtctgcat ctgtaggaga cagagtcacc    60
atcacttgcc gggcaagtca gggcattaga agtgatttag gctggtatca gcagagacca   120
gggaaaaccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtcaacag tataatagtt acccgctcac tttcggcgga   300
gggaccaagg tggagatcaa a                                             321

<210> SEQ ID NO 40
<211> LENGTH: 107
<212> TYPE: PRT
<213> ORGANISM: Homo sapiens

<400> SEQUENCE: 40

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Ser Asp
                 20                  25                  30

Leu Gly Trp Tyr Gln Gln Arg Pro Gly Lys Thr Pro Lys Arg Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys
            100                 105

<210> SEQ ID NO 41
<211> LENGTH: 351
<212> TYPE: DNA
<213> ORGANISM: Homo sapiens

<400> SEQUENCE: 41
caggtgcagc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaatactat   180

-continued

```
gcagactccg tgaagggccg attcaccatc tccagagaca attccaagaa cacgctgtat      240
ctgcaaatga acagcctgag agccgaggac acggctgtgt attactgtgc gagggggac      300 ttttactggt tcgacccctg gggccaggga accctggtca ccgtctcctc a              351
```

<210> SEQ ID NO 42
<211> LENGTH: 117
<212> TYPE: PRT
<213> ORGANISM: Homo sapiens

<400> SEQUENCE: 42

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asp Phe Tyr Trp Phe Asp Pro Trp Gly Gln Gly Thr Leu
            100                 105                 110

Val Thr Val Ser Ser
        115
```

<210> SEQ ID NO 43
<211> LENGTH: 321
<212> TYPE: DNA
<213> ORGANISM: Homo sapiens

<400> SEQUENCE: 43

```
gacatccaga tgacccagtc tccatcttcc ctgtctgcat ctgtaggaga cagagtcacc       60
atcacttgcc gggcaagtca gggcattaga agtgatttag gctggtatca gcagagacca      120
gggaaaaccc ctaagcgcct gatctatgct gcatccagtt tgcaaagtgg ggtcccatca      180
aggttcagcg gcagtggatc tgggacagaa ttcactctca caatcagcag cctgcagcct      240
gaagattttg caacttatta ctgtcaacag tataatagtt acccgctcac tttcggcgga      300
gggaccaagg tggagatcaa a                                                321
```

<210> SEQ ID NO 44
<211> LENGTH: 107
<212> TYPE: PRT
<213> ORGANISM: Homo sapiens

<400> SEQUENCE: 44

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Ser Asp
             20                  25                  30

Leu Gly Trp Tyr Gln Gln Arg Pro Gly Lys Thr Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
```

```
                65                  70                  75                  80
Glu Asp Phe Ala Thr Tyr Tyr Cys Gln Gln Tyr Asn Ser Tyr Pro Leu
                    85                  90                  95

Thr Phe Gly Gly Gly Thr Lys Val Glu Ile Lys
            100                 105

<210> SEQ ID NO 45
<211> LENGTH: 342
<212> TYPE: DNA
<213> ORGANISM: Homo sapiens

<400> SEQUENCE: 45
caggtgcagc tggtgcagtc tggggctgag gtgaagaagc ctggggcctc agtgaaggtc       60
tcctgcaagg cttctggata caccttcacc ggctactata tgcactgggt gcgacaggcc     120
cctggacaag gcttgagtg atgggatgg atcaaccta acagtggtgg cacaaactat        180
gcacagaagt tcagagcag gtcaccatg accaggaca cgtccatcag cacagcctac        240
atggagctga gcaggctgag atctgacgac acggccgtgt attactgtgc ggggggatg     300 ggggacgtct ggggccaagg gaccacggtc accgtctcct ca                        342

<210> SEQ ID NO 46
<211> LENGTH: 114
<212> TYPE: PRT
<213> ORGANISM: Homo sapiens

<400> SEQUENCE: 46

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Trp Ile Asn Pro Asn Ser Gly Gly Thr Asn Tyr Ala Gln Lys Phe
         50                  55                  60

Gln Ser Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Gly Gly Met Gly Asp Val Trp Gly Gln Gly Thr Thr Val Thr Val
             100                 105                 110

Ser Ser

<210> SEQ ID NO 47
<211> LENGTH: 321
<212> TYPE: DNA
<213> ORGANISM: Homo sapiens

<400> SEQUENCE: 47
gacatccaga tgacccagtc tccatcctcc ctgtctgcat ctgtaggaga cagagtcacc       60
atcacttgcc gggcaagtca gggcattaga aatgatttag ctggtatca gcagaaacca      120 gggaaagccc ctaagcgcct gatctatgct gcatccagtt tgcaaagtgg ggtcccatca     180
aggttcagcg gcagtggatc tgggacagaa ttcactctca caatcagcag cctgcagcct    240
gaagattttg caacttatta ctgtctacag tataatagtt acccgtggac gttcggccaa    300
gggaccaagg tggaaatcaa a                                               321
```

<210> SEQ ID NO 48
<211> LENGTH: 107
<212> TYPE: PRT
<213> ORGANISM: Homo sapiens

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Trp
                85                  90                  95

Thr Phe Gly Gln Gly Thr Lys Val Glu Ile Lys
            100                 105

<210> SEQ ID NO 49
<211> LENGTH: 351
<212> TYPE: DNA
<213> ORGANISM: Homo sapiens

<400> SEQUENCE: 49
caggtgcagc tggtggagtc cggggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagaggggac     300
ttttactggt tcgaccccctg gggccaggga accctggtca ccgtctcctc a              351

<210> SEQ ID NO 50
<211> LENGTH: 117
<212> TYPE: PRT
<213> ORGANISM: Homo sapiens

<400> SEQUENCE: 50

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Phe Tyr Trp Phe Asp Pro Trp Gly Gln Gly Thr Leu
            100                 105                 110

Val Thr Val Ser Ser

<210> SEQ ID NO 51
<211> LENGTH: 321
<212> TYPE: DNA
<213> ORGANISM: Homo sapiens

<400> SEQUENCE: 51

| | | | | | |
|---|---|---|---|---|---|
| gacatccaga | tgacccagtc | tccatcctcc | ctgtctgcat | ctgtaggaga | cagagtcacc | 60 |
| atcacttgcc | gggcaagtca | gggcattaga | aatgatttag | gctggtatca | gcagaaacca | 120 |
| gggaaagccc | ctaagcgcct | gatctatgct | gcatccagtt | tgcaaagtgg | ggtcccatca | 180 |
| aggttcagcg | gcagtggatc | tgggacagaa | ttcactctca | caatcagcag | cctgcagcct | 240 |
| gaagattttg | caacttatta | ctgtctacag | tataatagtt | acccgtggac | gttcggccaa | 300 |
| gggaccaagg | tggaaatcaa | a | | | | 321 |

<210> SEQ ID NO 52
<211> LENGTH: 107
<212> TYPE: PRT
<213> ORGANISM: Homo sapiens

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Trp
                85                  90                  95

Thr Phe Gly Gln Gly Thr Lys Val Glu Ile Lys
            100                 105

<210> SEQ ID NO 53
<211> LENGTH: 375
<212> TYPE: DNA
<213> ORGANISM: Homo sapiens

<400> SEQUENCE: 53

| | | | | | |
|---|---|---|---|---|---|
| caggtgcagc | tggtggagtc | tgggggaggc | gtggtccagc | ctgggacgtc | cctgagactc | 60 |
| tcctgtgcag | cgtctggatt | caccttcagt | agctatggca | tacactgggt | ccgccaggct | 120 |
| ccaggcaagg | ggctggagtg | ggtggcagtt | atatggtatg | atggaagtaa | taaattccat | 180 |
| gcagactccg | tgaagggccg | attcaccatc | tccagagaca | attccaagaa | cacgctgtat | 240 |
| ctgcaaatga | acagcctgag | agccgaggac | acggctgtgt | attactgtgc | gagagaccca | 300 |
| ctaggatatt | gtagtagtac | cagctgctct | tactttgact | actggggcca | gggaaccctg | 360 |
| gtcaccgtct | cctca | | | | | 375 |

<210> SEQ ID NO 54
<211> LENGTH: 125
<212> TYPE: PRT
<213> ORGANISM: Homo sapiens

<400> SEQUENCE: 54

Gln Val Gln Leu Val Glu Ser Gly Gly Val Val Gln Pro Gly Thr
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Trp Tyr Asp Gly Ser Asn Lys Phe His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Leu Gly Tyr Cys Ser Ser Thr Ser Cys Ser Tyr Phe
            100                 105                 110

Asp Tyr Trp Gly Gln Gly Thr Leu Val Thr Val Ser Ser
        115                 120                 125

<210> SEQ ID NO 55
<211> LENGTH: 321
<212> TYPE: DNA
<213> ORGANISM: Homo sapiens

<400> SEQUENCE: 55
gacatccaga tgacccagtc tccatcttcc gtgtctgcat ctgtaggaga cagagtcacc     60
atcacttgtc gggcgagtca gggtattagc aactggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ccatcagcag cctgcagcct    240
gaagattttg caacttacta ttgtcaacag gctaacaatt tcccgctcac tttcggcgga    300
gggaccaagg tggagatcaa a                                              321

<210> SEQ ID NO 56
<211> LENGTH: 107
<212> TYPE: PRT
<213> ORGANISM: Homo sapiens

<400> SEQUENCE: 56

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Leu
                85                  90                  95

Thr Phe Gly Gly Gly Thr Lys Val Glu Ile Lys
            100                 105

<210> SEQ ID NO 57
<211> LENGTH: 375
<212> TYPE: DNA

<213> ORGANISM: Homo sapiens

<400> SEQUENCE: 57

| caggtgcagc | tggtggagtc | tgggggaggc | gtggtccagc | ctgggacgtc | cctgagactc | 60 |
| tcctgtgcag | cgtctggatt | caccttcagt | agctatggca | tacactgggt | ccgccaggct | 120 |
| ccaggcaagg | ggctggagtg | gtggcagtt | atatggtatg | atggaagtaa | taaattctat | 180 |
| gcagactccg | tgaagggccg | attcactatc | tccagagaca | attccaagaa | cacgctgtat | 240 |
| ctgcaaatga | acagcctgag | agccgaggac | acggctgtgt | attactgtgc | gagagaccca | 300 |
| ctaggatatt | gtagtagtac | cagctgctct | tactttgact | actggggcca | gggaaccctg | 360 |
| gtcaccgtct | cctca | | | | | 375 |

<210> SEQ ID NO 58
<211> LENGTH: 125
<212> TYPE: PRT
<213> ORGANISM: Homo sapiens

<400> SEQUENCE: 58

```
Gln Val Gln Leu Val Glu Ser Gly Gly Gly Val Val Gln Pro Gly Thr
  1               5                  10                  15
Ser Leu Arg Leu Ser Cys Ala Ala Ser Gly Phe Thr Phe Ser Ser Tyr
             20                  25                  30
Gly Ile His Trp Val Arg Gln Ala Pro Gly Lys Gly Leu Glu Trp Val
         35                  40                  45
Ala Val Ile Trp Tyr Asp Gly Ser Asn Lys Phe Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Asp Pro Leu Gly Tyr Cys Ser Ser Thr Ser Cys Ser Tyr Phe
            100                 105                 110
Asp Tyr Trp Gly Gln Gly Thr Leu Val Thr Val Ser Ser
        115                 120                 125
```

<210> SEQ ID NO 59
<211> LENGTH: 321
<212> TYPE: DNA
<213> ORGANISM: Homo sapiens

<400> SEQUENCE: 59

| gacatccaga | tgacccagtc | tccatcttcc | gtgtctgcat | ctgtaggaga | cagagtcacc | 60 |
| atcacttgtc | gggcgagtca | gggtattagc | aactggttag | cctggtatca | gcagaaacca | 120 |
| gggaaagccc | ctaagctcct | gatctatgct | gcatccagtt | tgcaaagtgg | ggtcccatca | 180 |
| cggttcagcg | gcagtggatc | tgggacagat | ttcactctca | ccatccgcag | cctgcagcct | 240 |
| gaagattttg | caacttacta | ttgtcaacag | gctaacaatt | tcccgctcac | tttcggcgga | 300 |
| gggaccaagg | tggagatcaa | a | | | | 321 |

<210> SEQ ID NO 60
<211> LENGTH: 107
<212> TYPE: PRT
<213> ORGANISM: Homo sapiens

<400> SEQUENCE: 60

Asp Ile Gln Met Thr Gln Ser Pro Ser Ser Val Ser Ala Ser Val Gly

```
                1               5              10              15
Asp Arg Val Thr Ile Thr Cys Arg Ala Ser Gln Gly Ile Ser Asn Trp
                20                          25                          30

Leu Ala Trp Tyr Gln Gln Lys Pro Gly Lys Ala Pro Lys Leu Leu Ile
            35                          40                          45

Tyr Ala Ala Ser Ser Leu Gln Ser Gly Val Pro Ser Arg Phe Ser Gly
        50                          55                          60

Ser Gly Ser Gly Thr Asp Phe Thr Leu Thr Ile Arg Ser Leu Gln Pro
 65                         70                          75                          80

Glu Asp Phe Ala Thr Tyr Tyr Cys Gln Gln Ala Asn Asn Phe Pro Leu
                    85                          90                          95

Thr Phe Gly Gly Gly Thr Lys Val Glu Ile Lys
                100                         105
```

<210> SEQ ID NO 61
<211> LENGTH: 354
<212> TYPE: DNA
<213> ORGANISM: Homo sapiens

<400> SEQUENCE: 61

```
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagaggaggg     300
gacggtgaac ggtttgacta ctggggccag ggaaccctgg tcaccgtctc ctca            354
```

<210> SEQ ID NO 62
<211> LENGTH: 118
<212> TYPE: PRT
<213> ORGANISM: Homo sapiens

<400> SEQUENCE: 62

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                          30

Gly Met His Trp Val Arg Gln Ala Pro Gly Lys Gly Leu Glu Trp Val
        35                          40                          45

Ala Val Ile Trp Tyr Asp Gly Ser Asn Lys Tyr Tyr Ala Asp Ser Val
    50                          55                          60

Lys Gly Arg Phe Thr Ile Ser Arg Asp Asn Ser Lys Asn Thr Leu Tyr
 65                         70                          75                          80

Leu Gln Met Asn Ser Leu Arg Ala Glu Asp Thr Ala Val Tyr Tyr Cys
                    85                          90                          95

Ala Arg Gly Gly Asp Gly Glu Arg Phe Asp Tyr Trp Gly Gln Gly Thr
                100                         105                         110

Leu Val Thr Val Ser Ser
            115
```

<210> SEQ ID NO 63
<211> LENGTH: 342
<212> TYPE: DNA
<213> ORGANISM: Homo sapiens

<400> SEQUENCE: 63

```
gatgttgtga tgactcagtc tccactctcc ctgcccgtca cccttggaca gccggcctcc    60
atctcctgca ggtctagtca aagccgcgta tacagtgatg aaacaccttt cttgaattgg   120
tttcagcaga ggccaggcca atttccaagg cgcctaattt ataaggtttc aactgggac    180 tctggggtcc cagacagatt cagcggcagt gggtcaggca ctgatttcac actgaaaatc   240
agcagggtgg aggctgagga tgttggggtt tattactgca tgcaaggtac acactggcct   300
ccttatgtgc agttttggcc aggggaccaa gctggagatc aa                      342
```

<210> SEQ ID NO 64
<211> LENGTH: 114
<212> TYPE: PRT
<213> ORGANISM: Homo sapiens

<400> SEQUENCE: 64

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Arg Val Tyr Ser
            20                  25                  30

Asp Gly Asn Thr Phe Leu Asn Trp Phe Gln Gln Arg Pro Gly Gln Phe
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Tyr Val Gln Phe Trp Pro Gly Asp Gln Ala Gly
            100                 105                 110

Asp Gln

<210> SEQ ID NO 65
<211> LENGTH: 375
<212> TYPE: DNA
<213> ORGANISM: Homo sapiens

<400> SEQUENCE: 65

```
caggtgcagc tggtggagtc tgggggaggc gtggtccagc ctgggaggtc cctgagactc    60
tcctgtgcag cgtctggatt caccttcaga agctatggca tgcactgggt ccgccaggct   120
ccaggcaagg ggctggagtg ggtggcagtt ataaggcatg atggaagtaa taatataat    180 gcagactccg tgaagggccg attcaccatc tccagagaca attccaagaa cacgctgtat   240
ctgcaaatga acagtctgag agccgaggac acggctgtgt attactgtgc gagagaccca   300
ctaggatatt gtagtagtac cagctgctct tactttgact actggggcca gggaaccctg   360
gtcaccgtct cctca                                                    375
```

<210> SEQ ID NO 66
<211> LENGTH: 125
<212> TYPE: PRT
<213> ORGANISM: Homo sapiens

<400> SEQUENCE: 66

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Arg Ser Tyr
            20                  25                  30

```
Gly Met His Trp Val Arg Gln Ala Pro Gly Lys Gly Leu Glu Trp Val
         35                  40                  45

Ala Val Ile Arg His Asp Gly Ser Asn Lys Tyr Asn Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Pro Leu Gly Tyr Cys Ser Ser Thr Ser Cys Ser Tyr Phe
             100                 105                 110

Asp Tyr Trp Gly Gln Gly Thr Leu Val Thr Val Ser Ser
            115                 120                 125

<210> SEQ ID NO 67
<211> LENGTH: 321
<212> TYPE: DNA
<213> ORGANISM: Homo sapiens

<400> SEQUENCE: 67
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct acatccagtt tgcaaagtgg ggtcccatca     180
aggttcagcg gcagtggatc tgggacagat ttcactctca ccatcagcag cctgcagcct     240
gaagattttg caacttacta ttgtcaacag gctaacaatt tcccgctcac tttcggcgga     300
gggaccaagg tggagatcaa a                                               321

<210> SEQ ID NO 68
<211> LENGTH: 107
<212> TYPE: PRT
<213> ORGANISM: Homo sapiens

<400> SEQUENCE: 68

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Thr Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Asn Phe Pro Leu
                 85                  90                  95

Thr Phe Gly Gly Gly Thr Lys Val Glu Ile Lys
            100                 105

<210> SEQ ID NO 69
<211> LENGTH: 372
<212> TYPE: DNA
<213> ORGANISM: Homo sapiens

<400> SEQUENCE: 69
caggtgcagc tgcaggagtc gggcccagga ctggtgaagc cttcggagac cctgtccctc      60
acctgcactg tctctgatgg ctccatcagt agtttctact ggagctggat ccggcagccc     120
```

```
ccagggaagg gactggagtg gattgggtat atctattaca gtgggagcac caactacaac    180
ccctccctca agagtcgagt caccatatca gtagacacgt ccaagaacca gttctccctg    240
aagctgagct ctgtgaccgc tgcggacacg gccgtgtatt actgtgcgag agattacgat    300
atcttgactg gttattccaa ctactacggt atggacgtct ggggccaagg gaccacggtc    360
accgtctcct ca                                                         372
```

<210> SEQ ID NO 70
<211> LENGTH: 124
<212> TYPE: PRT
<213> ORGANISM: Homo sapiens

<400> SEQUENCE: 70

```
Gln Val Gln Leu Gln Glu Ser Gly Pro Gly Leu Val Lys Pro Ser Glu
  1               5                  10                  15

Thr Leu Ser Leu Thr Cys Thr Val Ser Asp Gly Ser Ile Ser Ser Phe
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Tyr Asp Ile Leu Thr Gly Tyr Ser Asn Tyr Tyr Gly Met Asp
            100                 105                 110

Val Trp Gly Gln Gly Thr Thr Val Thr Val Ser Ser
        115                 120
```

<210> SEQ ID NO 71
<211> LENGTH: 321
<212> TYPE: DNA
<213> ORGANISM: Homo sapiens

<400> SEQUENCE: 71

```
gacatccaga tgacccagtc tccatcctcc ctgtctgcat ctgtaggaga cagagtcacc     60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctgcag cataatagtt acccattcac tttcggccct    300
gggaccaaac tggatatcaa a                                              321
```

<210> SEQ ID NO 72
<211> LENGTH: 107
<212> TYPE: PRT
<213> ORGANISM: Homo sapiens

<400> SEQUENCE: 72

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45
```

Tyr Ala Ala Ser Ser Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Phe
                 85                  90                  95

Thr Phe Gly Pro Gly Thr Lys Leu Asp Ile Lys
            100                 105

<210> SEQ ID NO 73
<211> LENGTH: 345
<212> TYPE: DNA
<213> ORGANISM: Homo sapiens

<400> SEQUENCE: 73
caggtgcagc tggtgcagtc tggggctgag gtgaagaagc ctggggcctc agtgaaggtc     60
tcctgcaagg cttctggata caccttcacc ggctactata tgcactgggt gcgacaggcc    120
cctggacaag gcttgagtg gatgggatgg atcaaccta acagtggtgg cacaaactat    180
gcacagaagt ttcagggcag ggtcaccatg accagggaca cgtccatcag cacagcctac    240
atggagctga gcaggctgag atctgacgac acggccgtgt tttactgtgc gggtgggacc    300
tacttggact actggggcca gggaaccctg gtcaccgtct cctca                    345

<210> SEQ ID NO 74
<211> LENGTH: 115
<212> TYPE: PRT
<213> ORGANISM: Homo sapiens

<400> SEQUENCE: 74

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
             35                  40                  45

Gly Trp Ile Asn Pro Asn Ser Gly Gly Thr Asn Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Phe Tyr Cys
                 85                  90                  95

Ala Gly Gly Thr Tyr Leu Asp Tyr Trp Gly Gln Gly Thr Leu Val Thr
            100                 105                 110

Val Ser Ser
        115

<210> SEQ ID NO 75
<211> LENGTH: 321
<212> TYPE: DNA
<213> ORGANISM: Homo sapiens

<400> SEQUENCE: 75
gacatccaga tgacccagtc tccatcctcc ctgtctgcat ctgtaggaga cagagtcacc     60
atcacttgcc gggcaagtca gggcattaga aatgatttag cctggtatca gcagaaacca    120
gggaaagccc ctaagcgcct gatctatgct gcatccagtt tgcaaagtgg ggtcccatca    180

-continued

```
aggttcagcg gcagtggatc tgggacagaa ttcactctca caatcagcag cctgcagcct    240
gaagattttg caacttatta ctgtctacag tataatagtt acccgatcac cttcggccaa    300
gggacacgac tggagattaa a                                              321
```

<210> SEQ ID NO 76
<211> LENGTH: 107
<212> TYPE: PRT
<213> ORGANISM: Homo sapiens

<400> SEQUENCE: 76

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Ile
                85                  90                  95

Thr Phe Gly Gln Gly Thr Arg Leu Glu Ile Lys
            100                 105
```

<210> SEQ ID NO 77
<211> LENGTH: 345
<212> TYPE: DNA
<213> ORGANISM: Homo sapiens

<400> SEQUENCE: 77

```
caggttcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt ataatggtaa cacaaactat    180
gcacagaagc tccagggcag aggcaccatg gccacagaca catccacgag cacagcctac    240
atggagctga ggagcctgag atctgacgac acggccgtgt attactgtgc ggttgggagg    300
taccttgact actggggcca gggaaccctg gtcaccgtct cctca                    345
```

<210> SEQ ID NO 78
<211> LENGTH: 115
<212> TYPE: PRT
<213> ORGANISM: Homo sapiens

<400> SEQUENCE: 78

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Gly Thr Met Ala Thr Asp Thr Ser Thr Ser Thr Ala Tyr
65                  70                  75                  80

Met Glu Leu Arg Ser Leu Arg Ser Asp Asp Thr Ala Val Tyr Tyr Cys
```

85                  90                  95
Ala Val Gly Arg Tyr Leu Asp Tyr Trp Gly Gln Gly Thr Leu Val Thr
                100                 105                 110

Val Ser Ser
        115

<210> SEQ ID NO 79
<211> LENGTH: 321
<212> TYPE: DNA
<213> ORGANISM: Homo sapiens

<400> SEQUENCE: 79
gacatccaga tgacccagtc tccatcctcc ctgtctgcat ctgtaggaga cagagtcacc    60
atcacttgcc gggcaagtca ggacattaga aatgatttag ctggtatca gcagaaacca   120 gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag tataatagtt accctctcac tttcggcgga   300
gggaccaagg tggagatcaa a                                             321

<210> SEQ ID NO 80
<211> LENGTH: 107
<212> TYPE: PRT
<213> ORGANISM: Homo sapiens

<400> SEQUENCE: 80

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Asn Ser Tyr Pro Leu
                 85                  90                  95

Thr Phe Gly Gly Gly Thr Lys Val Glu Ile Lys
                100                 105

<210> SEQ ID NO 81
<211> LENGTH: 351
<212> TYPE: DNA
<213> ORGANISM: Homo sapiens

<400> SEQUENCE: 81
caggtgcagc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagaggggac   300
ttttactggt tcgaccctg gggccaggga accctggtca ccgtctcctc a             351

<210> SEQ ID NO 82

<211> LENGTH: 117
<212> TYPE: PRT
<213> ORGANISM: Homo sapiens

<400> SEQUENCE: 82

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Phe Tyr Trp Phe Asp Pro Trp Gly Gln Gly Thr Leu
            100                 105                 110

Val Thr Val Ser Ser
        115

<210> SEQ ID NO 83
<211> LENGTH: 321
<212> TYPE: DNA
<213> ORGANISM: Homo sapiens

<400> SEQUENCE: 83
gacatccaga tgacccagtc tccatcctcc ctgtctgcat ctgtaggaga cagagtcacc      60
atcacttgcc gggcaagtca ggacattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag tataatagtt accctctcac tttcggcgga     300
gggaccaagg tggagatcaa a                                               321

<210> SEQ ID NO 84
<211> LENGTH: 107
<212> TYPE: PRT
<213> ORGANISM: Homo sapiens

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Leu
                85                  90                  95

Thr Phe Gly Gly Gly Thr Lys Val Glu Ile Lys
            100                 105

<210> SEQ ID NO 85
<211> LENGTH: 369
<212> TYPE: DNA
<213> ORGANISM: Homo sapiens

<400> SEQUENCE: 85

```
caggtgcagc tggtgcagtc tggggctgag gtgaagaagc ctggggcctc agtgaaggtc        60
tcctgcaagg cttctggata caccttcacc ggctactata tgcactgggt gcgacaggcc       120
cctggacaag gcttgagtg gatgggatgg atcaaccta acagtggtgg cacaaactat        180
gcacagaagt tcagggcag gtcaccatg accaggaca cgtccatcag cacagcctac        240
atggagctga gcaggctgag atctgacgac acggccgtgt attactgtgc gagagggccc       300
catacctttg gttcggggag ttaccccttt gactactggg gccagggaac cctggtcacc       360
gtctcctca                                                               369
```

<210> SEQ ID NO 86
<211> LENGTH: 123
<212> TYPE: PRT
<213> ORGANISM: Homo sapiens

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Pro His Thr Phe Gly Ser Gly Ser Tyr Pro Phe Asp Tyr
            100                 105                 110

Trp Gly Gln Gly Thr Leu Val Thr Val Ser Ser
        115                 120

<210> SEQ ID NO 87
<211> LENGTH: 321
<212> TYPE: DNA
<213> ORGANISM: Homo sapiens

<400> SEQUENCE: 87

```
gacatccaga tgacccagtc tccatcctcc ctgtctgcat ctgtaggaga cagagtcacc        60
atcacttgcc gggcaagtca ggacattaga atgatttag ctggtatca gcagaaacca       120 gggaaagccc ctaagcgcct gatctatgct gcatccagtt tgcaaagtgg ggtcccatca       180
aggttcagcg gcagtggatc tgggacagaa ttcactctca caatcagcag cctgcagcct       240
gaagattttg caacttatta ctgtctacag tataatagtt accctctcac tttcggcgga       300
gggaccaagg tggagatcaa a                                                 321
```

<210> SEQ ID NO 88
<211> LENGTH: 107
<212> TYPE: PRT
<213> ORGANISM: Homo sapiens

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Leu
                85                  90                  95

Thr Phe Gly Gly Gly Thr Lys Val Glu Ile Lys
            100                 105

<210> SEQ ID NO 89
<211> LENGTH: 345
<212> TYPE: DNA
<213> ORGANISM: Homo sapiens

<400> SEQUENCE: 89
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cccggacaag ggcttgagtg gatgggatgg atcaaccctaacagtggtgg cacaaactat     180 gcacagaagt tcagggcagg gtcaccatg accagggaca cgtccatcag cacagcctac     240
atggagctga gcaggctgag atctgacgac acggccgtgt tttactgtgc gggtgggacc     300
tacttggact actggggcca gggaaccctg gtcaccgtct cctca                    345

<210> SEQ ID NO 90
<211> LENGTH: 115
<212> TYPE: PRT
<213> ORGANISM: Homo sapiens

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Phe Tyr Cys
                85                  90                  95

Ala Gly Gly Thr Tyr Leu Asp Tyr Trp Gly Gln Gly Thr Leu Val Thr
            100                 105                 110

Val Ser Ser
        115

<210> SEQ ID NO 91
<211> LENGTH: 321

-continued

```
<212> TYPE: DNA
<213> ORGANISM: Homo sapiens

<400> SEQUENCE: 91
gacatccaga tgacccagtc tccatcctcc ctgtctgcat ctgtaggaga cagagtcacc    60
atcacttgcc gggcaagtca ggacattaga aatgatttag ctggtatcag cagaaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag tataatagtt accctctcac tttcggcgga   300
gggaccaagg tggagatcaa a                                              321

<210> SEQ ID NO 92
<211> LENGTH: 107
<212> TYPE: PRT
<213> ORGANISM: Homo sapiens

<400> SEQUENCE: 92

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Leu
                85                  90                  95

Thr Phe Gly Gly Gly Thr Lys Val Glu Ile Lys
            100                 105

<210> SEQ ID NO 93
<211> LENGTH: 3768
<212> TYPE: DNA
<213> ORGANISM: SARS coronavirus

<400> SEQUENCE: 93
atgtttattt tcttattatt tcttactctc actagtggta gtgaccttga

```
acatttatgc tcaagtatga tgaaaatggt acaatcacag atgctgttga ttgttctcaa    840
aatccacttg ctgaactcaa atgctctgtt aagagctttg agattgacaa aggaatttac    900
cagacctcta atttcagggt tgttccctca ggagatgttg tgagattccc taatattaca    960
aacttgtgtc cttttggaga ggtttttaat gctactaaat tcccttctgt ctatgcatgg   1020
gagaggaaaa gaattctaa ttgtgttgct gattactctg tgctctacaa ctcaacatct   1080
ttttcaacct ttaagtgcta tggcgtttct gccactaagt tgaatgatct ttgcttctcc   1140
aatgtctatg cagattcttt tgtagtcaag ggagatgatg taagacaaat agcgccagga   1200
caaactggtg ttattgctga ttataattat aaattgccag atgatttcat gggttgtgtc   1260
cttgcttgga atactaggaa cattgatgct acttcaactg gtaattataa ttataaatat   1320
aggtatctta gacatggcaa gcttaggccc tttgagagag acatatctaa tgtgcctttc   1380
tctcctgatg gcaaaccttg cacccccacct gctcctaatt gttattggcc attaaatggt   1440
tatggttttt acaccactag tggcattggc taccaacctt acagagttgt agtactttct   1500
tttgaacttt taaatgcacc ggccacggtt tgtggaccaa aattatccac tgaccttatt   1560
aagaaccagt gtgtcaattt taatttaat ggactcactg gtactggtgt gttaactcct   1620
tcttcaaaga gatttcaacc atttcaacaa tttggccgtg atgtttctga tttcactgat   1680
tccgttcgag atcctaaaac atctgaaata ttagacattt ccccttgctc ttttggggt   1740
gtaagtgtaa ttacacctgg aacaaatgct tcatctgaag ttgctgttct atatcaagat   1800
gttaactgca ctgatgtttc tacattaatt catgcagaac aactcacacc agcttggcgc   1860
atatattcta ctggaaacaa tgtattccag actcaagcag gctgtcttat aggagctgag   1920
catgtcgaca cttcttatga gtgcgacatt cctattggag ctggcatttg tgctagttac   1980
catacagttt cttcattacg tagtactagc caaaaatcta ttgtggctta tactatgtct   2040
ttaggtgctg atagttcaat tgcttactct aataacacca ttgctatacc tactaacttt   2100
tcaattagca ttactacaga agtaatgcct gtttctatgg ctaaaaacctc cgtagattgt   2160
aatatgtaca tctgcggaga ttctactgaa tgtgctaatt tgcttctcca atatggtagc   2220
ttttgcagac aactaaatcg tgcactctca ggtattgctg ctgaacagga tcgcaacaca   2280
cgtgaagtgt tcgttcaagt caaacaaatg tacaaaaccc caactttgaa agattttggt   2340
ggttttaatt tttcacaaat attacctgac cctctaaagc caactaagag gtcttttatt   2400
gaggacttgc tctttaataa ggtgacactc gctgatgctg gcttcatgaa gcaatatggc   2460
gaatgcctag gtgatattaa tgctagagat ctcattgtg cgcagaagtt caatggactt   2520
acagtgttgc cacctctgct cactgatgat atgattgctg cctacactgc tgctctagtt   2580
agtggtactg ccactgctgg atggacattt ggtgctggcg ctgctcttca ataccttttt   2640
gctatgcaaa tggcatatag gttcaatggc attggagtta cccaaaatgt tctctatgag   2700
aaccaaaaac aaatcgccaa ccaatttaac aaggcgatta gtcaaattca gaatcacttt   2760
acaacaacat caactgcatt gggcaagctg caagacgttg ttaaccagaa tgctcaagca   2820
ttaaacacac ttgttaaaca acttagctct aattttggtg caatttcaag tgtgctaaat   2880
gatatccttt cgcgacttga taagtcgag gcggaggtac aaattgacag gttaattaca   2940
ggcagacttc aaagccttca aacctatgta acacaacaac taatcagggc tgctgaaatc   3000
agggcttctg ctaatcttgc tgctactaaa atgtctgagt gtgttcttgg acaatcaaaa   3060
agagttgact tttgcggaaa gggctaccac cttatgtcct tcccacaagc agccccgcat   3120
```

-continued

```
ggtgttgtct tcctacatgt cacgtatgtg ccatcccagg agaggaactt caccacagcg    3180
ccagcaattt gtcatgaagg caaagcatac ttccctcgtg aaggtgtttt tgtgtttaat    3240
ggcacttctt ggtttattac acagaggaac ttcttttctc cacaaataat tactacagac    3300
aatacatttg tctcaggaaa ttgtgatgtc gttattggca tcattaacaa cacagtttat    3360
gatcctctgc aacctgagct tgactcattc aaagaagagc tggacaagta cttcaaaaat    3420
catacatcac cagatgttga tcttggcgac atttcaggca ttaacgcttc tgtcgtcaac    3480
attcaagaag aaattgaccg cctcaatgag gtcgctaaaa atttaaatga atcactcatc    3540
gaccttcaag aattgggaaa atatgagcaa tatattaaat ggccttggta tgtttggctc    3600
ggcttcattg ctggactaat tgccatcgtc atggttacaa tcttgctttg ttgcatgact    3660
agttgttgca gttgcctcaa gggtgcatgc tcttgtggtt cttgctgcaa gtttgatgag    3720
gatgactctg agccagttct caagggtgtc aaattacatt acacataa                 3768
```

<210> SEQ ID NO 94
<211> LENGTH: 1255
<212> TYPE: PRT
<213> ORGANISM: SARS coronavirus

<400> SEQUENCE: 94

```
Met Phe Ile Phe Leu Leu Phe Leu Thr Leu Thr Ser Gly Ser Asp Leu
  1               5                  10                  15

Asp Arg Cys Thr Thr Phe Asp Asp Val Gln Ala Pro Asn Tyr Thr Gln
             20                  25                  30

His Thr Ser Ser Met Arg Gly Val Tyr Tyr Pro Asp Glu Ile Phe Arg
         35                  40                  45

Ser Asp Thr Leu Tyr Leu Thr Gln Asp Leu Phe Leu Pro Phe Tyr Ser
     50                  55                  60

Asn Val Thr Gly Phe His Thr Ile Asn His Thr Phe Asp Asp Pro Val
 65                  70                  75                  80

Ile Pro Phe Lys Asp Gly Ile Tyr Phe Ala Ala Thr Glu Lys Ser Asn
                 85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Val Val Ser Lys Pro Met
    130                 135                 140

Gly Thr Arg Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Thr Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
```

-continued

```
                260                 265                 270
Thr Asp Ala Val Asp Cys Ser Gln Asn Pro Leu Ala Glu Leu Lys Cys
            275                 280                 285
Ser Val Lys Ser Phe Glu Ile Asp Lys Gly Ile Tyr Gln Thr Ser Asn
            290                 295                 300
Phe Arg Val Val Pro Ser Gly Asp Val Val Arg Phe Pro Asn Ile Thr
305                 310                 315                 320
Asn Leu Cys Pro Phe Gly Glu Val Phe Asn Ala Thr Lys Phe Pro Ser
            325                 330                 335
Val Tyr Ala Trp Glu Arg Lys Arg Ile Ser Asn Cys Val Ala Asp Tyr
            340                 345                 350
Ser Val Leu Tyr Asn Ser Thr Ser Phe Ser Thr Phe Lys Cys Tyr Gly
            355                 360                 365
Val Ser Ala Thr Lys Leu Asn Asp Leu Cys Phe Ser Asn Val Tyr Ala
            370                 375                 380
Asp Ser Phe Val Val Lys Gly Asp Asp Val Arg Gln Ile Ala Pro Gly
385                 390                 395                 400
Gln Thr Gly Val Ile Ala Asp Tyr Asn Tyr Lys Leu Pro Asp Asp Phe
            405                 410                 415
Met Gly Cys Val Leu Ala Trp Asn Thr Arg Asn Ile Asp Ala Thr Ser
            420                 425                 430
Thr Gly Asn Tyr Asn Tyr Lys Tyr Arg Tyr Leu Arg His Gly Lys Leu
            435                 440                 445
Arg Pro Phe Glu Arg Asp Ile Ser Asn Val Pro Phe Ser Pro Asp Gly
            450                 455                 460
Lys Pro Cys Thr Pro Pro Ala Pro Asn Cys Tyr Trp Pro Leu Asn Gly
465                 470                 475                 480
Tyr Gly Phe Tyr Thr Thr Ser Gly Ile Gly Tyr Gln Pro Tyr Arg Val
            485                 490                 495
Val Val Leu Ser Phe Glu Leu Leu Asn Ala Pro Ala Thr Val Cys Gly
            500                 505                 510
Pro Lys Leu Ser Thr Asp Leu Ile Lys Asn Gln Cys Val Asn Phe Asn
            515                 520                 525
Phe Asn Gly Leu Thr Gly Thr Gly Val Leu Thr Pro Ser Ser Lys Arg
            530                 535                 540
Phe Gln Pro Phe Gln Gln Phe Gly Arg Asp Val Ser Asp Phe Thr Asp
545                 550                 555                 560
Ser Val Arg Asp Pro Lys Thr Ser Glu Ile Leu Asp Ile Ser Pro Cys
            565                 570                 575
Ser Phe Gly Gly Val Ser Val Ile Thr Pro Gly Thr Asn Ala Ser Ser
            580                 585                 590
Glu Val Ala Val Leu Tyr Gln Asp Val Asn Cys Thr Asp Val Ser Thr
            595                 600                 605
Leu Ile His Ala Glu Gln Leu Thr Pro Ala Trp Arg Ile Tyr Ser Thr
            610                 615                 620
Gly Asn Asn Val Phe Gln Thr Gln Ala Gly Cys Leu Ile Gly Ala Glu
625                 630                 635                 640
His Val Asp Thr Ser Tyr Glu Cys Asp Ile Pro Ile Gly Ala Gly Ile
            645                 650                 655
Cys Ala Ser Tyr His Thr Val Ser Ser Leu Arg Ser Thr Ser Gln Lys
            660                 665                 670
Ser Ile Val Ala Tyr Thr Met Ser Leu Gly Ala Asp Ser Ser Ile Ala
            675                 680                 685
```

-continued

```
Tyr Ser Asn Asn Thr Ile Ala Ile Pro Thr Asn Phe Ser Ile Ser Ile
    690                 695                 700
Thr Thr Glu Val Met Pro Val Ser Met Ala Lys Thr Ser Val Asp Cys
705                 710                 715                 720
Asn Met Tyr Ile Cys Gly Asp Ser Thr Glu Cys Ala Asn Leu Leu Leu
                725                 730                 735
Gln Tyr Gly Ser Phe Cys Arg Gln Leu Asn Arg Ala Leu Ser Gly Ile
        740                 745                 750
Ala Ala Glu Gln Asp Arg Asn Thr Arg Glu Val Phe Val Gln Val Lys
            755                 760                 765
Gln Met Tyr Lys Thr Pro Thr Leu Lys Asp Phe Gly Gly Phe Asn Phe
    770                 775                 780
Ser Gln Ile Leu Pro Asp Pro Leu Lys Pro Thr Lys Arg Ser Phe Ile
785                 790                 795                 800
Glu Asp Leu Leu Phe Asn Lys Val Thr Leu Ala Asp Ala Gly Phe Met
                805                 810                 815
Lys Gln Tyr Gly Glu Cys Leu Gly Asp Ile Asn Ala Arg Asp Leu Ile
        820                 825                 830
Cys Ala Gln Lys Phe Asn Gly Leu Thr Val Leu Pro Pro Leu Leu Thr
            835                 840                 845
Asp Asp Met Ile Ala Ala Tyr Thr Ala Ala Leu Val Ser Gly Thr Ala
    850                 855                 860
Thr Ala Gly Trp Thr Phe Gly Ala Gly Ala Ala Leu Gln Ile Pro Phe
865                 870                 875                 880
Ala Met Gln Met Ala Tyr Arg Phe Asn Gly Ile Gly Val Thr Gln Asn
                885                 890                 895
Val Leu Tyr Glu Asn Gln Lys Gln Ile Ala Asn Gln Phe Asn Lys Ala
        900                 905                 910
Ile Ser Gln Ile Gln Glu Ser Leu Thr Thr Thr Ser Thr Ala Leu Gly
            915                 920                 925
Lys Leu Gln Asp Val Val Asn Gln Asn Ala Gln Ala Leu Asn Thr Leu
    930                 935                 940
Val Lys Gln Leu Ser Ser Asn Phe Gly Ala Ile Ser Ser Val Leu Asn
945                 950                 955                 960
Asp Ile Leu Ser Arg Leu Asp Lys Val Glu Ala Glu Val Gln Ile Asp
                965                 970                 975
Arg Leu Ile Thr Gly Arg Leu Gln Ser Leu Gln Thr Tyr Val Thr Gln
        980                 985                 990
Gln Leu Ile Arg Ala Ala Glu Ile Arg Ala Ser Ala Asn Leu Ala Ala
            995                 1000                1005
Thr Lys Met Ser Glu Cys Val Leu Gly Gln Ser Lys Arg Val Asp Phe
    1010                1015                1020
Cys Gly Lys Gly Tyr His Leu Met Ser Phe Pro Gln Ala Ala Pro His
1025                1030                1035                1040
Gly Val Val Phe Leu His Val Thr Tyr Val Pro Ser Gln Glu Arg Asn
                1045                1050                1055
Phe Thr Thr Ala Pro Ala Ile Cys His Glu Gly Lys Ala Tyr Phe Pro
        1060                1065                1070
Arg Glu Gly Val Phe Val Phe Asn Gly Thr Ser Trp Phe Ile Thr Gln
            1075                1080                1085
Arg Asn Phe Phe Ser Pro Gln Ile Ile Thr Thr Asp Asn Thr Phe Val
    1090                1095                1100
```

```
Ser Gly Asn Cys Asp Val Val Ile Gly Ile Ile Asn Asn Thr Val Tyr
1105                1110                1115                1120

Asp Pro Leu Gln Pro Glu Leu Asp Ser Phe Lys Glu Leu Asp Lys
            1125                1130                1135

Tyr Phe Lys Asn His Thr Ser Pro Asp Val Asp Leu Gly Asp Ile Ser
            1140                1145                1150

Gly Ile Asn Ala Ser Val Val Asn Ile Gln Glu Glu Ile Asp Arg Leu
    1155                1160                1165

Asn Glu Val Ala Lys Asn Leu Asn Glu Ser Leu Ile Asp Leu Gln Glu
    1170                1175                1180

Leu Gly Lys Tyr Glu Gln Tyr Ile Lys Trp Pro Trp Tyr Val Trp Leu
1185                1190                1195                1200

Gly Phe Ile Ala Gly Leu Ile Ala Ile Val Met Val Thr Ile Leu Leu
            1205                1210                1215

Cys Cys Met Thr Ser Cys Cys Ser Cys Leu Lys Gly Ala Cys Ser Cys
            1220                1225                1230

Gly Ser Cys Cys Lys Phe Asp Glu Asp Asp Ser Glu Pro Val Leu Lys
    1235                1240                1245

Gly Val Lys Leu His Tyr Thr
    1250                1255

<210> SEQ ID NO 95
<211> LENGTH: 250
<212> TYPE: PRT
<213> ORGANISM: SARS coronavirus

<400> SEQUENCE: 95

Ser Gly Ser Asp Leu Asp Arg Cys Thr Thr Phe Asp Asp Val Gln Ala
1               5                   10                  15

Pro Asn Tyr Thr Gln His Thr Ser Ser Met Arg Gly Val Tyr Tyr Pro
            20                  25                  30

Asp Glu Ile Phe Arg Ser Asp Thr Leu Tyr Leu Thr Gln Asp Leu Phe
        35                  40                  45

Leu Pro Phe Tyr Ser Asn Val Thr Gly Phe His Thr Ile Asn His Thr
50                  55                  60

Phe Asp Asp Pro Val Ile Pro Phe Lys Asp Gly Ile Tyr Phe Ala Ala
65                  70                  75                  80

Thr Glu Lys Ser Asn Val Val Arg Gly Trp Val Phe Gly Ser Thr Met
                85                  90                  95

Asn Asn Lys Ser Gln Ser Val Ile Ile Asn Asn Ser Thr Asn Val
            100                 105                 110

Val Ile Arg Ala Cys Asn Phe Glu Leu Cys Asp Asn Pro Phe Phe Val
        115                 120                 125

Val Ser Lys Pro Met Gly Thr Arg Thr His Thr Met Ile Phe Asp Asn
    130                 135                 140

Ala Phe Asn Cys Thr Phe Glu Tyr Ile Ser Asp Ala Phe Ser Leu Asp
145                 150                 155                 160

Val Ser Glu Lys Ser Gly Asn Phe Lys His Leu Arg Glu Phe Val Phe
                165                 170                 175

Lys Asn Lys Asp Gly Phe Leu Tyr Val Tyr Lys Gly Tyr Gln Pro Ile
            180                 185                 190

Asp Val Val Arg Asp Leu Pro Ser Gly Phe Asn Thr Leu Lys Pro Ile
        195                 200                 205

Phe Lys Leu Pro Leu Gly Ile Asn Ile Thr Asn Phe Arg Ala Ile Leu
    210                 215                 220
```

```
Thr Ala Phe Ser Pro Ala Gln Asp Thr Trp Gly Thr Ser Ala Ala Ala
225                 230                 235                 240

Tyr Phe Val Gly Tyr Leu Lys Pro Thr Thr
                245                 250

<210> SEQ ID NO 96
<211> LENGTH: 193
<212> TYPE: PRT
<213> ORGANISM: SARS coronavirus

<400> SEQUENCE: 96

Asn Ile Thr Asn Leu Cys Pro Phe Gly Glu Val Phe Asn Ala Thr Lys
 1               5                  10                  15

Phe Pro Ser Val Tyr Ala Trp Glu Arg Lys Arg Ile Ser Asn Cys Val
                20                  25                  30

Ala Asp Tyr Ser Val Leu Tyr Asn Ser Thr Ser Phe Ser Thr Phe Lys
            35                  40                  45

Cys Tyr Gly Val Ser Ala Thr Lys Leu Asn Asp Leu Cys Phe Ser Asn
        50                  55                  60

Val Tyr Ala Asp Ser Phe Val Val Lys Gly Asp Asp Val Arg Gln Ile
 65                  70                  75                  80

Ala Pro Gly Gln Thr Gly Val Ile Ala Asp Tyr Asn Tyr Lys Leu Pro
                85                  90                  95

Asp Asp Phe Met Gly Cys Val Leu Ala Trp Asn Thr Arg Asn Ile Asp
                100                 105                 110

Ala Thr Ser Thr Gly Asn Tyr Asn Tyr Lys Tyr Arg Tyr Leu Arg His
            115                 120                 125

Gly Lys Leu Arg Pro Phe Glu Arg Asp Ile Ser Asn Val Pro Phe Ser
130                 135                 140

Pro Asp Gly Lys Pro Cys Thr Pro Pro Ala Pro Asn Cys Tyr Trp Pro
145                 150                 155                 160

Leu Asn Gly Tyr Gly Phe Tyr Thr Thr Ser Gly Ile Gly Tyr Gln Pro
                165                 170                 175

Tyr Arg Val Val Val Leu Ser Phe Glu Leu Leu Asn Ala Pro Ala Thr
                180                 185                 190

Val

<210> SEQ ID NO 97
<211> LENGTH: 666
<212> TYPE: PRT
<213> ORGANISM: SARS coronavirus

<400> SEQUENCE: 97

Asp Leu Asp Arg Cys Thr Thr Phe Asp Asp Val Gln Ala Pro Asn Tyr
 1               5                  10                  15

Thr Gln His Thr Ser Ser Met Arg Gly Val Tyr Tyr Pro Asp Glu Ile
                20                  25                  30

Phe Arg Ser Asp Thr Leu Tyr Leu Thr Gln Asp Leu Phe Leu Pro Phe
            35                  40                  45

Tyr Ser Asn Val Thr Gly Phe His Thr Ile Asn His Thr Phe Asp Asp
        50                  55                  60

Pro Val Ile Pro Phe Lys Asp Gly Ile Tyr Phe Ala Ala Thr Glu Lys
 65                  70                  75                  80

Ser Asn Val Val Arg Gly Trp Val Phe Gly Ser Thr Met Asn Asn Lys
                85                  90                  95
```

```
Ser Gln Ser Val Ile Ile Asn Asn Ser Thr Asn Val Val Ile Arg
        100                 105                 110

Ala Cys Asn Phe Glu Leu Cys Asp Asn Pro Phe Phe Val Val Ser Lys
            115                 120                 125

Pro Met Gly Thr Arg Thr His Thr Met Ile Phe Asp Asn Ala Phe Asn
    130                 135                 140

Cys Thr Phe Glu Tyr Ile Ser Asp Ala Phe Ser Leu Asp Val Ser Glu
145                 150                 155                 160

Lys Ser Gly Asn Phe Lys His Leu Arg Glu Phe Val Phe Lys Asn Lys
                165                 170                 175

Asp Gly Phe Leu Tyr Val Tyr Lys Gly Tyr Gln Pro Ile Asp Val Val
            180                 185                 190

Arg Asp Leu Pro Ser Gly Phe Asn Thr Leu Lys Pro Ile Phe Lys Leu
        195                 200                 205

Pro Leu Gly Ile Asn Ile Thr Asn Phe Arg Ala Ile Leu Thr Ala Phe
    210                 215                 220

Ser Pro Ala Gln Asp Thr Trp Gly Thr Ser Ala Ala Ala Tyr Phe Val
225                 230                 235                 240

Gly Tyr Leu Lys Pro Thr Thr Phe Met Leu Lys Tyr Asp Glu Asn Gly
                245                 250                 255

Thr Ile Thr Asp Ala Val Asp Cys Ser Gln Asn Pro Leu Ala Glu Leu
            260                 265                 270

Lys Cys Ser Val Lys Ser Phe Glu Ile Asp Lys Gly Ile Tyr Gln Thr
        275                 280                 285

Ser Asn Phe Arg Val Val Pro Ser Gly Asp Val Val Arg Phe Pro Asn
    290                 295                 300

Ile Thr Asn Leu Cys Pro Phe Gly Glu Val Phe Asn Ala Thr Lys Phe
305                 310                 315                 320

Pro Ser Val Tyr Ala Trp Glu Arg Lys Arg Ile Ser Asn Cys Val Ala
                325                 330                 335

Asp Tyr Ser Val Leu Tyr Asn Ser Thr Ser Phe Ser Thr Phe Lys Cys
            340                 345                 350

Tyr Gly Val Ser Ala Thr Lys Leu Asn Asp Leu Cys Phe Ser Asn Val
        355                 360                 365

Tyr Ala Asp Ser Phe Val Val Lys Gly Asp Asp Val Arg Gln Ile Ala
    370                 375                 380

Pro Gly Gln Thr Gly Val Ile Ala Asp Tyr Asn Tyr Lys Leu Pro Asp
385                 390                 395                 400

Asp Phe Met Gly Cys Val Leu Ala Trp Asn Thr Arg Asn Ile Asp Ala
                405                 410                 415

Thr Ser Thr Gly Asn Tyr Asn Tyr Lys Tyr Arg Tyr Leu Arg His Gly
            420                 425                 430

Lys Leu Arg Pro Phe Glu Arg Asp Ile Ser Asn Val Pro Phe Ser Pro
        435                 440                 445

Asp Gly Lys Pro Cys Thr Pro Pro Ala Pro Asn Cys Tyr Trp Pro Leu
    450                 455                 460

Asn Gly Tyr Gly Phe Tyr Thr Thr Ser Gly Ile Gly Tyr Gln Pro Tyr
465                 470                 475                 480

Arg Val Val Val Leu Ser Phe Glu Leu Leu Asn Ala Pro Ala Thr Val
                485                 490                 495

Cys Gly Pro Lys Leu Ser Thr Asp Leu Ile Lys Asn Gln Cys Val Asn
            500                 505                 510

Phe Asn Phe Asn Gly Leu Thr Gly Thr Gly Val Leu Thr Pro Ser Ser
```

-continued

```
                515                 520                 525
Lys Arg Phe Gln Pro Phe Gln Gln Phe Gly Arg Asp Val Ser Asp Phe
            530                 535                 540

Thr Asp Ser Val Arg Asp Pro Lys Thr Ser Glu Ile Leu Asp Ile Ser
545                 550                 555                 560

Pro Cys Ser Phe Gly Gly Val Ser Val Ile Thr Pro Gly Thr Asn Ala
                565                 570                 575

Ser Ser Glu Val Ala Val Leu Tyr Gln Asp Val Asn Cys Thr Asp Val
            580                 585                 590

Ser Thr Leu Ile His Ala Glu Gln Leu Thr Pro Ala Trp Arg Ile Tyr
            595                 600                 605

Ser Thr Gly Asn Asn Val Phe Gln Thr Gln Ala Gly Cys Leu Ile Gly
            610                 615                 620

Ala Glu His Val Asp Thr Ser Tyr Glu Cys Asp Ile Pro Ile Gly Ala
625                 630                 635                 640

Gly Ile Cys Ala Ser Tyr His Thr Val Ser Ser Leu Arg Ser Thr Ser
                645                 650                 655

Gln Lys Ser Ile Val Ala Tyr Thr Met Ser
            660                 665

<210> SEQ ID NO 98
<211> LENGTH: 575
<212> TYPE: PRT
<213> ORGANISM: SARS coronavirus

<400> SEQUENCE: 98

Leu Gly Ala Asp Ser Ser Ile Ala Tyr Ser Asn Asn Thr Ile Ala Ile
  1               5                  10                  15

Pro Thr Asn Phe Ser Ile Ser Ile Thr Thr Glu Val Met Pro Val Ser
                20                  25                  30

Met Ala Lys Thr Ser Val Asp Cys Asn Met Tyr Ile Cys Gly Asp Ser
            35                  40                  45

Thr Glu Cys Ala Asn Leu Leu Leu Gln Tyr Gly Ser Phe Cys Arg Gln
        50                  55                  60

Leu Asn Arg Ala Leu Ser Gly Ile Ala Ala Glu Gln Asp Arg Asn Thr
 65                  70                  75                  80

Arg Glu Val Phe Val Gln Val Lys Gln Met Tyr Lys Thr Pro Thr Leu
                85                  90                  95

Lys Asp Phe Gly Gly Phe Asn Phe Ser Gln Ile Leu Pro Asp Pro Leu
            100                 105                 110

Lys Pro Thr Lys Arg Ser Phe Ile Glu Asp Leu Leu Phe Asn Lys Val
        115                 120                 125

Thr Leu Ala Asp Ala Gly Phe Met Lys Gln Tyr Gly Glu Cys Leu Gly
130                 135                 140

Asp Ile Asn Ala Arg Asp Leu Ile Cys Ala Gln Lys Phe Asn Gly Leu
145                 150                 155                 160

Thr Val Leu Pro Pro Leu Leu Thr Asp Asp Met Ile Ala Ala Tyr Thr
                165                 170                 175

Ala Ala Leu Val Ser Gly Thr Ala Thr Ala Gly Trp Thr Phe Gly Ala
            180                 185                 190

Gly Ala Ala Leu Gln Ile Pro Phe Ala Met Gln Met Ala Tyr Arg Phe
        195                 200                 205

Asn Gly Ile Gly Val Thr Gln Asn Val Leu Tyr Glu Asn Gln Lys Gln
    210                 215                 220
```

```
Ile Ala Asn Gln Phe Asn Lys Ala Ile Ser Gln Ile Gln Glu Ser Leu
225                 230                 235                 240

Thr Thr Thr Ser Thr Ala Leu Gly Lys Leu Gln Asp Val Val Asn Gln
            245                 250                 255

Asn Ala Gln Ala Leu Asn Thr Leu Val Lys Gln Leu Ser Ser Asn Phe
        260                 265                 270

Gly Ala Ile Ser Ser Val Leu Asn Asp Ile Leu Ser Arg Leu Asp Lys
    275                 280                 285

Val Glu Ala Glu Val Gln Ile Asp Arg Leu Ile Thr Gly Arg Leu Gln
290                 295                 300

Ser Leu Gln Thr Tyr Val Thr Gln Gln Leu Ile Arg Ala Ala Glu Ile
305                 310                 315                 320

Arg Ala Ser Ala Asn Leu Ala Ala Thr Lys Met Ser Glu Cys Val Leu
            325                 330                 335

Gly Gln Ser Lys Arg Val Asp Phe Cys Gly Lys Gly Tyr His Leu Met
        340                 345                 350

Ser Phe Pro Gln Ala Ala Pro His Gly Val Val Phe Leu His Val Thr
    355                 360                 365

Tyr Val Pro Ser Gln Glu Arg Asn Phe Thr Thr Ala Pro Ala Ile Cys
370                 375                 380

His Glu Gly Lys Ala Tyr Phe Pro Arg Glu Gly Val Phe Val Phe Asn
385                 390                 395                 400

Gly Thr Ser Trp Phe Ile Thr Gln Arg Asn Phe Phe Ser Pro Gln Ile
            405                 410                 415

Ile Thr Thr Asp Asn Thr Phe Val Ser Gly Asn Cys Asp Val Val Ile
        420                 425                 430

Gly Ile Ile Asn Asn Thr Val Tyr Asp Pro Leu Gln Pro Glu Leu Asp
    435                 440                 445

Ser Phe Lys Glu Glu Leu Asp Lys Tyr Phe Lys Asn His Thr Ser Pro
450                 455                 460

Asp Val Asp Leu Gly Asp Ile Ser Gly Ile Asn Ala Ser Val Val Asn
465                 470                 475                 480

Ile Gln Glu Glu Ile Asp Arg Leu Asn Glu Val Ala Lys Asn Leu Asn
            485                 490                 495

Glu Ser Leu Ile Asp Leu Gln Glu Leu Gly Lys Tyr Glu Gln Tyr Ile
        500                 505                 510

Lys Trp Pro Trp Tyr Val Trp Leu Gly Phe Ile Ala Gly Leu Ile Ala
    515                 520                 525

Ile Val Met Val Thr Ile Leu Leu Cys Cys Met Thr Ser Cys Cys Ser
530                 535                 540

Cys Leu Lys Gly Ala Cys Ser Cys Gly Ser Cys Cys Lys Phe Asp Glu
545                 550                 555                 560

Asp Asp Ser Glu Pro Val Leu Lys Gly Val Lys Leu His Tyr Thr
            565                 570                 575

<210> SEQ ID NO 99
<211> LENGTH: 33
<212> TYPE: PRT
<213> ORGANISM: Homo sapiens

<400> SEQUENCE: 99

Gly Tyr Thr Phe Thr Ser Tyr Gly Ile Ser Trp Ile Ser Ala Tyr Asn
1               5                   10                  15

Gly Asn Thr Asn Tyr Ala Gln Lys Leu Gln Gly Gly Arg Tyr Leu Asp
            20                  25                  30
```

Tyr

<210> SEQ ID NO 100
<211> LENGTH: 33
<212> TYPE: PRT
<213> ORGANISM: Homo sapiens

<400> SEQUENCE: 100

Gly Tyr Thr Phe Thr Gly Tyr Tyr Met His Trp Ile Asn Pro Asn Ser
1               5                   10                  15

Gly Gly Thr Asn Tyr Ala Gln Lys Phe Gln Gly Gly Thr Tyr Leu Asp
            20                  25                  30

Tyr

<210> SEQ ID NO 101
<211> LENGTH: 33
<212> TYPE: PRT
<213> ORGANISM: Homo sapiens

<400> SEQUENCE: 101

Gly Tyr Thr Phe Thr Gly Tyr Tyr Val His Trp Ile Asn Pro Asn Ser
1               5                   10                  15

Gly Gly Thr Asn Tyr Ala Gln Lys Phe Gln Gly Gly Arg Tyr Leu Asp
            20                  25                  30

Tyr

<210> SEQ ID NO 102
<211> LENGTH: 41
<212> TYPE: PRT
<213> ORGANISM: Homo sapiens

<400> SEQUENCE: 102

Gly Tyr Thr Phe Thr Gly Tyr Tyr Met His Trp Ile Asn Pro Asn Ser
1               5                   10                  15

Gly Gly Thr Asn Tyr Ala Gln Lys Phe Gln Gly Gly Pro His Thr Phe
            20                  25                  30

Gly Ser Gly Ser Tyr Pro Phe Asp Tyr
            35                  40

<210> SEQ ID NO 103
<211> LENGTH: 41
<212> TYPE: PRT
<213> ORGANISM: Homo sapiens

<400> SEQUENCE: 103

Gly Phe Pro Phe Thr Asp Tyr Tyr Met His Trp Ile Asn Ser Asn Ser
1               5                   10                  15

Gly Gly Thr Asn Tyr Ala Gln Lys Phe Gln Gly Gly Pro His Ser Phe
            20                  25                  30

Gly Ser Gly Ser Tyr Pro Phe Asp Tyr
            35                  40

<210> SEQ ID NO 104
<211> LENGTH: 41
<212> TYPE: PRT
<213> ORGANISM: Homo sapiens

<400> SEQUENCE: 104

Gly Tyr Thr Phe Thr Gly Tyr Tyr Met His Trp Ile Asn Ser Asn Ser
1               5                   10                  15

-continued

Gly Gly Thr Asn Tyr Ala Gln Lys Phe Gln Gly Gly Pro His Ser Phe
            20                  25                  30

Gly Ser Gly Ser Tyr Pro Phe Asp Tyr
        35                  40

<210> SEQ ID NO 105
<211> LENGTH: 35
<212> TYPE: PRT
<213> ORGANISM: Homo sapiens

<400> SEQUENCE: 105

Gly Phe Thr Phe Ser Ser Tyr Gly Met His Val Ile Trp Tyr Asp Gly
1               5                   10                  15

Ser Asn Lys Tyr Tyr Ala Asp Ser Val Lys Gly Gly Asp Phe Tyr Trp
            20                  25                  30

Phe Asp Pro
        35

<210> SEQ ID NO 106
<211> LENGTH: 43
<212> TYPE: PRT
<213> ORGANISM: Homo sapiens

<400> SEQUENCE: 106

Gly Phe Thr Phe Ser Ser Tyr Gly Met His Val Ile Trp Tyr Asp Gly
1               5                   10                  15

Ser Asn Lys Tyr Tyr Ala Asp Ser Val Lys Gly Asp Pro Leu Gly Tyr
            20                  25                  30

Cys Ser Ser Thr Ser Cys Ser Tyr Phe Asp Tyr
        35                  40

<210> SEQ ID NO 107
<211> LENGTH: 43
<212> TYPE: PRT
<213> ORGANISM: Homo sapiens

<400> SEQUENCE: 107

Gly Phe Thr Phe Ser Ser Tyr Gly Ile His Val Ile Trp Tyr Asp Gly
1               5                   10                  15

Ser Asn Lys Phe His Ala Asp Ser Val Lys Gly Asp Pro Leu Gly Tyr
            20                  25                  30

Cys Ser Ser Thr Ser Cys Ser Tyr Phe Asp Tyr
        35                  40

<210> SEQ ID NO 108
<211> LENGTH: 43
<212> TYPE: PRT
<213> ORGANISM: Homo sapiens

<400> SEQUENCE: 108

Gly Phe Thr Phe Ser Ser Tyr Gly Ile His Val Ile Trp Tyr Asp Gly
1               5                   10                  15

Ser Asn Lys Phe Tyr Ala Asp Ser Val Lys Gly Asp Pro Leu Gly Tyr
            20                  25                  30

Cys Ser Ser Thr Ser Cys Ser Tyr Phe Asp Tyr
        35                  40

<210> SEQ ID NO 109
<211> LENGTH: 36
<212> TYPE: PRT

<213> ORGANISM: Homo sapiens

<400> SEQUENCE: 109

Gly Phe Thr Phe Ser Ser Tyr Gly Met His Val Ile Trp Tyr Asp Gly
1               5                   10                  15

Ser Asn Lys Tyr Tyr Ala Asp Ser Val Lys Gly Gly Asp Gly Glu
            20                  25                  30

Arg Phe Asp Tyr
        35

<210> SEQ ID NO 110
<211> LENGTH: 42
<212> TYPE: PRT
<213> ORGANISM: Homo sapiens

<400> SEQUENCE: 110

Gly Gly Ser Ile Ser Ser Tyr Tyr Trp Ser Tyr Ile Tyr Tyr Ser Gly
1               5                   10                  15

Ser Thr Asn Tyr Asn Pro Ser Leu Lys Ser Asp Tyr Asp Ile Leu Thr
            20                  25                  30

Gly Tyr Ser Asn Tyr Tyr Gly Met Asp Val
        35                  40

<210> SEQ ID NO 111
<211> LENGTH: 42
<212> TYPE: PRT
<213> ORGANISM: Homo sapiens

<400> SEQUENCE: 111

Asp Gly Ser Ile Ser Ser Phe Tyr Trp Ser Tyr Ile Tyr Tyr Ser Gly
1               5                   10                  15

Ser Thr Asn Tyr Asn Pro Ser Leu Lys Ser Asp Tyr Asp Ile Leu Thr
            20                  25                  30

Gly Tyr Ser Asn Tyr Tyr Gly Met Asp Val
        35                  40

<210> SEQ ID NO 112
<211> LENGTH: 23
<212> TYPE: PRT
<213> ORGANISM: Homo sapiens

<400> SEQUENCE: 112

Arg Ser Ser Gln Ser Leu Val Tyr Ser Asp Gly Asn Thr Tyr Leu Asn
1               5                   10                  15

Lys Val Ser Asn Trp Asp Ser
            20

<210> SEQ ID NO 113
<211> LENGTH: 34
<212> TYPE: PRT
<213> ORGANISM: Homo sapiens

<400> SEQUENCE: 113

Arg Ser Ser Gln Ser Arg Val Tyr Ser Asp Gly Asn Thr Phe Leu Asn
1               5                   10                  15

Lys Val Ser Asn Trp Asp Ser Met Gln Gly Thr His Trp Pro Pro Tyr
            20                  25                  30

Val Gln

<210> SEQ ID NO 114

```
<211> LENGTH: 27
<212> TYPE: PRT
<213> ORGANISM: Homo sapiens

<400> SEQUENCE: 114

Arg Ala Ser Gln Gly Ile Arg Asn Asp Leu Gly Ala Ala Ser Ser Leu
1               5                   10                  15

Gln Ser Leu Gln His Asn Ser Tyr Pro Phe Thr
            20                  25

<210> SEQ ID NO 115
<211> LENGTH: 27
<212> TYPE: PRT
<213> ORGANISM: Homo sapiens

<400> SEQUENCE: 115

Arg Ala Ser Gln Gly Ile Arg Asn Asp Leu Gly Ala Ala Ser Ser Leu
1               5                   10                  15

Gln Ser Leu Gln His Asn Ser Tyr Pro Leu Thr
            20                  25

<210> SEQ ID NO 116
<211> LENGTH: 27
<212> TYPE: PRT
<213> ORGANISM: Homo sapiens

<400> SEQUENCE: 116

Arg Ala Ser Gln Asp Ile Arg Asn Asp Leu Gly Ala Ala Ser Ser Leu
1               5                   10                  15

Gln Ser Leu Gln Tyr Asn Ser Tyr Pro Leu Thr
            20                  25

<210> SEQ ID NO 117
<211> LENGTH: 27
<212> TYPE: PRT
<213> ORGANISM: Homo sapiens

<400> SEQUENCE: 117

Arg Ala Ser Gln Gly Ile Arg Ser Asp Leu Gly Ala Ala Ser Ser Leu
1               5                   10                  15

Gln Ser Gln Gln Tyr Asn Ser Tyr Pro Leu Thr
            20                  25

<210> SEQ ID NO 118
<211> LENGTH: 27
<212> TYPE: PRT
<213> ORGANISM: Homo sapiens

<400> SEQUENCE: 118

Arg Ala Ser Gln Gly Ile Arg Asn Asp Leu Gly Ala Ala Ser Ser Leu
1               5                   10                  15

Gln Ser Leu Gln His Asn Ser Tyr Pro Ile Thr
            20                  25

<210> SEQ ID NO 119
<211> LENGTH: 27
<212> TYPE: PRT
<213> ORGANISM: Homo sapiens

<400> SEQUENCE: 119

Arg Ala Ser Gln Gly Ile Arg Asn Asp Leu Gly Ala Ala Ser Ser Leu
1               5                   10                  15
```

```
Gln Ser Leu Gln Tyr Asn Ser Tyr Pro Ile Thr
            20                  25
```

<210> SEQ ID NO 120
<211> LENGTH: 25
<212> TYPE: PRT
<213> ORGANISM: Homo sapiens

<400> SEQUENCE: 120

```
Arg Ala Ser Gln Gly Ile Ser Ser Trp Leu Ala Ala Ser Ser Leu
 1               5                  10                  15
Gln Ser Gln Gln Ala Asn Ser Phe Thr
            20                  25
```

<210> SEQ ID NO 121
<211> LENGTH: 27
<212> TYPE: PRT
<213> ORGANISM: Homo sapiens

<400> SEQUENCE: 121

```
Arg Ala Ser Gln Gly Ile Ser Asn Trp Leu Ala Ala Ala Ser Ser Leu
 1               5                  10                  15
Gln Ser Gln Gln Ala Asn Asn Phe Pro Leu Thr
            20                  25
```

<210> SEQ ID NO 122
<211> LENGTH: 14
<212> TYPE: PRT
<213> ORGANISM: Homo sapiens

<400> SEQUENCE: 122

```
Gly Pro His Ser Phe Gly Ser Gly Ser Tyr Pro Phe Asp Tyr
 1               5                  10
```

<210> SEQ ID NO 123
<211> LENGTH: 6
<212> TYPE: PRT
<213> ORGANISM: Homo sapiens

<400> SEQUENCE: 123

```
Gly Arg Tyr Leu Asp Tyr
 1               5
```

<210> SEQ ID NO 124
<211> LENGTH: 14
<212> TYPE: PRT
<213> ORGANISM: Homo sapiens

<400> SEQUENCE: 124

```
Gly Pro His Thr Phe Gly Ser Gly Ser Tyr Pro Phe Asp Tyr
 1               5                  10
```

<210> SEQ ID NO 125
<211> LENGTH: 16
<212> TYPE: PRT
<213> ORGANISM: Homo sapiens

<400> SEQUENCE: 125

```
Asp Pro Leu Gly Tyr Cys Ser Ser Thr Ser Cys Ser Tyr Phe Asp Tyr
 1               5                  10                  15
```

<210> SEQ ID NO 126
<211> LENGTH: 16
<212> TYPE: PRT

<213> ORGANISM: Homo sapiens

<400> SEQUENCE: 126

Asp Tyr Asp Ile Leu Thr Gly Tyr Ser Asn Tyr Tyr Gly Met Asp Val
 1               5                   10                  15

<210> SEQ ID NO 127
<211> LENGTH: 9
<212> TYPE: PRT
<213> ORGANISM: Homo sapiens

<400> SEQUENCE: 127

Gly Gly Asp Gly Glu Arg Phe Asp Tyr
 1               5

<210> SEQ ID NO 128
<211> LENGTH: 8
<212> TYPE: PRT
<213> ORGANISM: Homo sapiens

<400> SEQUENCE: 128

Gly Asp Phe Tyr Trp Phe Asp Pro
 1               5

<210> SEQ ID NO 129
<211> LENGTH: 9
<212> TYPE: PRT
<213> ORGANISM: Homo sapiens

<400> SEQUENCE: 129

Gln Gln Tyr Asn Ser Tyr Pro Leu Thr
 1               5

<210> SEQ ID NO 130
<211> LENGTH: 9
<212> TYPE: PRT
<213> ORGANISM: Homo sapiens

<400> SEQUENCE: 130

Leu Gln Tyr Asn Ser Tyr Pro Leu Thr
 1               5

<210> SEQ ID NO 131
<211> LENGTH: 9
<212> TYPE: PRT
<213> ORGANISM: Homo sapiens

<400> SEQUENCE: 131

Leu Gln Tyr Asn Ser Tyr Pro Ile Thr
 1               5

<210> SEQ ID NO 132
<211> LENGTH: 9
<212> TYPE: PRT
<213> ORGANISM: Homo sapiens

<400> SEQUENCE: 132

Gln Gln Ala Asn Asn Phe Pro Leu Thr
 1               5

<210> SEQ ID NO 133
<211> LENGTH: 9
<212> TYPE: PRT
<213> ORGANISM: Homo sapiens

```
-continued

<400> SEQUENCE: 133

Leu Gln His Asn Ser Tyr Pro Phe Thr
  1               5

<210> SEQ ID NO 134
<211> LENGTH: 11
<212> TYPE: PRT
<213> ORGANISM: Homo sapiens

<400> SEQUENCE: 134

Met Gln Gly Thr His Trp Pro Pro Tyr Val Gln
  1               5                  10
```

US 7,728,110 B2

ANTIBODIES TO SARS CORONAVIRUS

CROSS REFERENCE TO RELATED APPLICATIONS

This application claims the benefit of U.S. Provisional Application No. 60/801,951, filed on May 19, 2006, the entire contents of which is incorporated herein by reference.

BACKGROUND OF THE INVENTION

Coronaviruses (CoV) historically are known to cause relatively mild upper respiratory tract infections, and account for approximately 30% of the cases of the common cold in humans. However, a recently identified CoV, severe acute respiratory syndrome coronavirus (SARS-CoV) causes severe respiratory distress in humans leading to mortality in 9.6% of individuals infected (1). In the year 2003, SARS-CoV established efficient human to human transmission resulting in several super-spreading events. By the end of the outbreak in July of 2003, SARS-CoV was responsible for more than 774 deaths and 8096 cases worldwide involving 29 countries (see World Health Organization website, Epidemic and Pandemic Alert and Response, Diseases, SARs). Since the conclusion of the SARS outbreak several reports of confirmed cases of SARS of unknown origin (29, See World Health Organization website) indicate that the environmental threat of SARS-CoV still exists. SARS-CoV-like virus can be isolated from horseshoe bats in China, and researchers postulate that this is the natural reservoir for the virus (18). SARS-CoV-like virus remains present in intermediate wild animal hosts, such as the Himalayan palm civet, raising the possibility of re-emergence of SARS-CoV infection in humans. Because of the remaining threat, it is prudent to develop effective modalities of pre- and post-exposure treatments against SARS-CoV infection.

During the SARS outbreak, isolation measures proved effective in bringing the outbreak under control. In addition, corticosteroids and antiviral treatments, such as ribavirin, were used to treat infected patients although the efficacy of these treatments for SARS has not been established (5). Therefore, a targeted and effective treatment for SARS-CoV remains highly desirable. In humans, SARS-CoV peak viral load is reached by about 10 days post-infection, thus offering an opportunity for effective post-exposure treatment (6). One modality of treatment that may limit virus replication and thus the spread of the virus is passive immunization with pre-formed neutralizing human monoclonal antibodies (mAbs). Such a treatment during the prodromal phase of the disease could aid in rapid clearance of virus and limit poor clinical outcome and person to person spread, without the adverse effects associated with use of corticosteroids, animal sera, or human sera.

SARS-CoV mediates infection of target cells via the spike (S) protein expressed on the surface. SARS-CoV S protein (Genbank accession number: AY525636; nucleotide sequence SEQ ID NO: 93; amino acid sequence SEQ ID NO: 94) is a type one transmembrane glycoprotein divided into two functional domains S1 (amino acids 15-680) and S2 (amino acids 681-1255) (13). The S1 domain mediates the interaction of the S protein with its receptor, angiotensin-converting enzyme 2 (ACE2) (17). A region of S1 consisting of 193 amino acids forms the receptor binding domain (RBD) which is responsible for ACE2 binding (30). More recently, a receptor binding motif (RBM) within the RBD, consisting of 70 amino acids, has been shown to come in direct contact with the tip of ACE2 (16). The S2 domain of the S protein contributes to infection of the target cell by mediating fusion of viral and host membranes through a conformational change in which two conserved helical regions (HR1 and HR2) of the S protein are brought together to form a six-helix bundle fusion core (11).

The S protein serves as the main antigen that elicits protective immune responses, including neutralizing antibodies in infected humans and animals (3, 4, 6, 9, 12, 14). Intranasal or intramuscular application of a modified vaccinia virus Ankara (MVA) expressing S protein into mice elicits SARS-CoV neutralizing antibodies (3). Immunization of mice with a DNA vaccine encoding the S sequence, devoid of the cytoplasmic domain and/or the transmembrane domain, results in the development of neutralizing antibodies as well as both CD4+ and CD8+ T cell responses (31). However, it is not the cellular, but the humoral (IgG) component of immunity that inhibits viral replication (31). In fact, transfer of immune serum from immunized mice to naive mice reduces SARS-CoV titers following viral challenge (25). Together, these studies show that primarily Abs are responsible for protection against SARS-CoV replication, and indicate the potential therapeutic value of passive transfer of neutralizing Abs against SARS-CoV. The immunogenic property of the S protein, including its ability to induce neutralizing antibodies and its essential role in viral attachment and fusion, make it an ideal target for developing effective immunotherapy against SARS-CoV infection.

During an outbreak, the SARS-CoV can mutate and exhibit antigenic variation. In fact sequence analysis indicated that the clinical isolates could be divided into early, middle, and late isolates (27). The significance of this is demonstrated in the ability of later isolates to escape neutralization by a monoclonal antibody that effectively neutralized an earlier isolate (32). Therefore, it is important to produce neutralizing mAbs that are effective against a wide range of clinical isolates with antigenic diversity. Because of the potential evolution of antigenic variants an effective passive therapy against SARS-CoV will likely contain a cocktail of neutralizing Abs that target different epitopes and/or steps in the entry process, such as blocking receptor binding and fusion.

Passive therapy with human immunoglobulin can confer immediate protection without the deleterious effects associated with the use of animal or chimeric Abs containing animal derived amino acid sequences. Accordingly, there remains an urgent need for potent, broad spectrum antibody therapeutics for use in treating SARS-CoV infection.

SUMMARY OF THE INVENTION

In certain aspects, the disclosure provides a neutralizing human monoclonal antibody or antigen-binding portion thereof that specifically binds to a region of human severe acute respiratory syndrome (SARS) Corona Virus (SARS-CoV) Spike (S) protein and blocks S protein binding to a receptor, wherein said region is selected from the group consisting of: amino acid residues 1-1255 (SEQ ID NO: 94), a region that is at least 80% identical to SEQ ID NO: 94, amino acid residues 12-261 (SEQ ID NO: 95), a region that is at least 80% identical to SEQ ID NO: 95, amino acid residues 318-510 (SEQ ID NO: 96), a region that is at least 80% identical to SEQ ID NO: 96, amino acid residues 15-680 (SEQ ID NO: 97), and a region that is at least 80% identical to SEQ ID NO: 97.

In certain embodiments, said antibody or antigen-binding portion binds to the S protein in the region defined by amino acid residues 15-680 (SEQ ID NO: 97). In certain embodiments, said antibody or antigen-binding portion binds to the S protein in a region that is at least 80% identical to SEQ ID NO: 97. In certain embodiments, said antibody or antigen-binding portion binds to the S protein in a region that is at least 85%, 90% or 95% identical to SEQ ID NO: 97. In certain embodiments, said antibody or antigen-binding portion blocks binding of the S protein to angiotensin converting enzyme 2 (Ace2).

In certain embodiments, said antibody or antigen-binding portion binds to the S protein in the region defined by amino acid residues 12-261 (SEQ ID NO: 95). In certain embodiments, said antibody or antigen-binding portion binds to the S protein in a region that is at least 80% identical to SEQ ID NO: 95. In certain embodiments, said antibody or antigen-binding portion binds to the S protein in a region that is at least 85%, 90% or 95% identical to SEQ ID NO: 95. In certain embodiments, said antibody or antigen-binding portion blocks binding of the S protein to angiotensin converting enzyme 2 (Ace2).

In certain embodiments, said antibody or an antigen-binding portion according to any of the preceding embodiments binds to the S protein in the region defined by amino acid residues 318-510 (SEQ ID NO: 96). In certain embodiments, said antibody or antigen-binding portion according to any of the preceding embodiments binds to the S protein in a region that is at least 80% identical to SEQ ID NO: 96. In certain embodiments, said antibody or antigen-binding portion according to any of the preceding embodiments binds to the S protein in a region that is at least 85%, 90% or 95% identical to SEQ ID NO: 96. In certain embodiments, said antibody or antigen-binding portion blocks binding of the S protein to angiotensin converting enzyme 2 (Ace2).

In certain embodiments, said antibody or antigen-binding portion comprises a heavy chain that utilizes a human VH 4-59 gene, a human VH 1-18 gene, a human VH 3-33 gene, or a human VH 1-2 gene. In certain embodiments, said antibody or antigen-binding portion comprises a light chain that utilizes a human VK A30 gene, a human VK L5 gene, or a human VK A1 gene.

In certain aspects, the disclosure provides a human monoclonal antibody or antigen-binding portion that specifically binds to human severe acute respiratory syndrome (SARS) Corona Virus (SARS-CoV) S protein, wherein said antibody or antigen-binding portion neutralizes at least 50% of 200 times the tissue culture infectious dose (200×TCID50) of the virus at an antibody concentration of 12.5 μg/ml or less. In some embodiments, neutralizing antibodies are effective at antibody concentrations of <3.125 μg/ml, <0.8 μg/ml, <0.2 μg/ml, or <0.1 μg/ml.

In certain aspects, the disclosure provides a human monoclonal antibody or antigen-binding portion thereof that specifically binds SARS-CoV S protein comprising VL and VH domains that are at least 80% identical in amino acid sequence to the VL and VH domains, respectively, of a monoclonal antibody selected from the group consisting of: 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2.

In certain aspects, the disclosure provides a human monoclonal antibody or antigen-binding portion thereof that specifically binds SARS-CoV S protein comprising VL and VH domains that are at least 85%. 90% or 95% identical in amino acid sequence to the VL and VH domains, respectively, of a monoclonal antibody selected from the group consisting of: 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2.

In certain aspects, the disclosure provides a human monoclonal antibody or antigen-binding portion thereof that specifically binds SARS-CoV S protein comprising:
(a) a heavy chain variable domain amino acid sequence that comprises the amino acid sequence of the heavy chain variable domain of an antibody selected from: 1B5, 1G3, 2E8:1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2;
(b) a light chain variable domain amino acid sequence that comprises the amino acid sequence of the light chain variable domain of an antibody selected from: 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2;
(c) a heavy chain variable domain of (a) and a light chain variable domain of (b); or
(d) heavy chain and light chain variable domain amino acid sequences comprising the heavy chain and light chain variable domain amino acid sequences, respectively, from the same antibody selected from: 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2.

In certain aspects, the disclosure provides a monoclonal antibody or an antigen-binding portion thereof that specifically binds human SARS-CoV S protein, comprising:
(a) a heavy chain variable domain amino acid sequence that comprises the heavy chain CDR1, CDR2 and CDR3 amino acid sequences of an antibody selected from: 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2;
(b) a light chain variable domain amino acid sequence that comprises the light chain CDR1, CDR2 and CDR3 amino acid sequences of an antibody selected from: 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2;
(c) a heavy chain variable domain of (a) and a light chain variable domain of (b); or
(d) the heavy chain variable domain and light chain variable domain of (c), comprising heavy chain and light chain CDR amino acid sequences from the same antibody selected from: 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2.

In certain aspects, the disclosure provides a monoclonal antibody or an antigen-binding portion thereof that specifically binds SARS-CoV S protein, wherein the antibody comprises FR1, FR2, FR3 and FR4 amino acid sequences from an antibody selected from: 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2.

In certain aspects, the disclosure provides a monoclonal antibody that specifically binds SARS-CoV S protein, wherein said antibody comprises a heavy chain of an antibody selected from the group consisting of: 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2.

In certain aspects, the disclosure provides a monoclonal antibody that specifically binds SARS-CoV S protein, wherein said antibody comprises a light chain of an antibody selected from the group consisting of: 1B5, 1G3, 2E8.1, 2E8.2, 2B10.1, 2B10.2, 22B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2.

In certain aspects, the disclosure provides a monoclonal antibody that specifically binds SARS-CoV S protein, wherein said antibody comprises a heavy chain and a light chain of the same antibody which is selected from the group consisting of: 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2.

In certain aspects, the disclosure provides a composition comprising at least one neutralizing human monoclonal antibody or antigen-binding portion thereof that specifically binds to a region of human SARS-CoV S protein, wherein said region is selected from the group consisting of: amino acid residues 1-1255 (SEQ ID NO: 94), a region that is at least 80% identical to SEQ ID NO: 94, amino acid residues 12-261 (SEQ ID NO: 95), a region that is at least 80% identical to SEQ ID NO: 95, amino acid residues 318-510 (SEQ ID NO: 96), a region that is at least 80% identical to SEQ ID NO: 96, amino acid residues 15-680 (SEQ ID NO: 97), and a region that is at least 80% identical to SEQ ID NO: 97 and a pharmaceutically-acceptable carrier. In certain embodiments, said antibody or antigen-binding portion according to any of the preceding embodiments binds to the S protein in a region that is at least 85%, 90% or 95% identical to SEQ ID NO: 94, 95, 96, or 97.

In certain embodiments, said composition further comprising at least one additional therapeutic agent selected from the group consisting of:
(a) one or more antibodies or an antigen binding portion thereof, wherein said antibody is from the group consisting of: 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5SD1.1, 5D1.2, 5D1.3, 5D1.4, 5D1.5, 5D3, 5D6, 6B1, 6B5, 6B8, 6C1, and 6C2;
(b) one or more antibodies that specifically bind SARS-CoV S protein of a different SARS-CoV strain;
(c) one or more SARS-CoV S protein neutralizing antibodies, wherein said antibodies do not bind SARS-CoV S protein;
(d) one or more agents that bind a SARS-CoV S protein receptor and blocks binding of S protein to the receptor; and
(e) one or more anti-viral agents.

In certain embodiments, at least one additional SARS-CoV neutralizing human monoclonal antibody or antigen-binding portion thereof comprises at least two antibodies that specifically bind to different regions of human SARS-CoV S protein selected from the group consisting of: amino acid residues 1-1255 (SEQ ID NO: 94), a region that is at least 80% identical to SEQ ID NO: 94, amino acid residues 12-261 (SEQ ID NO: 95), a region that is at least 80% identical to SEQ ID NO: 95, amino acid residues 318-510 (SEQ ID NO: 96), a region that is at least 80% identical to SEQ ID NO: 96, amino acid residues 15-680 (SEQ ID NO: 97), and a region that is at least 80% identical to SEQ ID NO: 97. In certain embodiments, said antibody or antigen-binding portion according to any of the preceding embodiments binds to the S protein in a region that is at least 85%, 90% or 95% identical to SEQ ID NO: 94, 95, 96, or 97.

In certain aspects, the disclosure provides an isolated cell line that produces (i) the antibody or antigen-binding portion according to any one of the preceding embodiments; or (ii) the heavy chain or light chain of said antibody or antigen-binding portion.

In certain aspects, the disclosure provides an isolated nucleic acid molecule comprising a nucleotide sequence that encodes the heavy chain or an antigen-binding portion or the light chain or an antigen-binding portion thereof of an antibody according to any one of the preceding embodiments.

In certain aspects, the disclosure provides a vector comprising the nucleic acid molecule according to any one of the preceding embodiments, wherein the vector optionally comprises an expression control sequence operably linked to the nucleic acid molecule.

In certain aspects, the disclosure provides a host cell comprising a vector according to any one of the preceding embodiments or a nucleic acid molecule according to any one of the preceding embodiments.

In certain aspects, the disclosure provides a non-human transgenic animal or transgenic plant comprising the nucleic acid according to any one of the preceding embodiments, wherein the non-human transgenic animal or transgenic plant expresses said nucleic acid. In certain embodiments, said non-human transgenic animal is a mammal.

In certain aspects, the disclosure provides a method for isolating an antibody or antigen-binding portion thereof that specifically binds to human SARS-CoV S protein, comprising the step of isolating the antibody from the non-human transgenic animal or transgenic plant according to any one of the preceding embodiments.

In certain aspects, the disclosure provides a method for producing a human monoclonal antibody according to any one of the preceding embodiments comprising the step of expressing the antibody in a host cell according to any one of the preceding embodiments.

In certain aspects, the disclosure provides a method for decreasing S protein-mediated SARS-CoV binding to cells, the method comprising the step of contacting the S protein with an antibody or antigen-binding portion according to any one of the preceding embodiments. In certain embodiments, said cells express angiotensin converting enzyme 2 (Ace2).

In certain aspects, the disclosure provides a method for decreasing a SARS-CoV S protein-mediated activity, comprising contacting the S protein with an antibody or antigen-binding portion according to any one of the preceding embodiments; or a composition according to any one of the preceding embodiments. In certain embodiments, said SARS-CoV S protein-mediated activity is selected from: viral attachment to a cell, fusing of viral membrane with a cell, or combinations thereof. In certain embodiments, said virus is in a subject.

In certain aspects, the disclosure provides a method for decreasing the SARS-CoV viral load in a subject in need thereof comprising the step of administering an antibody according to any one of the preceding embodiments.

In certain aspects, the disclosure provides a method for treating, preventing or alleviating the symptoms of a SARS-CoV-mediated disorder in a subject in need thereof, comprising the step of administering to said subject an antibody or antigen-binding portion according to any one of the preceding embodiments or a composition according to any one of the preceding embodiments. In certain embodiments, said SARS-CoV-mediated disorder is severe acute respiratory syndrome (SARS).

In certain aspects, the disclosure provides a method for treating, preventing or alleviating the symptoms of a SARS-CoV-mediated disorder in a subject in need thereof, comprising the step of administering to said subject an antibody or antigen-binding portion according to any one of the preceding embodiments, further comprising at least one additional therapeutic agent selected from the group consisting of:

(a) one or more antibodies from the group consisting of: 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2;

(b) one or more antibodies that specifically bind SARS-CoV S protein of a plurality of SARS-CoV strains;

(c) one or more neutralizing antibodies that do not bind SARS-CoV S protein;

(d) one or more agents that bind SARS-CoV S protein receptor; and (e) one or more anti-viral agents.

The invention contemplates combinations of any of the foregoing aspects and embodiments of the invention.

BRIEF DESCRIPTION OF THE DRAWINGS

FIG. 4 shows an alignment of CDR sequences of neutralizing monoclonal antibodies. Immunoglobulin genes of neutralizing antibodies were sequenced. Alignment of the amino acid sequences of the heavy chain variable region (left) and light chain variable region (right) of all human mAbs are depicted and arranged by common gene segment usage. Additions in antibody sequences not contained in germline sequence are annotated (#) in germline sequence.

FIGS. 5A-5F show receptor binding inhibition of neutralizing human anti-SARS-CoV monoclonal antibodies. (a) Group 1A1, (b) Group 1b1, (c) Group 1B2, (d) Group 1B3 and 1B4, (e) Group 1D, and (f) Group 2B. The results of antibodies 3A7, 3F3, and 3C7 of groups 1B1, 2, and 4 respectively are low because recombinant S1 binding in those experiments was unusually low.

DETAILED DESCRIPTION OF THE INVENTION

Definitions and General Techniques

Figure 1A:
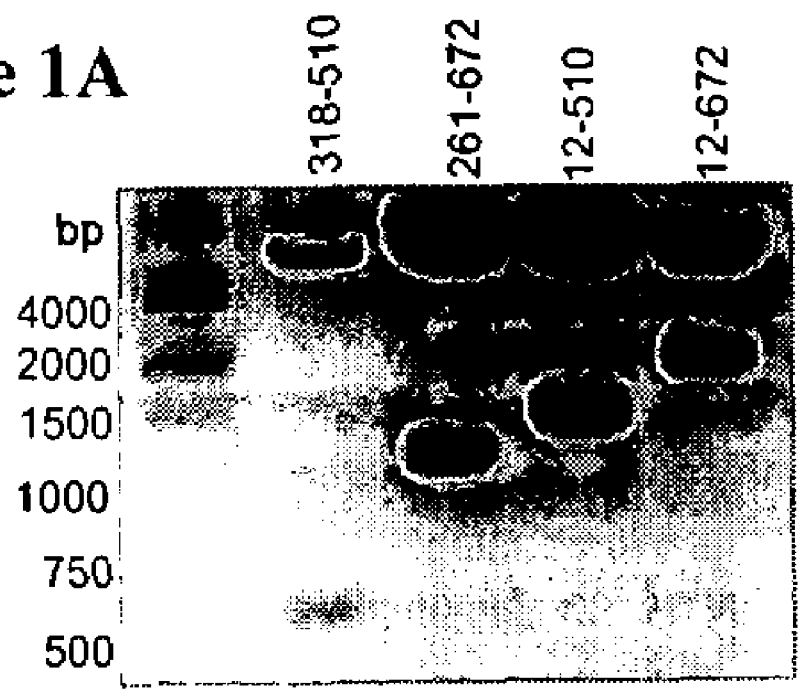
FIGS. 1A-1B show expression of overlapping fragments of the S1 domain of SARS-CoV S protein. (a) Four plasmid constructs encoding different fragments of the S1 protein (12-672, 12-510, 261-672, 318-510) were transformed into MC 1061/P3 cells and insert size confirmed by digestion with Nhe1 and BamH1 and analyzed on a 1% agarose gel. (b) Protein expression in transiently transfected 293T cells was confirmed by Coomassie Blue staining of a 4-20% SDS/PAGE gel.
Figure 1B:
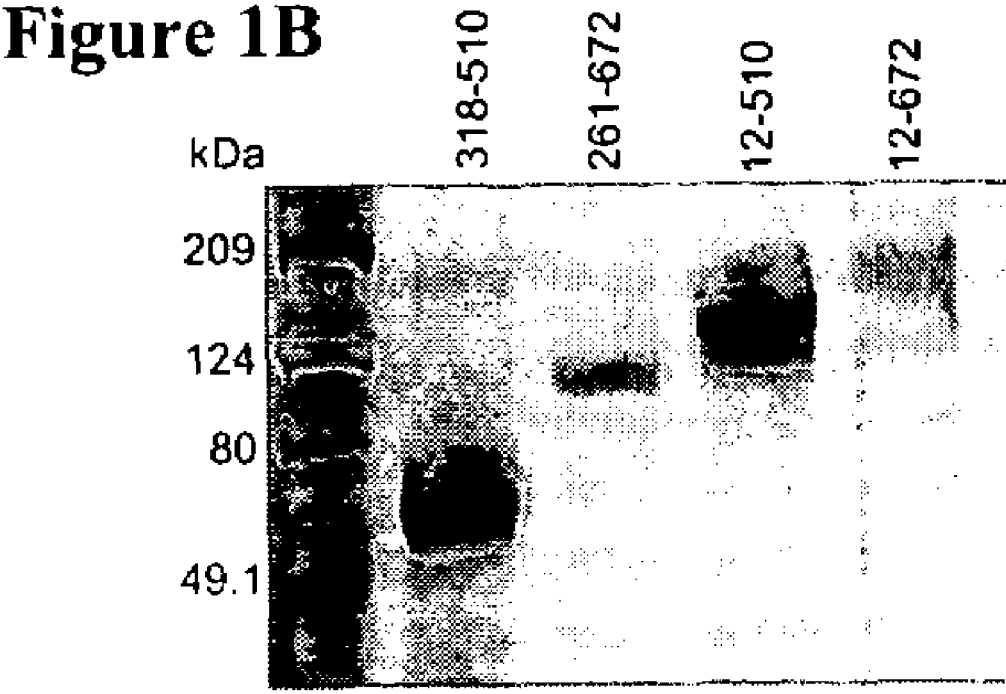

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual*, second ed., Cold Spring Harbor Laboratory Press, Cold Spring Harbor, N.Y. (1989) and Ausubel et al., *Current Protocols in Molecular Biology*,Greene Publishing Associates (1992), and Harlow and Lane *Antibodies: A Laboratory Manual*, Cold Spring Harbor Laboratory Press, Cold Spring Harbor, N.Y. (1990), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

The term "polypeptide" encompasses native or artificial proteins, protein fragments and polypeptide analogs of a protein sequence. A polypeptide may be monomeric or polymeric.

The term "isolated protein", "isolated polypeptide" or "isolated antibody" is a protein, polypeptide or antibody that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally-associated components by isolation, using protein purification techniques well known in the art.

Examples of isolated antibodies include an anti-SARS-CoV S protein antibody that has been affinity purified using SARS-CoV S protein or a portion thereof, an anti-SARS-CoV S protein antibody that has been synthesized by a hybridoma or other cell line in vitro, and a human anti-SARS-CoV S protein antibody derived from a transgenic mouse.

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide fragment" as used herein refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "polypeptide analog" as used herein refers to a polypeptide that comprises a segment that has substantial identity to a portion of an amino acid sequence and that has at least one of the following properties: (1) specific binding to SARS-CoV S protein under suitable binding conditions, (2) ability to inhibit SARS-CoV S protein. Typically, polypeptide analogs comprise a conservative amino acid substitution (or insertion or deletion) with respect to the native sequence. Analogs typically are at least 20 or 25 amino acids long, preferably at least 50, 60, 70, 80, 90, 100, 150 or 200 amino acids long or longer, and can often be as long as a full-length polypeptide. Some embodiments of the invention include polypeptide fragments or polypeptide analog antibodies with 1, 2, 3, 4, 5, 6, 7, 8, 9, 10, 11, 12, 13, 14, 15, 16 or 17 substitutions from the germline amino acid sequence.

In certain embodiments, amino acid substitutions to an anti-SARS-CoV S protein antibody or antigen-binding portion thereof are those which: (1) reduce susceptibility to proteolysis, (2) reduce susceptibility to oxidation, (3) alter binding affinity for forming protein complexes, and (4) confer or modify other physicochemical or functional properties of such analogs, but still retain specific binding to SARS-CoV S protein. Analogs can include various muteins of a sequence other than the normally-occurring peptide sequence. For example, single or multiple amino acid substitutions, preferably conservative amino acid substitutions, may be made in the normally-occurring sequence, preferably in the portion of the polypeptide outside the domain(s) forming intermolecular contacts. A conservative amino acid substitution should not substantially change the structural characteristics of the parent sequence; e.g., a replacement amino acid should not alter the anti-parallel β-sheet that makes up the immunoglobulin binding domain that occurs in the parent sequence, or disrupt other types of secondary structure that characterizes the parent sequence. In general, glycine and proline would not be used in an anti-parallel β-sheet. Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al., *Nature* 354:105 (1991), incorporated herein by reference.

Non-peptide analogs are commonly used in the pharmaceutical industry as drugs with properties analogous to those of the template-peptide. These types of non-peptide compound are termed "peptide mimetics" or "peptidomimetics." Fauchere, *J. Adv. Drug Res.* 15:29 (1986); Veber and Freidinger, *TINS* p.392 (1980); and Evans et al., *J. Med. Chem.* 30:1229 (1987), incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: $—CH_2NH—$, $—CH_2S—$, $—CH_2—CH_2—$, $—CH=CH-$(cis and trans), $—COCH_2—$, $—CH(OH)CH_2—$, and $—CH_2SO—$, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch, *Ann. Rev. Biochem.* 61:387 (1992), incorporated herein by reference); for example, by adding internal cysteine residues capable of forming intramolecular disulfide bridges which cyclize the peptide.

Where an "antibody" is referred to herein with respect to the invention, it is normally understood that an antigen-binding portion thereof may also be used. An antigen-binding portion competes with the intact antibody for specific binding. See generally, *Fundamental Immunology*, Ch. 7 (Paul, W., ed., second ed. Raven Press, N.Y. (1989)) (incorporated by reference in its entirety for all purposes). Antigen-binding portions may be produced by recombinant DNA techniques or by enzymatic or chemical cleavage of intact antibodies. In some embodiments, antigen-binding portions include Fab, Fab', F(ab')$_2$, Fd, Fv, dAb, and complementarity determining region (CDR) fragments, single-chain antibodies (scFv), chimeric antibodies, diabodies and polypeptides that contain at least a portion of an antibody that is sufficient to confer specific antigen binding to the polypeptide.

From N-terminus to C-terminus, both the mature light and heavy chain variable domains comprise the regions FR1, CDR1, FR2, CDR2, FR3, CDR3 and FR4. The assignment of amino acids to each domain herein is in accordance with the definitions of Kabat, *Sequences of Proteins of Immunological Interest* (National Institutes of Health, Bethesda, Md. (1987 and 1991)), Chothia & Lesk, *J. Mol. Biol.* 196:901-917 (1987) or Chothia et al., *Nature* 342:878-883 (1989).

As used herein, an antibody that is referred to by number is the same as a monoclonal antibody that is obtained from the hybridoma of the same number. For example, monoclonal antibody 5C12 is the same antibody as one obtained from hybridoma 5C12, or a subclone thereof.

As used herein, a Fd fragment means an antibody fragment that consists of the $V_H$ and $C_H1$ domains; an Fv fragment consists of the $V_L$ and $V_H$ domains of a single arm of an antibody; and a dAb fragment (Ward et al., *Nature* 341:544-546 (1989)) consists of a $V_H$ domain.

In some embodiments, the antibody is a single-chain antibody (scFv) in which a $V_L$ and $V_H$ domains are paired to form a monovalent molecules via a synthetic linker that enables them to be made as a single protein chain. (Bird et al., *Science* 242:423-426 (1988) and Huston et al., *Proc. Natl. Acad. Sci. USA* 80:5879-5883 (1988).) In some embodiments, the antibodies are diabodies, i.e., are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites. (See e.g., Holliger P. et al., *Proc. Natl. Acad. Sci. USA* 90:6444-6448 (1993), and Poljak R. J. et al., *Structure* 2:1121-1123 (1994).) In some embodiments, one or more CDRs from an antibody of the invention may be incorporated into a molecule either covalently or noncovalently to make it an immunoadhesin that specifically binds to SARS-CoV S protein. In such embodiments, the CDR(s) may be incorporated as part of a larger polypeptide chain, may be covalently linked to another polypeptide chain, or may be incorporated noncovalently.

In embodiments having one or more binding sites, the binding sites may be identical to one another or may be different.

As used herein, the term "human antibody" means any antibody in which the variable and constant domain sequences are human sequences. The term encompasses antibodies with sequences derived from human genes, but which have been changed, e.g. to decrease possible immunogenicity, increase affinity, eliminate cysteines that might cause undesirable folding, etc. The term encompasses such antibodies produced recombinantly in non-human cells, which might impart glycosylation not typical of human cells. These antibodies may be prepared in a variety of ways, as described below.

The term "chimeric antibody" as used herein means an antibody that comprises regions from two or more different antibodies. In one embodiment, one or more of the CDRs of the chimeric antibody are derived from a human anti-SARS-CoV S protein antibody. In another embodiment, all of the CDRs are derived from a human anti-SARS-CoV S protein antibodies. In another embodiment, the CDRs from more than one human anti-SARS-CoV S protein antibodies are combined in a chimeric antibody. For instance, a chimeric antibody may comprise a CDR1 from the light chain of a first human anti-SARS-CoV S protein antibody, a CDR2 from the light chain of a second human anti-SARS-CoV S protein antibody and a CDR3 from the light chain of a third human anti-SARS-CoV S protein antibody, and CDRs from the heavy chain may be derived from one or more other anti-SARS-CoV S protein antibodies. Further, the framework regions may be derived from one of the anti-SARS-CoV S protein antibodies from which one or more of the CDRs are taken or from one or more different human antibodies.

In some embodiments, a chimeric antibody of the invention is a humanized anti-SARS-CoV S protein antibody. A humanized anti-SARS-CoV S protein antibody of the invention comprises the amino acid sequence of one or more framework regions and/or the amino acid sequence from at least a portion of the constant region of one or more human anti-SARS-CoV S protein antibodies of the invention and CDRs derived from a non-human anti-SARS-CoV S protein antibody.

A "neutralizing antibody", an antibody with "neutralizing activity", "antagonistic antibody", or "inhibitory antibody" as used herein means an antibody that neutralizes 200 times the tissue culture infectious dose required to infect 50% of cells (200×TCID$_{50}$) of the SARS-Corona virus. In some embodiments, neutralizing antibodies are effective at antibody concentrations of <12.5 µg/ml, <3.125 µg/ml, <0.8 µg/ml. In preferred embodiments, neutralizing antibodies are effective at antibody concentrations of <0.2 µg/ml. In the most preferred embodiments, neutralizing antibodies are effective at antibody concentrations of <0.1 µg/ml.

Fragments or analogs of antibodies or immunoglobulin molecules can be readily prepared by those of ordinary skill in the art following the teachings of this specification.

Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. See Bowie et al., *Science* 253:164 (1991).

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.). For further descriptions, see Jonsson U. et al., *Ann. Biol. Clin.* 51:19-26 (1993); Jonsson U. et al., *Biotechniques* 11:620-627 (1991); Jonsson B. et al., *J. Mol. Recognit.* 8:125-131 (1995); and Johnsson B. et al., *Anal. Biochem.* 198:268-277 (1991).

The term "TCID$_{50}$" refers to the amount of virus necessary to infect 50% of cells in tissue culture. The 100× and 200× refer to 100 or 200 times the concentration of virus compared to the TCID$_{50}$.

The term "$K_D$" refers to the equilibrium dissociation constant of a particular antibody-antigen interaction.

The term "epitope" includes any protein determinant capable of specific binding to an immunoglobulin or T-cell receptor or otherwise interacting with a molecule. Epitopic determinants generally consist of chemically-active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. An antibody is said to specifically bind an antigen when the dissociation constant is ≦1 mM, preferably ≦100 nM and most preferably ≦10 nM. In certain embodiments, the $K_D$ is 1 pM to 500 pM. In other embodiments, the $K_D$ is between 500 pM to 1 μM. In other embodiments, the $K_D$ is between 1 μM to 100 nM. In other embodiments, the $K_D$ is between 100 mM to 10 nM. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen. A high throughput process for "binning" antibodies based upon their cross-competition is described in International Patent Application No. WO 03/48731.

As used herein, the twenty conventional amino acids and their abbreviations follow conventional usage. See *Immunology—A Synthesis* (second Edition, E. S. Golub and D. R. Gren, Eds., Sinauer Associates, Sunderland, Mass. (1991)), incorporated herein by reference.

The term "polynucleotide" as referred to herein means a polymeric form of nucleotides of at least 10 bases in length, either ribonucleotides or deoxynucleotides or a modified form of either type of nucleotide. The term includes single and double stranded forms.

The term "isolated polynucleotide" as used herein means a polynucleotide of genomic, cDNA, or synthetic origin or some combination thereof, which by virtue of its origin the "isolated polynucleotide" (1) is not associated with all or a portion of a polynucleotides with which the "isolated polynucleotide" is found in nature, (2) is operably linked to a polynucleotide to which it is not linked in nature, or (3) does not occur in nature as part of a larger sequence.

The term "naturally occurring nucleotides" as used herein includes deoxyribonucleotides and ribonucleotides. The term "modified nucleotides" as used herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al., *Nucl. Acids Res.* 14:9081 (1986); Stec et al, *J. Am. Chem. Soc.* 106:6077 (1984); Stein et al., *Nucl. Acids Res.* 16:3209 (1988); Zon et al., *Anti-Cancer Drug Design* 6:539 (1991); Zon et al., *Oligonucleotides and Analogues: A Practical Approach*, pp. 87-108 (F. Eckstein, Ed., Oxford University Press, Oxford England (1991)); U.S. Pat. No. 5,151,510; Uhlmann and Peyman, *Chemical Reviews* 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest. The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. One example of "high stringency" or "highly stringent" conditions is the incubation of a polynucleotide with another polynucleotide, wherein one polynucleotide may be affixed to a solid surface such as a membrane, in a hybridization buffer of 6×SSPE or SSC, 50% formamide, 5× Denhardt's reagent, 0.5% SDS, 100 μg/ml denatured, fragmented salmon sperm DNA at a hybridization temperature of 42° C. for 12-16 hours, followed by twice washing at 55° C. using a wash buffer of 1×SSC, 0.5% SDS. See also Sambrook et al., supra, pp. 9.50-9.55.

The term "percent sequence identity" in the context of nucleotide sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183:63-98 (1990); Pearson, *Methods Mol. Biol.* 132:180-219 (2000); Pearson, *Methods Enzymol.* 266:227-258 (1996); Pearson, *J. Mol. Biol.* 276:71-84 (1998); incorporated herein by reference). Unless otherwise specified, default parameters for a particular program or algorithm are used. For instance, percent sequence identity between nucleotide sequences can be determined using FASTA with its default parameters (a word size of 6 and the NOPAM factor for the scoring matrix) or using Gap with its default parameters as provided in GCG Version 6.1, incorporated herein by reference.

A reference to a nucleotide sequence encompasses its complement unless otherwise specified. Thus, a reference to a nucleic acid having a particular sequence should be understood to encompass its complementary strand, with its complementary sequence.

As used herein, the terms "percent sequence identity" and "percent sequence homology" are used interchangeably.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 80%, at least about 90%, at least about 95%, 96%, 97%, 98% or 99% of the nucleotide bases, as measured by any well-known algorithm of sequence identity, such as FASTA, BLAST or Gap, as discussed above.

As applied to polypeptides, the term "substantial identity" means that two peptide sequences, when optimally aligned, such as by the programs GAP or BESTFIT using default gap weights as supplied with the programs, share at least 70%, 75% or 80% sequence identity, at least 90% or 95% sequence identity, or at least 97%, 98% or 99% sequence identity. In certain embodiments, residue positions that are not identical differ by conservative amino acid substitutions. A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity may be adjusted upwards to correct for the conservative nature of the substitution. Means for making this adjustment are well-known to those of skill in the art. See, e.g., Pearson, *Methods Mol. Biol.* 243: 307-31 (1994). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine.

Conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science* 256:1443-45 (1992), incorporated herein by reference. A "moderately conservative" replacement is any change having a nonnegative value in the PAM250 log-likelihood matrix.

Sequence identity for polypeptides is typically measured using sequence analysis software. Protein analysis software matches sequences using measures of similarity assigned to various substitutions, deletions and other modifications, including conservative amino acid substitutions. For instance, GCG contains programs such as "Gap" and "Bestfit" which can be used with default parameters as specified by the programs to determine sequence homology or sequence identity between closely related polypeptides, such as homologous polypeptides from different species of organisms or between a wild type protein and a mutein thereof. See, e.g., GCG Version 6.1 (University of Wisconsin, WI). Polypeptide sequences also can be compared using FASTA using default or recommended parameters, see GCG Version 6.1. FASTA (e.g., FASTA2 and FASTA3) provides alignments and percent sequence identity of the regions of the best overlap between the query and search sequences (Pearson, *Methods Enzymol.* 183:63-98 (1990); Pearson, *Methods Mol. Biol.* 132:180-219 (2000)). Another preferred algorithm when comparing a sequence of the invention to a database containing a large number of sequences from different organisms is the computer program BLAST, especially blastp or tblastn, using default parameters as supplied with the programs. See, e.g., Altschul et al., *J. Mol. Biol.* 215:403-410 (1990); Altschul et al., *Nucleic Acids Res.* 25:3389-402 (1997).

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, the labels for polypeptides include fluorophore. The term "fluorophore" refers to compounds with a fluorescent emission maximum between about 400 and 900 nm. In some embodiments, labels are attached by spacer arms of various lengths to reduce potential steric hindrance.

Throughout this specification and claims, the word "comprise," or variations such as "comprises" or "comprising," will be understood to imply the inclusion of a stated integer or group of integers but not the exclusion of any other integer or group of integers.

Human Anti-SARS-CoV S Protein Antibodies and Characterization Thereof

In one embodiment, the invention provides humanized anti-SARS-CoV S protein antibodies. In another embodiment, the invention provides human anti-SARS-CoV S protein antibodies. In some embodiments, human anti-SARS-CoV S protein antibodies are produced by immunizing a non-human transgenic animal, e.g., a rodent, whose genome comprises human immunoglobulin genes so that the transgenic animal produces human antibodies. In some embodiments, the anti-SARS-CoV S protein antibodies and antigen-binding portions include, but are not limited to, antibodies or antigen-binding portions which bind to (i) the S1 domain of SARS-CoV S protein; (ii) the S2 domain of SARS-CoV S protein; or (iii) both (i) and (ii).

An anti-SARS-CoV S protein antibody of the invention can comprise a human kappa or a human lambda light chain or an amino acid sequence derived therefrom. In some embodiments comprising a kappa light chain, the light chain variable domain ($V_L$) is encoded in part by a human $V_K1$ or $V_K2$ family gene. In certain embodiments, the light chain utilizes a human Vκ A30, a human Vκ L5 or a human Vκ A1 gene.

In some embodiments, the $V_L$ of the SARS-CoV S protein antibody comprises one or more amino acid substitutions relative to the germline amino acid sequence of the human gene. In some embodiments, the $V_L$ of the anti-SARS-CoV S protein antibody comprises 1, 2, 3, 4, 5, 6, 7, 8, 9, or 10 amino acid substitutions relative to the germline amino acid sequence. In some embodiments, one or more of those substitutions from germline is in the CDR regions of the light chain. In some embodiments, the amino acid substitutions relative to germline are at one or more of the same positions as the substitutions relative to germline in any one or more of the $V_L$ of antibodies 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2. For example, the $V_L$ of an anti-SARS-CoV S protein antibody of the invention may contain one or more amino acid substitutions compared to germline found in the $V_L$ of antibody 4E2. In some embodiments, the amino acid changes are at one or more of the same positions, but involve a different substitution than in the reference antibody.

In some embodiments, amino acid changes relative to germline occur at one or more of the same positions as in any of the $V_L$ of antibodies 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2, but the changes may represent conservative amino acid substitutions at such position(s) relative to the amino acid in the reference antibody. For example, if a particular position in one of these antibodies is changed relative to germline and is glutamate, one may substitute aspartate at that position. Similarly, if an amino acid substitution compared to germline is serine, one may conservatively substitute threonine for serine at that position. Conservative amino acid substitutions are discussed supra.

In some embodiments, the light chain of the human anti-SARS-CoV S protein antibody comprises the $V_L$ amino acid sequence of monoclonal antibody 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2 or said amino acid sequence having up to 1, 2, 3, 4, 5, 6, 7, 8, 9, or 10 conservative amino acid substitutions and/or a total of up to 3 non-conservative amino acid substitutions. In some embodiments, the light chain comprises the amino acid sequence from the beginning of the CDR1 to the end of the CDR3 of any one of the foregoing antibodies.

In some embodiments, the light chain may comprise CDR1, CDR2 and CDR3 regions independently selected from the light chain CDR1, CDR2 and CDR3, respectively, of the light chain of monoclonal antibody 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2, or CDR regions each having less than 4 or less than 3 conservative amino acid substitutions and/or a total of three or fewer non-conservative amino acid substitutions. In some embodiments, the light chain of the anti-SARS-CoV S protein antibody comprises a light chain CDR1, CDR2, and CDR3, each of which are independently selected from the light chain CDR1, CDR2 and CDR3 regions of monoclonal antibody 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1., 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2. In certain embodiments, the light chain of the anti-SARS-CoV S protein antibody comprises the light chain CDR1, CDR2 and CDR3 regions of an antibody comprising the amino acid sequence of the $V_L$ region of an antibody selected from 1B5, 1G3, 2E8.1, 2E8.2, 2B10.1, 2B10.2, 2B10.3, 2B10.4, 3A7, 3C7, 3F3, 3H12, 4E2, 4A10, 4.1, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2 or said CDR regions each having less than 4 or less than 3 conservative amino acid substitutions and/or a total of three or fewer non-conservative amino acid substitutions.

With regard to the heavy chain, in some embodiments, the variable domain ($V_H$) is encoded in part by a human $V_H1$, $V_H3$ or $V_H4$ family gene. In certain embodiments, the heavy chain utilizes a human $V_H$ 1-2, $V_H$ 1-18, $V_H$ 3-33 or $V_H$ 4-49 gene. In some embodiments, the $V_H$ sequence of the anti-SARS-CoV S protein antibody contains one or more amino acid substitutions, deletions or insertions (additions) relative to the germline amino acid sequence. In some embodiments, the variable domain of the heavy chain comprises 1, 2, 3, 4, 5, 6, 7, 8, 9, 10, 11, 12, 13, 14, 15, 16, or 17 mutations from the germline amino acid sequence. In some embodiments, the mutation(s) are non-conservative substitutions compared to the germline amino acid sequence. In some embodiments, the mutations are in the CDR regions of the heavy chain. In some embodiments, the amino acid changes are made at one or more of the same positions as the mutations from germline in any one or more of the $V_H$ of antibodies 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2. In other embodiments, the amino acid changes are at one or more of the same positions but involve a different mutation than in the reference antibody.

In some embodiments, the heavy chain comprises the $V_H$ amino acid sequence of monoclonal antibody; 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2 or said $V_H$ amino acid sequence having up to 1, 2, 3, 4, 6, 8, or 10 conservative amino acid substitutions and/or a total of up to 3 non-conservative amino acid substitutions. In some embodiments, the heavy chain comprises the amino acid sequence from the beginning of the CDR1 to the end of the CDR3 of any one of the foregoing antibodies.

In some embodiments, the heavy chain comprises the heavy chain CDR1, CDR2 and CDR3 regions of monoclonal antibody 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2 or said CDR regions each having less than 8, less than 6, less than 4, or less than 3 conservative amino acid substitutions and/or a total of three or fewer non-conservative amino acid substitutions.

In some embodiments, the heavy chain CDR regions are independently selected from the CDR regions of monoclonal antibodies 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2. In another embodiment, the antibody comprises a light chain as disclosed above and a heavy chain as disclosed above. In a further embodiment, the light chain CDRs and the heavy chain CDRs are from the same antibody.

One type of amino acid substitution that may be made is to change one or more cysteines in the antibody, which may be chemically reactive, to another residue, such as, without limitation, alanine or serine. In one embodiment, there is a substitution of a non-canonical cysteine. The substitution can be made in a CDR or framework region of a variable domain or in the constant domain of an antibody. In some embodiments, the cysteine is canonical.

Another type of amino acid substitution that may be made is to change any potential proteolytic sites in the antibody. Such sites may occur in a CDR or framework region of a variable domain or in the constant domain of an antibody. Substitution of cysteine residues and removal of proteolytic sites may decrease the risk of any heterogeneity in the antibody product and thus increase its homogeneity. Another type of amino acid substitution is to eliminate asparagine-glycine pairs, which form potential deamidation sites, by altering one or both of the residues.

In some embodiments, the C-terminal lysine of the heavy chain of the anti SARS-CoV S protein antibody of the invention is cleaved. In various embodiments of the invention, the heavy and light chains of the anti-SARS-CoV S protein antibodies may optionally include a signal sequence.

In one aspect, the invention relates to nineteen inhibitory human anti-SARS-CoV S protein monoclonal antibodies and the hybridoma cell lines that produce them, 4E2, 4G2, 6C1, 3A7, 5A7, 5D3, 5D6, 6B8, 4A10, 6C2, 3F3, 5A5, 6B5, 5E4, 3C7, 6B1, 3H12, 4D4 or 1B5. The nucleic acids encoding the full-length, or variable domain-comprising portions, of heavy and light chains, and the corresponding deduced amino acid sequences can be found in the sequence listing.

The invention further provides heavy and/or light chain variants of certain of the above-listed human anti-SARS-CoV S protein antibodies, comprising one or more amino acid substitutions. In still further embodiments, the invention includes antibodies comprising variable domain amino acid sequences with more than 80%, more than 85%, more than 90%, more than 95%, more than 96%, more than 97%, more than 98% or more than 99% sequence identity to an variable domain amino acid sequence of any of the above-listed human anti-SARS-CoV S protein antibodies.

Class and Subclass of Anti-SARS-CoV S Protein Antibodies

The class and subclass of anti-SARS-CoV S protein antibodies may be determined by any method known in the art. In general, the class and subclass of an antibody may be determined using antibodies that are specific for a particular class and subclass of antibody. Such antibodies are commercially available. The class and subclass can be determined by ELISA, or Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

In some embodiments, the anti-SARS-CoV S protein antibody is a monoclonal antibody. The anti-SARS-CoV S protein antibody can be an IgG, an IgM, an IgE, an IgA, or an IgD molecule. In one embodiment, the anti-SARS-CoV S protein antibody is an IgG and is an IgG1, IgG2, IgG3, IgG4 subclass. In still another embodiment, the antibody is subclass IgG1.

Binding Affinity of Anti-SARS-CoV S Protein Antibodies to SARS-CoV S Protein

In some embodiments of the invention, the anti-SARS-CoV S protein antibodies bind to SARS-CoV S protein with high affinity.

In some embodiments, the anti-SARS-CoV S protein antibodies bind with high affinity to the S1 domain of SARS-CoV S protein.

In some embodiments, the anti-SARS-CoV S protein antibodies bind to the S2 domain of SARS-CoV S protein.

In another embodiment, the anti-SARS-CoV S protein antibody binds to SARS-CoV S protein.

The binding affinity and dissociation rate of an anti-SARS-CoV S protein antibody to SARS-CoV S protein can be determined by methods known in the art. The binding affinity can be measured by ELISAs, RIAs, flow cytometry, surface plasmon resonance, such as BIACORE™. The dissociate rate can be measured by surface plasmon resonance. Preferably, the binding affinity and dissociation rate is measured by surface plasmon resonance. More preferably, the binding affinity and dissociation rate are measured using BIACORE™. One can determine whether an antibody has substantially the same $K_D$ as an anti-SARS-CoV S protein antibody by using methods known in the art. Example V exemplifies a method for determining affinity constants of anti-SARS-CoV S protein monoclonal antibodies.

Identification of SARS-CoV S Protein Epitopes Recognized by Anti-SARS-CoV S Protein Antibodies The invention provides a human anti-SARS-CoV S protein monoclonal antibody that binds to SARS-CoV S protein and competes or cross-competes with and/or binds the same epitope as an antibody selected from 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2; If two antibodies reciprocally compete with each other for binding to SARS-CoV S protein, they are said to cross-compete.

One can determine whether an antibody binds to the same epitope or cross competes for binding with an anti-SARS-CoV S protein antibody by using methods known in the art. In one embodiment, one allows the anti-SARS-CoV S protein antibody of the invention to bind to SARS-CoV S protein under saturating conditions and then measures the ability of the test antibody to bind to SARS-CoV S protein. If the test antibody is able to bind to SARS-CoV S protein at the same time as the anti-SARS-CoV S protein antibody, then the test antibody binds to a different epitope as the anti-SARS-CoV S protein antibody. However, if the test antibody is not able to bind to SARS-CoV S protein at the same time, then the test antibody binds to the same epitope, an overlapping epitope, or an epitope that is in close proximity to the epitope bound by the human anti-SARS-CoV S protein antibody. This experiment can be performed using ELISA, RIA, BIACORE™, or flow cytometry.

To test whether an anti-SARS-CoV S protein antibody cross-competes with another anti-SARS-CoV S protein antibody, one may use the competition method described above in two directions i.e. determining if the reference antibody blocks the test antibody and vice versa. In one embodiment, the experiment is performed using ELISA. Methods of determining $K_D$ are discussed further below.

Inhibition of SARS-CoV S Protein Activity by Anti-SARS-CoV S Protein Antibody

In another embodiment, the invention provides an anti-SARS-CoV S protein antibody that inhibits, blocks, or decreases SARS-CoV S protein binding to a receptor, in particular, to angiotensin-converting enzyme 2 (ACE2). In another embodiment, the invention provides an anti-SARS-CoV S protein antibody that inhibits, blocks, or decreases SARS-CoV S protein-mediated viral entry into cells. In another embodiment, the invention provides an anti-SARS-CoV S protein antibody that inhibits, blocks, or decreases fusion of viral and cell membranes. In another embodiment, the invention provides an anti-SARS-CoV S protein antibody that decreases viral load. In another embodiment, the invention provides an anti-SARS-CoV S protein antibody that inhibits, blocks, or decreases in severity for any period of time symptoms or conditions resulting from SARS-CoV infection. In certain embodiments, the invention provides an anti-SARS-CoV S protein antibody that inhibits, blocks, or decreases in severity for a day, a week, a month, 6 months, a year, or for the remainder of the subjects life symptoms or conditions resulting from SARS-CoV infection by 25, 30, 35, 40, 45, 50, 55, 60, 65, 70, 75, 80, 85, 90, 95, or 100%. In certain embodiments, the invention provides an anti-SARS-CoV S protein antibody that may perform any combination of the preceding embodiments.

Methods of Producing Antibodies and Antibody Producing Cell Lines

Immunization

In some embodiments, human antibodies are produced by immunizing a non-human, transgenic animal comprising within its genome some or all of human immunoglobulin heavy chain and light chain loci with a SARS-CoV S protein antigen. In one embodiment, the non-human animal is a XENOMOUSE™ animal. (Abgenix, Inc., Fremont, Calif.).

XENOMOUSE™ mice are engineered mouse strains that comprise large fragments of human immunoglobulin heavy chain and light chain loci and are deficient in mouse antibody production. See, e.g., Green et al., *Nature Genetics* 7:13-21 (1994) and U.S. Pat. Nos. 5,916,771, 5,939,598, 5,980,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504.

In another aspect, the invention provides a method for making anti-SARS-CoV S protein antibodies from non-human, non-mouse animals by immunizing non-human transgenic animals that comprise human immunoglobulin loci with a SARS-CoV S protein antigen. One can produce such animals using the methods described in the above-cited documents. The methods disclosed in these documents can be modified as described in U.S. Pat. No. 5,994,619, which is hereby incorporated by reference. U.S. Pat. No. 5,994,619 describes methods for producing novel cultured inner cell mass (CICM) cells and cell lines, derived from pigs and cows, and transgenic CICM cells into which heterologous DNA has been inserted. CICM transgenic cells can be used to produce cloned transgenic embryos, fetuses, and offspring. The '619 patent also describes methods of producing transgenic animals that are capable of transmitting the heterologous DNA to their progeny. In preferred embodiments of the current invention, the non-human animals are mammals, particularly rats, sheep, pigs, goats, cattle or horses.

XENOMOUSE™ mice produce an adult-like human repertoire of fully human antibodies and generate antigen-specific human antibodies. In some embodiments, the XENOMOUSE™ mice contain approximately 80% of the human antibody V gene repertoire through introduction of megabase sized, germline configuration fragments of the human heavy chain loci and kappa light chain loci in yeast artificial chromosome (YAC). In other embodiments, XENOMOUSE™ mice further contain approximately all of the human lambda light chain locus. See Mendez et al., *Nature Genetics* 15:146-156 (1997), Green and Jakobovits, *J. Exp. Med.* 188:483-495 (1998), and WO 98/24893, the disclosures of which are hereby incorporated by reference.

In some embodiments, the non-human animal comprising human immunoglobulin genes are animals that have a human immunoglobulin "minilocus". In the minilocus approach, an exogenous Ig locus is mimicked through the inclusion of individual genes from the Ig locus. Thus, one or more $V_H$ genes, one or more $D_H$ genes, one or more $J_H$ genes, a mu constant domain, and a second constant domain (preferably a gamma constant domain) are formed into a construct for insertion into an animal. This approach is described, inter alia, in U.S. Pat. Nos. 5,545,807, 5,545,806, 5,569,825, 5,625,126, 5,633,425, 5,661,016, 5,770,429, 5,789,650, 5,814,318, 5,591,669, 5,612,205, 5,721,367, 5,789,215, and 5,643,763, hereby incorporated by reference.

In another aspect, the invention provides a method for making humanized anti-SARS-CoV S protein antibodies. In some embodiments, non-human animals are immunized with a SARS-CoV S protein antigen as described below under conditions that permit antibody production. Antibody-producing cells are isolated from the animals, fused with myelomas to produce hybridomas, and nucleic acids encoding the heavy and light chains of an anti-SARS-CoV S protein antibody of interest are isolated. These nucleic acids are subsequently engineered using techniques known to those of skill in the art and as described further below to reduce the amount of non-human sequence, i.e., to humanize the antibody to reduce the immune response in humans In some embodiments, the SARS-CoV S protein antigen is isolated and/or purified SARS-CoV S protein or an antigenic portion thereof, for example, the ectodomain. In some embodiments, the SARS-CoV S protein antigen is a fragment of SARS-CoV S protein. In some embodiments, the SARS-CoV S protein fragment is the S1 domain of SARS-CoV S protein. In some embodiments, the SARS-CoV S protein fragment is the S2 domain of SARS-CoV S protein. In certain embodiments, the SARS-CoV S protein fragment comprises the S1 or S2 domain of SARS-CoV S protein. In some embodiments, the SARS-CoV S protein fragment comprises at least one epitope of SARS-CoV S protein. In other embodiments, the SARS-CoV S protein antigen is a cell that expresses or overexpresses SARS-CoV S protein or an immunogenic fragment thereof on its surface. In some embodiments, the SARS-CoV S protein antigen is a SARS-CoV S protein fusion protein. In some embodiments, the SARS-CoV S protein is a synthetic peptide immunogen.

Immunization of animals can be by any method known in the art. See, e.g., Harlow and Lane, *Antibodies: A Laboratory Manual*, New York: Cold Spring Harbor Press, 1990. Methods for immunizing non-human animals such as mice, rats, sheep, goats, pigs, cattle and horses are well known in the art. See, e.g., Harlow and Lane, supra, and U.S. Pat. No. 5,994, 619. In one embodiment, the SARS-CoV S protein antigen is administered with an adjuvant to stimulate the immune response. Exemplary adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks. Example I exemplifies a method for producing anti-SARS-CoV S protein monoclonal antibodies in XENOMOUSE™ mice.

Production of Antibodies and Antibody-Producing Cell Lines

After immunization of an animal with a SARS-CoV S protein antigen, antibodies and/or antibody-producing cells can be obtained from the animal. In some embodiments, anti-SARS-CoV S protein antibody-containing serum is obtained from the animal by bleeding or sacrificing the animal. The serum may be used as it is obtained from the animal, an immunoglobulin fraction may be obtained from the serum, or the anti-SARS-CoV S protein antibodies may be purified from the serum.

In some embodiments, antibody-producing immortalized cell lines are prepared from cells isolated from the immunized animal. After immunization, the animal is sacrificed and lymph node and/or splenic B cells are immortalized by any means known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Immortalized cells are screened using SARS-CoV S protein, a portion thereof, or a cell expressing SARS-CoV S protein. In one embodiment, the initial screening is performed using an enzyme-linked immunoassay (ELISA) or a radioimmunoassay. An example of ELISA screening is provided in WO 00/37504, incorporated herein by reference.

Anti-SARS-CoV S protein antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

In one embodiment, the immunized animal is a non-human animal that expresses human immunoglobulin genes and the splenic B cells are fused to a myeloma cell line from the same species as the non-human animal. In a more preferred embodiment, the immunized animal is a XENOMOUSE™ mouse and the myeloma cell line is a non-secretory mouse myeloma. In an even more preferred embodiment, the myeloma cell line is P3-X63-Ag8.653 (American Type Culture Collection. See, e.g., Example I.

Thus, in one embodiment, the invention provides methods for producing a cell line that produces a human monoclonal antibody or a fragment thereof directed to SARS-CoV S protein comprising (a) immunizing a non-human transgenic animal described herein with SARS-CoV S protein, a portion of SARS-CoV S protein or a cell or tissue expressing SARS-CoV S protein; (b) allowing the transgenic animal to mount an immune response to SARS-CoV S protein; (c) isolating antibody-producing cells from the transgenic animal; (d) immortalizing the antibody-producing cells; (e) creating individual monoclonal populations of the immortalized antibody-producing cells; and (f) screening the immortalized antibody-producing cells to identify an antibody directed to SARS-CoV S protein. In one embodiment, step (f) comprises screening the immortalized antibody-producing cells to identify an antibody directed to the S1 domain of SARS-CoV S protein; the S2 domain of SARS-CoV S protein; or (iii) both (i) and (ii).

Where it is desired to identify a monoclonal antibody directed to the S1 or S2 domains of SARS-CoV S protein, one may screen the antibodies for binding to a peptide comprising the amino acid sequence of the S1 or S2 domain of SARS-CoV S protein.

In another aspect, the invention provides hybridomas that produce a human anti-SARS-CoV S protein antibody. In one embodiment, the human anti-SARS-CoV S protein antibody produced by the hybridoma is an antagonist of SARS-CoV S protein. In some embodiments, the anti-SARS-CoV S protein monoclonal antibody does not mediate antibody dependent enhancement of viral infection. In one embodiment, the hybridomas are mouse hybridomas, as described above. In other embodiments, the hybridomas are produced in a non-human, non-mouse species such as rats, sheep, pigs, goats, cattle or horses. In another embodiment, the hybridomas are human hybridomas.

In one embodiment of the invention, antibody-producing cells are isolated and expressed in a host cell, for example myeloma cells. In still another embodiment, a transgenic animal is immunized with a SARS-CoV S protein immunogen as described herein, primary cells, e.g., spleen or peripheral blood cells, are isolated from an immunized transgenic animal and individual cells producing antibodies specific for the desired antigen are identified. Polyadenylated mRNA from each individual cell is isolated and reverse transcription polymerase chain reaction (RT-PCR) is performed using sense primers that anneal to variable region sequences, e.g., degenerate primers that recognize most or all of the FR1 regions of human heavy and light chain variable region genes and anti-sense primers that anneal to constant or joining region sequences. cDNAs of the heavy and light chain variable domains are then cloned and expressed in any suitable host cell, e.g., a myeloma cell, as chimeric antibodies with respective immunoglobulin constant regions, such as the heavy chain and κ or λ constant domains. See Babcook, J. S. et al. (1996) *Proc. Natl. Acad. Sci. USA* 93: 7843-48, incorporated herein by reference. Anti SARS-CoV S protein antibodies may then be identified and isolated as described herein.

In another embodiment, phage display techniques can be used to provide libraries containing a repertoire of antibodies with varying affinities for SARS-CoV S protein. For production of such repertoires, it is unnecessary to immortalize the B cells from the immunized animal. Rather, the primary B cells can be used directly as a source of DNA. The mixture of cDNAs obtained from B cell, e.g., derived from spleens, is used to prepare an expression library, for example, a phage display library transfected into *E. coli*. The resulting cells are tested for immunoreactivity to SARS-CoV S protein. Techniques for the identification of high affinity human antibodies from such libraries are described by Griffiths et al., (1994) *EMBO J.*, 13:3245-3260; Nissim et al., ibid, pp. 692-698 and by Griffiths et al., ibid, 12:725-734, which are incorporated by reference. Ultimately, clones from the library are identified that produce binding affinities of a desired magnitude for the antigen and the DNA encoding the product responsible for such binding is recovered and manipulated for standard recombinant expression. Phage display libraries may also be constructed using previously manipulated nucleotide sequences and screened in a similar fashion. In general, the cDNAs encoding heavy and light chains are independently supplied or linked to form Fv analogs for production in the phage library.

The phage library is then screened for the antibodies with the highest affinities for SARS-CoV S protein and the genetic material recovered from the appropriate clone. Further rounds of screening can increase affinity of the original antibody isolated.

Nucleic Acids, Vectors, Host Cells, and Recombinant Methods of Making Antibodies Nucleic Acids The present invention also encompasses nucleic acid molecules encoding anti-SARS-CoV S protein antibodies or antigen-binding portions thereof. In some embodiments, different nucleic acid molecules encode a heavy chain and a light chain of an anti-SARS-CoV S protein immunoglobulin. In other embodiments, the same nucleic acid molecule encodes a heavy chain and a light chain of an anti-SARS-CoV S protein immunoglobulin. In one embodiment, the nucleic acid encodes a SARS-CoV S protein antibody, or antigen-binding portion thereof, of the invention.

In some embodiments, the nucleic acid molecule encoding the variable domain of the light chain ($V_L$) comprises a human Vκ1 or Vκ2 gene, and a Jκ2, Jκ3, Jκ4, or Jκ5 gene with or without mutations from the germline. In various embodiments, the VL utilizes a human Vκ1 gene and a human Jκ3, Jκ4, or Jκ5 gene. In some embodiments, the human Vκ gene is a human A30 gene and the human Jκ gene is a human Jκ3, Jκ4 or Jκ5 gene. In other embodiments, the human Vκ gene is a human L5 gene and the human Jκ gene is a human Jκ4 gene. In still other embodiments, the human Vκ gene is a human A1 gene and the human Jκ gene is a human Jκ2 gene.

In some embodiments, the nucleic acid molecule encoding the light chain, encodes an amino acid sequence comprising 1, 2, 3, 4, 5, 6, 7, 8, 9, or 10 substitutions from the germline amino acid sequence(s). In some embodiments, the nucleic acid molecule comprises a nucleotide sequence that encodes a $V_L$ amino acid sequence comprising 1, 2, 3, 4, 5, 6, 7, 8, 9, or 10 conservative amino acid substitutions and/or 1, 2, or 3 non-conservative substitutions compared to germline $V_K$, $J_K$ and $J_L$ sequences. Substitutions may be in the CDR regions, the framework regions, or in the constant domain.

In some embodiments, the nucleic acid molecule encodes a $V_L$ amino acid sequence comprising one or more variants compared to germline sequence that are identical to the variations found in the $V_L$ of one of the antibodies 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2.

In some embodiments, the nucleic acid molecule encodes at least three amino acid substitutions compared to the germline sequence found in the $V_L$ of one of the antibodies 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2.

In some embodiments, the nucleic acid molecule comprises a nucleotide sequence that encodes the $V_L$ amino acid sequence of 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2, or a variant or portion thereof. In some embodiments, the nucleic acid encodes an amino acid sequence comprising the light chain CDRs of one of said above-listed antibodies. In some embodiments, said portion is a contiguous portion comprising CDR1-CDR3.

In some embodiments, the nucleic acid encodes the amino acid sequence of the light chain CDRs of said antibody. In some embodiments, said portion encodes a contiguous region from CDR1-CDR3 of the light chain of an anti-SARS-CoV S protein antibody.

In some embodiments, the nucleic acid molecule encodes a $V_L$ amino acid sequence that is at least 70%, 75%, 80%, 85%, 90%, 95%, 97%, 98% or 99% identical to a $V_L$ amino acid sequence of a $V_L$ region of any one of antibodies 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2. Nucleic acid molecules of the invention include nucleic acids that hybridize under highly stringent conditions, such as those described above, to a nucleotide sequence encoding the amino acid sequence of a $V_L$ region.

In another embodiment, the nucleic acid encodes a full-length light chain of an antibody selected 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2, or a light chain comprising a mutation, such as one disclosed herein.

In still another embodiment, the nucleic acid molecule encodes the variable domain of the heavy chain ($V_H$) that comprises a human $V_H1$, $V_H3$ or $VH_4$ family gene sequence or a sequence derived therefrom. In various embodiments, the nucleic acid molecule encoding the $V_H$ domain utilizes a human $V_H 1$-2 gene, a human D3-10 gene and a human $J_H 4B$ gene; human $V_H 1$-18 gene, a D1-26 gene and a human $J_H 4B$ gene; a human $V_H 3$-33 gene, a human D2-2 gene and a human $J_H 4B$ gene; a human $V_H 3$-33 gene, a human D4-17 gene and a human $J_H 5B$ gene; or a human $V_H 4$-59 gene, a human D3-9 gene and a human $J_H 6B$ gene.

In some embodiments, the nucleic acid molecule encodes an amino acid sequence comprising 1, 2, 3, 4, 5, 6, 7, 8, 9, 10, 11, 12, 13, 14, 15, 16, 17 or 18 mutations compared to the germline amino acid sequence of the human V, D or J genes. In some embodiments, said mutations are in the $V_H$ region. In some embodiments, said mutations are in the CDR regions.

In some embodiments, the nucleic acid molecule encodes one or more amino acid mutations compared to the germline sequence that are identical to amino acid mutations found in the $V_H$ of one of monoclonal antibodies 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2. In some embodiments, the nucleic acid encodes at least three amino acid mutations compared to the germline sequences that are identical to at least three amino acid mutations found in one of the above-listed monoclonal antibodies.

In some embodiments, the nucleic acid molecule comprises a nucleotide sequence that encodes at least a portion of the $V_H$ amino acid sequence of a monoclonal antibody selected from monoclonal antibodies 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2, a variant thereof, or said sequence having conservative amino acid mutations and/or a total of three or fewer non-conservative amino acid substitutions. In various embodiments the sequence encodes one or more CDR regions, preferably a CDR3 region, all three CDR regions, a contiguous portion including CDR1-CDR3, or the entire $V_H$ region, with or without a signal sequence.

In some embodiments, the nucleic acid molecule comprises a nucleotide sequence that encodes the amino acid sequence of one of 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2, or said sequence lacking the signal sequence. In some preferred embodiments, the nucleic acid molecule comprises at least a portion of the nucleotide sequence of 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2, or said sequence lacking the signal sequence. In some embodiments, said portion encodes the $V_H$ region (with or without a signal sequence), a CDR3 region, all three CDR regions, or a contiguous region including CDR1-CDR3.

In some embodiments, the nucleic acid molecule encodes a $V_H$ amino acid sequence that is at least 70%, 75%, 80%, 85%, 90%, 95%, 97%, 98% or 99% identical to the $V_H$ amino acid sequences of any one of 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2. Nucleic acid molecules of the invention include nucleic acids that hybridize under highly stringent conditions, such as those described above, to a nucleotide sequence encoding the amino acid sequence of 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2, or to a $V_H$ region thereof, or that has the nucleotide sequence of 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2 or that encodes a $V_H$ region thereof.

In another embodiment, the nucleic acid encodes a full-length heavy chain of an antibody selected from 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2, or a heavy chain having the amino acid sequence of 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2, with or without a signal sequence, or a heavy chain comprising a mutation, such as one of the variants discussed herein. Further, the nucleic acid may comprise the nucleotide sequence of 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2, with or without a signal sequence, or a nucleic acid molecule encoding a heavy chain comprising a mutation, such as one of the variants discussed herein.

A nucleic acid molecule encoding the heavy or light chain of an anti-SARS-CoV S protein antibody or portions thereof can be isolated from any source that produces such antibody. In various embodiments, the nucleic acid molecules are isolated from a B cell isolated from an animal immunized with SARS-CoV S protein or from an immortalized cell derived from such a B cell that expresses an anti-SARS-CoV S protein antibody. Methods of isolating mRNA encoding an antibody are well-known in the art. See, e.g., Sambrook et al. The mRNA may be used to produce cDNA for use in the polymerase chain reaction (PCR) or cDNA cloning of antibody genes. In one embodiment, the nucleic acid molecule is isolated from a hybridoma that has as one of its fusion partners a human immunoglobulin-producing cell from a non-human transgenic animal. In an even more preferred embodiment, the human immunoglobulin producing cell is isolated from a XENOMOUSE™ animal. In another embodiment, the human immunoglobulin-producing cell is from a non-human, non-mouse transgenic animal, as described above. In another embodiment, the nucleic acid is isolated from a non-human, non-transgenic animal. The nucleic acid molecules isolated from a non-human, non-transgenic animal may be used, e.g., for humanized antibodies.

In some embodiments, a nucleic acid encoding a heavy chain of an anti-SARS-CoV S protein antibody of the invention can comprise a nucleotide sequence encoding a $V_H$ domain of the invention joined in-frame to a nucleotide sequence encoding a heavy chain constant domain from any source. Similarly, a nucleic acid molecule encoding a light chain of an anti-SARS-CoV S protein antibody of the invention can comprise a nucleotide sequence encoding a $V_L$ domain of the invention joined in-frame to a nucleotide sequence encoding a light chain constant domain from any source.

In a further aspect of the invention, nucleic acid molecules encoding the variable domain of the heavy ($V_H$) and/or light ($V_L$) chains are "converted" to full-length antibody genes. In one embodiment, nucleic acid molecules encoding the $V_H$ or $V_L$ domains are converted to full-length antibody genes by insertion into an expression vector already encoding heavy chain constant ($C_H$) or light chain constant ($C_L$) domains, respectively, such that the $V_H$ segment is operatively linked to the $C_H$ segment(s) within the vector, and/or the $V_L$ segment is operatively linked to the $C_L$ segment within the vector. In another embodiment, nucleic acid molecules encoding the $V_H$ and/or $V_L$ domains are converted into full-length antibody genes by linking, e.g., ligating, a nucleic acid molecule encoding a $V_H$ and/or $V_L$ domains to a nucleic acid molecule encoding a $C_H$ and/or $C_L$ domain using standard molecular biological techniques. Nucleotide sequences of human heavy and light chain immunoglobulin constant domain genes are known in the art. See, e.g., Kabat et al., *Sequences of Proteins of Immunological Interest,* 5th Ed., NIH Publ. No. 91-3242, 1991. Nucleic acid molecules encoding the full-length heavy and/or light chains may then be expressed from a cell into which they have been introduced and the anti-SARS-CoV S protein antibody isolated.

The nucleic acid molecules may be used to recombinantly express large quantities of anti-SARS-CoV S protein antibodies. The nucleic acid molecules also may be used to produce chimeric antibodies, bispecific antibodies, single chain antibodies, immunoadhesins, diabodies, mutated antibodies and antibody derivatives, as described further below. If the nucleic acid molecules are derived from a non-human, non-transgenic animal, the nucleic acid molecules may be used for antibody humanization, also as described below.

In another embodiment, a nucleic acid molecule of the invention is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of anti-SARS-CoV S protein antibodies. In some embodiments, the nucleic acid molecules are oligonucleotides. In some embodiments, the oligonucleotides are from highly variable domains of the heavy and light chains of the antibody of interest. In some embodiments, the oligonucleotides encode all or a part of one or more of the CDRs of antibodies 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2, or variants thereof as described herein.

Vectors

The invention provides vectors comprising nucleic acid molecules that encode the heavy chain of an anti-SARS-CoV S protein antibody of the invention or an antigen-binding portion thereof. The invention also provides vectors comprising nucleic acid molecules that encode the light chain of such antibodies or antigen-binding portion thereof. The invention further provides vectors comprising nucleic acid molecules encoding fusion proteins, modified antibodies, antibody fragments, and probes thereof.

In some embodiments, the anti-SARS-CoV S protein antibodies or antigen-binding portions of the invention are expressed by inserting DNAs encoding partial or full-length light and heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In one embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can easily be inserted and expressed, as described above. In such vectors, splicing usually occurs between the splice donor site in the inserted J region and the splice acceptor site preceding the human C domain, and also at the splice regions that occur within the human $C_H$ exons. Polyadenylation and transcription termination occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods for expressing antibodies in plants, including a description of promoters and vectors, as well as transformation of plants is known in the art. See, e.g., U.S. Pat. 6,517,529, incorporated herein by reference. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, incorporated herein by reference). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification), the neo gene (for G418 selection), and the glutamate synthetase gene.

Non-Hybridoma Host Cells and Methods of Recombinantly Producing Protein

Nucleic acid molecules encoding anti-SARS-CoV S protein antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455, incorporated herein by reference). Methods of transforming plant cells are well known in the art, including, e.g., Agrobacterium-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., Nicotiana, Arabidopsis, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of antibodies of the invention from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, 0 323 997 and 0 338 841.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

Transgenic Animals and Plants

Anti-SARS-CoV S protein antibodies of the invention also can be produced transgenically through the generation of a mammal or plant that is transgenic for the immunoglobulin heavy and light chain sequences of interest and production of the antibody in a recoverable form therefrom. In connection with the transgenic production in mammals, anti-SARS-CoV S protein antibodies can be produced in, and recovered from, the milk of goats, cows, or other mammals. See, e.g., U.S. Pat. Nos. 5,827,690, 5,756,687, 5,750,172, and 5,741,957, incorporated herein by reference. In some embodiments, non-human transgenic animals that comprise human immunoglobulin loci are immunized with SARS-CoV S protein or an immunogenic portion thereof, as described above. Methods for making antibodies in plants are described, e.g., in U.S. Pat. Nos. 6,046,037 and 5,959,177, incorporated herein by reference.

In some embodiments, non-human transgenic animals or plants are produced by introducing one or more nucleic acid molecules encoding an anti-SARS-CoV S protein antibody of the invention into the animal or plant by standard transgenic techniques. See Hogan and U.S. Pat. No. 6,417,429, supra. The transgenic cells used for making the transgenic animal can be embryonic stein cells or somatic cells or a fertilized egg. The transgenic non-human organisms can be chimeric, nonchimeric heterozygotes, and nonchimeric homozygotes. See, e.g., Hogan et al., *Manipulating the Mouse Embryo: A Laboratory Manual* second ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999), all incorporated herein by reference. In some embodiments, the transgenic non-human animals have a targeted disruption and replacement by a targeting construct that encodes a heavy chain and/or a light chain of interest. In one embodiment, the transgenic animals comprise and express nucleic acid molecules encoding heavy and light chains that specifically bind to SARS-CoV S protein, and preferably to (i) the S1 domain of SARS-CoV S protein; (ii) the S2 domain of SARS-CoV S protein; or (iii) both (i) and (ii). In one embodiment, the transgenic animals comprise and express nucleic acid molecules encoding heavy and light chains that specifically bind to human SARS-CoV S protein. In some embodiments, the transgenic animals comprise nucleic acid molecules encoding a modified antibody such as a single-chain antibody, a chimeric antibody or a humanized antibody. The anti-SARS-CoV S protein antibodies may be made in any transgenic animal. In one embodiment, the non-human animals are mice, rats, sheep, pigs, goats, cattle or horses. The non-human transgenic animal expresses said encoded polypeptides in blood, milk, urine, saliva, tears, mucus and other bodily fluids.

Phage Display Libraries

The invention provides a method for producing an anti-SARS-CoV S protein antibody or antigen-binding portion thereof comprising the steps of synthesizing a library of human antibodies on phage, screening the library with SARS-CoV S protein or a portion thereof, isolating phage that bind SARS-CoV S protein, and obtaining the antibody from the phage. By way of example, one method for preparing the library of antibodies for use in phage display techniques comprises the steps of immunizing a non-human animal comprising human immunoglobulin loci with SARS-CoV S protein or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. Recombinant anti-SARS-CoV S protein antibodies of the invention may be obtained in this way.

Recombinant anti-SARS-CoV S protein human antibodies of the invention can be isolated by screening a recombinant combinatorial antibody library. Preferably the library is a scFv phage display library, generated using human $V_L$ and $V_H$ cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SURFZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., *Bio/Technology* 9:1370-1372 (1991); Hay et al., *Hum. Antibod. Hybridomas* 3:81-85 (1992); Huse et al., *Science* 246:1275-1281 (1989); McCafferty et al., *Nature* 348:552-554 (1990); Griffiths et al., *EMBO J.* 12:725-734 (1993); Hawkins et al., *J. Mot. Biol.* 226:889-896 (1992); Clackson et al., *Nature* 352:624-628 (1991); Gram et al., *Proc. Natl. Acad. Sci. USA* 89:3576-3580 (1992); Garrad et al., *Bio/Technology* 9:1373-1377 (1991): Hoogenboom et al., *Nuc. Acid Res.* 19:4133-4137 (1991); and Barbas et al., *Proc. Natl. Acad. Sci. USA* 88:7978-7982 (1991), all incorporated herein by reference.

In one embodiment, to isolate and produce human anti-SARS-CoV S protein antibodies with the desired characteristics, a human anti-SARS-CoV S protein antibody as described herein is first used to select human heavy and light chain sequences having similar binding activity toward SARS-CoV S protein, using the epitope imprinting methods described in PCT Publication No. WO 93/06213, incorporated herein by reference. The antibody libraries used in this method are preferably scFv libraries prepared and screened as described in PCT Publication No. WO 92/01047, McCafferty et al., *Nature* 348:552-554 (1990); and Griffiths et al, *EMBO J.* 12:725-734 (1993), all incorporated herein by reference. The scFv antibody libraries preferably are screened using human SARS-CoV S protein as the antigen.

Once initial human $V_L$ and $V_H$ domains are selected, "mix and match" experiments are performed, in which different pairs of the initially selected $V_L$ and $V_H$ segments are screened for SARS-CoV S protein binding to select preferred $V_L/V_H$ pair combinations. Additionally, to further improve the quality of the antibody, the $V_L$ and $V_H$ segments of the preferred $V_L/V_H$ pair(s) can be randomly mutated, preferably within the CDR3 region of $V_H$ and/or $V_L$, in a process analogous to the in vivo somatic mutation process responsible for affinity maturation of antibodies during a natural immune response. This in vitro affinity maturation can be accomplished by amplifying $V_H$ and $V_L$ domains using PCR primers complimentary to the $V_H$ CDR3 or $V_L$ CDR3, respectively, which primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be re-screened for binding to SARS-CoV S protein.

Following screening and isolation of an anti-SARS-CoV S protein antibody of the invention from a recombinant immunoglobulin display library, nucleic acids encoding the selected antibody can be recovered from the display package (e.g., from the phage genome) and subcloned into other expression vectors by standard recombinant DNA techniques. If desired, the nucleic acid can further be manipulated to create other antibody forms of the invention, as described below. To express a recombinant human antibody isolated by screening of a combinatorial library, the DNA encoding the antibody is cloned into a recombinant expression vector and introduced into mammalian host cells, as described above.

Class Switching

Another aspect of the invention provides a method for converting the class or subclass of an anti-SARS-CoV S protein antibody to another class or subclass. In some embodiments, a nucleic acid molecule encoding a $V_L$ or $V_H$ that does not include sequences encoding $C_L$ or $C_H$ is isolated using methods well-known in the art. The nucleic acid molecule then is operatively linked to a nucleotide sequence encoding a $C_L$ or $C_H$ from a desired immunoglobulin class or subclass. This can be achieved using a vector or nucleic acid molecule that comprises a $C_L$ or $C_H$ chain, as described above. For example, an anti-SARS-CoV S protein antibody that was originally IgM can be class switched to an IgG. Further, the class switching may be used to convert one IgG subclass to another, e.g., from IgG1 to IgG2. Another method for producing an antibody of the invention comprising a desired isotype comprises the steps of isolating a nucleic acid encoding a heavy chain of an anti-SARS-CoV S protein antibody and a nucleic acid encoding a light chain of an anti-SARS-CoV S protein antibody, isolating the sequence encoding the $V_H$ region, ligating the $V_H$ sequence to a sequence encoding a heavy chain constant domain of the desired isotype, expressing the light chain gene and the heavy chain construct in a cell, and collecting the anti-SARS-CoV S protein antibody with the desired isotype.

Deimmunized Antibodies

In another aspect of the invention, the antibody may be deimmunized to reduce its immunogenicity using the techniques described in, e.g., PCT Publication Nos. WO98/52976 and WO00/34317 (incorporated herein by reference).

Mutated Antibodies

In another embodiment, the nucleic acid molecules, vectors and host cells may be used to make mutated anti-SARS-CoV S protein antibodies. The antibodies may be mutated in the variable domains of the heavy and/or light chains, e.g., to alter a binding property of the antibody. For example, a mutation may be made in one or more of the CDR regions to increase or decrease the $K_D$ of the antibody for SARS-CoV S protein, to increase or decrease $k_{off}$, or to alter the binding specificity of the antibody. Techniques in site-directed mutagenesis are well-known in the art. See, e.g., Sambrook et al. and Ausubel et al., supra. In another embodiment, one or more mutations are made at an amino acid residue that is known to be changed compared to the germline in monoclonal antibody 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2. The mutations may be made in a CDR region or framework region of a variable domain, or in a constant domain. In one embodiment, the mutations are made in a variable domain. In some embodiments, one or more mutations are made at an amino acid residue that is known to be changed compared to the germline in a CDR region or framework region of a variable domain of an amino acid sequence selected from 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2.

In another embodiment, the framework region is mutated so that the resulting framework region(s) have the amino acid sequence of the corresponding germline gene. A mutation may be made in a framework region or constant domain to increase the half-life of the anti-SARS-CoV S protein antibody. See, e.g., PCT Publication No. WO 00/09560, incorporated herein by reference. A mutation in a framework region or constant domain also can be made to alter the immunogenicity of the antibody, to provide a site for covalent or non-covalent binding to another molecule, or to alter such properties as complement fixation, FcR binding and antibody-dependent cell-mediated cytotoxicity (ADCC). According to the invention, a single antibody may have mutations in any one or more of the CDRs or framework regions of the variable domain or in the constant domain.

In some embodiments, there are from 1 to 8, including any number in between, amino acid mutations in either the $V_H$ or $V_L$ domains of the mutated anti-SARS-CoV S protein antibody compared to the anti-SARS-CoV S protein antibody prior to mutation. In any of the above, the mutations may occur in one or more CDR regions. Further, any of the mutations can be conservative amino acid substitutions. In some embodiments, there are no more than 5, 4, 3, 2, or 1 amino acid changes in the constant domains.

Modified Antibodies

In another embodiment, a fusion antibody or immunoadhesin may be made that comprises all or a portion of an anti-SARS-CoV S protein antibody of the invention linked to another polypeptide. In one embodiment, only the variable domains of the anti-SARS-CoV S protein antibody are linked to the polypeptide. In still another embodiment, the $V_H$ domain of an anti-SARS-CoV S protein antibody is linked to a first polypeptide, while the $V_L$ domain of an anti-SARS-CoV S protein antibody is linked to a second polypeptide that associates with the first polypeptide in a manner such that the $V_H$ and $V_L$ domains can interact with one another to form an antigen binding site. In still another embodiment, the $V_H$ domain is separated from the $V_L$ domain by a linker such that the $V_H$ and $V_L$ domains can interact with one another (see below under Single Chain Antibodies). The $V_H$-linker-$V_L$ antibody is then linked to the polypeptide of interest. The fusion antibody is useful for directing a polypeptide to a SARS-CoV S protein-expressing cell or tissue. The polypeptide may be a therapeutic agent, such as a toxin, chemokine or other regulatory protein, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody, (scFv) the $V_H$-and $V_L$-encoding DNA fragments are operatively linked to another fragment encoding a flexible linker, e.g., encoding the amino acid sequence (Gly$_4$-Ser)$_3$, such that the $V_H$ and $V_L$ sequences can be expressed as a contiguous single-chain protein, with the $V_L$ and $V_H$ domains joined by the flexible linker. See, e.g., Bird et al., Science 242:423-426 (1988); Huston et al., Proc. Natl. Acad. Sci. USA 80:5879-5883 (1988); McCafferty et al, Nature 348:552-554 (1990). The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to SARS-CoV S protein and to another molecule.

In other embodiments, other modified antibodies may be prepared using anti-SARS-CoV S protein antibody encoding nucleic acid molecules. For instance, "Kappa bodies" (Ill et al., Protein Eng. 10: 949-57 (1997)), "Minibodies" (Martin et al., EMBO J. 13: 5303-9 (1994)), "Diabodies" (Holliger et al., Proc. Natl. Acad. Sci. USA 90: 6444-6448 (1993)), or "Janusins" (Traunecker et al., EMBO J. 10:3655-3659 (1991) and Traunecker et al., Int. J Cancer (Suppl.) 7:51-52 (1992)) may be prepared using standard molecular biological techniques following the teachings of the specification.

Bispecific antibodies or antigen-binding fragments can be produced by a variety of methods including fusion of hybridomas or linking of Fab' fragments. See, e.g., Songsivilai & Lachmann, Clin. Exp. Immunol. 79: 315-321 (1990), Kostelny et al., J. Immunol. 148:1547-1553 (1992). In addition, bispecific antibodies may be formed as "diabodies" or "Janusins." In some embodiments, the bispecific antibody binds to two different epitopes of SARS-CoV S protein. In some embodiments, the bispecific antibody has a first heavy chain and a first light chain from monoclonal antibody 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2 and an additional antibody heavy chain and light chain. In some embodiments, the additional light chain and heavy chain also are from one of the above-identified monoclonal antibodies, but are different from the first heavy and light chains.

In some embodiments, the modified antibodies described above are prepared using one or more of the variable domains or CDR regions from a human anti-SARS-CoV S protein monoclonal antibody provided herein.

Derivatized and Labeled Antibodies

An anti-SARS-CoV S protein antibody or antigen-binding portion of the invention can be derivatized or linked to another molecule (e.g., another peptide or protein). In general, the antibodies or portion thereof are derivatized such that the SARS-CoV S protein binding is not affected adversely by the derivatization or labeling. Accordingly, the antibodies and antibody portions of the invention are intended to include both intact and modified forms of the human anti-SARS-CoV S protein antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a cytotoxic agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., n-maleimidobenzoyl-N-hydroxysuccinimide ester) or homobifunctional (e.g., disuccinimidyl suberate). Such linkers are available from Pierce Chemical Company, Rockford, Ill.

Another type of derivatized antibody is a labeled antibody. Useful detection agents with which an antibody or antigen-binding portion of the invention may be derivatized include fluorescent compounds, including fluorescein, fluorescein isothiocyanate, rhodamine, phycoerythrin, 5-dimethylamine-1-napthalenesulfonyl chloride, lanthanide phosphors and the like. An antibody can also be labeled with enzymes that are useful for detection, such as horseradish peroxidase, β-galactosidase, luciferase, alkaline phosphatase, glucose oxidase and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody can also be labeled with biotin, and detected through indirect measurement of avidin or streptavidin binding. An antibody can also be labeled with a predetermined polypeptide epitope recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

An anti-SARS-CoV S protein antibody can also be labeled with a radiolabeled amino acid. The radiolabel can be used for both diagnostic and therapeutic purposes. For instance, the radiolabel can be used to detect SARS-CoV S protein -expressing tumors by x-ray or other diagnostic techniques. Further, the radiolabel can be used therapeutically as a toxin for cancerous cells or tumors. Examples of labels for polypeptides include, but are not limited to, the following radioisotopes or radionuclides—$^3$H, $^{14}$C, $^{15}$N, $^{35}$S, $^{90}$Y, $^{99}$Tc, $^{111}$In, $^{125}$I, and $^{131}$I.

An anti-SARS-CoV S protein antibody can also be derivatized with a chemical group such as polyethylene glycol (PEG), a methyl or ethyl group, or a carbohydrate group. These groups are useful to improve the biological characteristics of the antibody, e.g., to increase serum half-life or to increase tissue binding.

In some embodiments, the anti-SARS-CoV S protein antibody can be labeled with a paramagnetic, radioactive or fluorogenic ion that is detectable upon imaging. In some embodiments, the paramagnetic ion is chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). In other embodiments, the radioactive ion is iodine123, technetium99, indium111, rhenium188, rhenium186, copper67, iodine131, yttrium90, iodine125, astatine211, and gallium67. In other embodiments, the anti-SARS-CoV S protein antibody is labeled with an X-ray imaging agent such as lanthanum (III), gold (III) lead (II) and bismuth (III).

Compositions and Kits

The invention relates to compositions comprising a human anti-SARS-CoV S protein antibody with antagonist properties for the treatment of patients infected with SARS-CoV. In certain embodiments, a composition may comprise antibodies of any of the precedding embodiments. In some embodiments, the subject of treatment is a human. In other embodiments, the subject is a veterinary subject.

Antagonist anti-SARS-CoV S protein antibodies of the invention and compositions comprising them can be administered in combination with one or more other therapeutic, diagnostic, or prophylactic agents. In some embodiments, more than one antagonist SARS-CoV S protein antibody of the invention can be used in treatment of a subject. In some embodiments, an antagonist anti-SARS-CoV S protein antibody that binds to the S1 domain and one that binds to the S2 domain or antigen-binding portions of either or both, are both administered to a subject, either together or separately. In certain embodiments the antibodies are in a composition comprising a pharmaceutically acceptable carrier. In another embodiment, one or more of the antagonist SARS-CoV S protein antibodies of the invention are administered in combination with one or more additional antagonistic antibodies that bind different epitopes on the S protein, that bind the S protein from different isolates of SARS-CoV and/or that bind different stages of SARS-CoV (i.e., early, middle or late stage virus).

As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

The compositions of this invention may be in a variety of forms, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In one embodiment, the antibody is administered by intravenous infusion or injection. In still another embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the anti-SARS-CoV S protein antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies of the present invention can be administered by a variety of methods known in the art, although for many therapeutic applications, the preferred route/mode of administration is subcutaneous, intramuscular, or intravenous infusion. As will be appreciated by the skilled artisan, the route and/or mode of administration will vary depending upon the desired results. Other modes of administration include intraperitoneal, intrabronchial, transmucosal, intraspinal, intrasynovial, intraaortic, intranasal, ocular, otic, topical and buccal.

In certain embodiments, the active compound of the antibody compositions may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems* (J. R. Robinson, ed., Marcel Dekker, Inc., New York, 1978).

The invention also provides compositions suitable for administration by inhalation, which comprise the anti-SARS-CoV S protein antibodies described herein. The anti-SARS-CoV S protein antibodies may be conveniently delivered to a subject in the form of an aerosol spray presentation from pressurized packs or from a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch. Dellamary et al. (2004) *J Control Release.*;95(3): 489-500 describes formulations for the pulmonary delivery of antibodies. Such inhalational formulations may be particular useful for the treatment of asthma or for reducing inflammation in the pulmonary mucosa.

The invention also provides compositions, suitable for administration through the oral mucosa, which comprise the anti-SARS-CoV S protein antibody described herein. Oral transmucosal delivery refers to the delivery of a delivery vehicle across a mucous membrane in the oral cavity, pharyngeal cavity, or esophagus, and may be contrasted, for example, with traditional oral delivery, in which absorption of a drug occurs in the intestine. Accordingly, routes of administration in which the anti-SARS-CoV S protein antibodies are absorbed through the buccal, sublingual, gingival, pharyngeal, and/or esophageal mucosa are all encompassed within "oral transmucosal delivery," as that term is used herein. For administration through the transmucosal mucosa, the anti-SARS-CoV S protein antibody may be formulated, for example, into chewing gums (see U.S. Pat. No. 5,711,961) or buccal patches (see e.g. U.S. Pat. No. 5,298,256).

The invention also provides compositions suitable for administration through the vaginal mucosa, which comprise the anti-SARS-CoV S protein antibodies described herein. The anti-SARS-CoV S protein antibodies of the invention may be formulated into a vaginal suppository, foam, cream, tablet, capsule, ointment, or gel.

In certain embodiments, the compositions comprising the anti-SARS-CoV S protein antibodies are formulated with permeants appropriate to the transmucosal barrier to be permeated. Such penetrants are generally known in the art, and include, for example, for transmucosal administration bile salts and fusidic acid derivatives In certain embodiments, an anti-SARS-CoV S protein antibody of the invention can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the anti-SARS-CoV S protein antibodies can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Additional active compounds also can be incorporated into the compositions. In certain embodiments, an inhibitory anti-SARS-CoV S protein antibody of the invention is co-formulated with and/or co-administered with one or more additional therapeutic agents, particularly anti-viral agents. These therapeutic agents include, without limitation, antibodies that bind other targets, photosensitizers, androgen, estrogen, non-steroidal antiinflammatory agents, antihypertensive agents, analgesic agents, antidepressants, antibiotics, anticancer agents, anesthetics, antiemetics, antiinfectants, contraceptives, antidiabetic agents, steroids, anti-allergy agents, chemotherapeutic agents, anti-migraine agents, agents for smoking cessation, anti-viral agents, immunosuppresants, thrombolytic agent, cholesterol-lowering agents and anti-obesity agents.

Therapeutic agents also include peptide analogues that inhibit SARS-CoV S protein activity, antibodies or other molecules that prevent SARS-CoV entry into a cell, including but not limited to preventing S protein binding to a receptor such as the ACE2 receptor, and agents that inhibit SARS-CoV S protein expression. In one embodiment, the additional agents that inhibit SARS-CoV S protein expression comprise an antisense nucleic acid capable of hybridizing to a SARS- CoV S protein mRNA, such as a hairpin RNA or siRNA, locked nucleic acids (LNA) or ribozymes. Sequence-specific nucleic acids capable of inhibiting gene function by RNA interference are well-known in the art. Such combination therapies may require lower dosages of the inhibitory anti-SARS-CoV S protein antibody as well as the co-administered agents, thus avoiding possible toxicities or complications associated with the various monotherapies.

In certain specific embodiments, the therapeutic agent(s) that is co-formulated with and/or co-administered with an inhibitory anti-SARS-CoV S protein antibody of the invention is an antimicrobial agent. Antimicrobial agents include antibiotics (e.g. antibacterial), antiviral agents, antifungal agents, and anti-protozoan agents. Non-limiting examples of antimicrobial agents are sulfonamides, trimethoprim-sulfamethoxazole, quinolones, penicillins, and cephalosporins.

The compositions of the invention may include a "therapeutically effective amount" or a "prophylactically effective amount" of an antibody or antigen-binding portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the anti-SARS-CoV S protein antibody or portion thereof and the particular therapeutic or prophylactic effect to be achieved, and (b) the limitations inherent in the art of compounding such an antibody for the treatment of sensitivity in individuals.

An exemplary, non-limiting range for a therapeutically or prophylactically-effective amount of an antibody or antibody portion of the invention is 0.025 to 50 mg/kg, more preferably 0.1 to 50 mg/kg, more preferably 0.1-25, 0.1 to 10 or 0.1 to 3 mg/kg. In some embodiments, a formulation contains 5 mg/ml of antibody in a buffer of 20 mM sodium citrate, pH 5.5, 140 mM NaCl, and 0.2 mg/ml polysorbate 80. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Another aspect of the present invention provides kits comprising an anti-SARS-CoV S protein, or antigen-binding portion, of the invention or a composition comprising such an antibody or antigen-binding fragment. A kit may include, in addition to the antibody or composition, diagnostic or therapeutic agents. A kit can also include instructions for use in a diagnostic or therapeutic method, as well as packaging material such as, but not limited to, ice, dry ice, styrofoam, foam, plastic, cellophane, shrink wrap, bubble wrap, cardboard and starch peanuts. In one embodiment, the kit includes the antibody or a composition comprising it and a diagnostic agent that can be used in a method described below. In still another embodiment, the kit includes the antibody or a composition comprising it and one or more therapeutic agents that can be used in a method described below.

The invention also relates to compositions for inhibiting viral infection, and in particular SARS infection, in a mammal comprising an amount of an antibody of the invention in combination with an amount of an antiviral agent, wherein the amounts of the anti-SARS-CoV S protein antibody and of antiviral agent are together effective in inhibiting viral replication, viral infection of new cells or viral loads. Many antiviral agents are presently known in the art, including nucleoside analogues (e.g., AZT, 3TC, ddI), protease inhibitors and chemokine receptor antagonists.

Diagnostic Methods of Use

In another aspect, the invention provides diagnostic methods. The anti-SARS-CoV S protein antibodies can be used to detect SARS-CoV S protein in a biological sample in vitro or in vivo. In one embodiment, the invention provides a method for diagnosing the presence or location of SARS-CoV viruses in a subject in need thereof.

The anti-SARS-CoV S protein antibodies can be used in a conventional immunoassay, including, without limitation, an ELISA, an RIA, flow cytometry, tissue immunohistochemistry, Western blot or immunoprecipitation. The anti-SARS-CoV S protein antibodies of the invention can be used to detect SARS-CoV S protein from humans.

The invention provides a method for detecting SARS-CoV S protein in a biological sample comprising contacting the biological sample with an anti-SARS-CoV S protein antibody of the invention and detecting the bound antibody. In one embodiment, the anti-SARS-CoV S protein antibody is directly labeled with a detectable label. In another embodiment, the anti-SARS-CoV S protein antibody (the first antibody) is unlabeled and a second antibody or other molecule that can bind the anti-SARS-CoV S protein antibody is labeled. As is well known to one of skill in the art, a second antibody is chosen that is able to specifically bind the particular species and class of the first antibody. For example, if the anti-SARS-CoV S protein antibody is a human IgG, then the secondary antibody could be an anti-human-IgG. Other molecules that can bind to antibodies include, without limitation, Protein A and Protein G, both of which are available commercially, e.g., from Pierce Chemical Co.

Suitable labels for the antibody or secondary antibody have been disclosed supra, and include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

In other embodiments, SARS-CoV S protein can be assayed in a biological sample by a competition immunoassay utilizing SARS-CoV S protein standards labeled with a detectable substance and an unlabeled anti-SARS-CoV S protein antibody. In this assay, the biological sample, the labeled SARS-CoV S protein standards and the anti-SARS-CoV S protein antibody are combined and the amount of labeled SARS-CoV S protein standard bound to the unlabeled antibody is determined. The amount of SARS-CoV S protein in the biological sample is inversely proportional to the amount of labeled SARS-CoV S protein standard bound to the anti-SARS-CoV S protein antibody.

One can use the immunoassays disclosed above for a number of purposes. For example, the anti-SARS-CoV S protein antibodies can be used to detect SARS-CoV S protein in cultured cells or as a diagnostic assay in samples from a subject.

Therapeutic Methods of Use

In another embodiment, the invention provides a method for neutralizing SARS-CoV by administering an anti-SARS-CoV S protein antibody to a patient in need thereof. Any of the types of antibodies described herein may be used therapeutically. In various embodiments, the anti-SARS-CoV S protein antibody is a human antibody. In some embodiments, the antibody, or antigen-binding portion thereof, binds to the S1 domain of SARS-CoV S protein.

In some embodiments, the patient is a human patient. Alternatively, the patient may be a mammal infected with SARS-CoV. The antibody may be administered to a non-human mammal infected with SARS for veterinary purposes or as an animal model of human disease. Such animal models may be useful for evaluating the therapeutic efficacy of antibodies of this invention.

In one embodiment, the invention provides methods of treating, aiding in the treatment, preventing or aiding in the prevention of, SARS-CoV infection and conditions or disorders resulting from such infection, in a subject by administering to the subject a therapeutically-effective amount of an anti-SARS-CoV S protein antibody of the invention.

Antibodies and antigen-binding fragments thereof which are antagonists of SARS-CoV S protein can be used as therapeutics for SARS-CoV infection. SARS-CoV infects target cells via the spike (S) protein expressed on the virus surface. SARS-CoV S protein is a type one transmembrane glycoprotein divided into two functional domains, S1 (amino acids 15-680) and S2 (amino acids 681-1255). The S1 subunit mediates the interaction of the S protein with its receptor, angiotensin converting enzyme 2 (Ace2). A region of S1 consisting of 193 amino acids named receptor binding domain (RBD) is responsible for ACE2 binding. The S2 subunit of the S protein mediates fusion of viral and host membranes through a conformational change in which two conserved helical regions of the S protein are brought together to form a six-helix bundle fusion core.

The antibody may be administered once, but more preferably is administered multiple times. The antibody may be administered from three times daily to once every six months or longer. The administering may be on a schedule such as three times daily, twice daily, once daily, once every two days, once every three days, once weekly, once every two weeks, once every month, once every two months, once every three months and once every six months. The antibody may also be administered continuously via a minipump. The antibody may be administered via an oral, mucosal, buccal, intranasal, inhalable, intravenous, subcutaneous, intramuscular, parenteral, intratumor or topical route. The antibody may be administered locally or systemically.

The therapeutic compositions comprising anti-SARS-CoV S protein antibodies may be administered to the subject, for example, orally, nasally, vaginally, buccally, rectally, via the eye, or via the pulmonary route, in a variety of pharmaceutically acceptable dosing forms, which will be familiar to those skilled in the art.

For example, the anti-SARS-CoV S protein antibodies may be administered via the nasal route using a nasal insufflator device. Examples of these are already employed for commercial powder systems intended for nasal application (e.g. Fisons Lomudal System). Details of other devices can be found in the pharmaceutical literature (see for example Bell, A. Intranasal Delivery devices, in Drug Delivery Devices Fundamentals and Applications, Tyle P. (ed), Dekker, N.Y., 1988).

The anti-SARS-CoV S protein antibodies can be administered to the vagina in a freeze dried powder formulation. Anti-SARS-CoV S protein antibodies may be administered in a vaginal applicator and once in the vagina, the formulation comprising the anti-SARS-CoV S protein antibodies are released by pressing a syringe-type piston or similar release mechanism on the applicator. Alternatively, the anti-SARS-CoV S protein antibodies may be formulated as a powder using a powder device, formulated into a vagina suppository or pessary or vaginal tablet or vaginal gel.

The anti-SARS-CoV S protein antibodies can also be administered to the eye in a gel formulation. For example, before administration, a formulation containing the anti-SARS-CoV S protein antibodies may be conveniently contained in a two compartment unit dose container, one compartment containing a freeze-dried anti-SARS-CoV S protein antibody preparation and the other compartment containing normal saline. Prior to application, the two compartments are mixed and a gel is formed, which is then administered to the eye.

Other delivery routes for the anti-SARS-CoV S protein antibodies include via the pulmonary route using a powder inhaler or metered dose inhaler, via the buccal route formulated into a tablet or a buccal patch, via the rectal route formulated into suppositories; and via the oral route in the form of a tablet, a capsule or a pellet (which compositions may administer agent via the stomach, the small intestine or the colon), all of which may be formulated in accordance with techniques which are well known to those skilled in the art.

The antibody may be administered once, at least twice or for at least the period of time until the condition is treated, palliated or cured. The antibody will generally be administered as part of a composition as described supra. The dosage of antibody will generally be in the range of 0.1-100 mg/kg, more preferably 0.5-50 mg/kg, more preferably 1-20 mg/kg, and even more preferably 1-10 mg/kg. The serum concentration of the antibody may be measured by any method known in the art.

In another embodiment, the antibodies of the present invention are administered to the subject in combination with other therapeutic agents. In one embodiment, the additional therapeutic agents may be treat the symptoms of the SARS-CoV infection on their own, and may optionally synergize with the effects of the antibodies. The additional agent that is administered may be selected by one skilled in the art for treating the infection.

Co-administration of the antibody with an additional therapeutic agent (combination therapy) encompasses administering a composition comprising the anti-SARS-CoV S protein antibody and the additional therapeutic agent as well as administering two or more separate compositions, one comprising the anti-SARS-CoV S protein antibody and the other(s) comprising the additional therapeutic agent(s). Further, although co-administration or combination therapy generally means that the antibody and additional therapeutic agents are administered at the same time as one another, it also encompasses instances in which the antibody and additional therapeutic agents are administered at different times. For instance, the antibody may be administered once every three days, while the additional therapeutic agent is administered once daily. Alternatively, the antibody may be administered prior to or subsequent to treatment with the additional therapeutic agent, for example after a patient has failed therapy with the additional agent. Similarly, administration of the anti-SARS-CoV S protein antibody may be administered prior to or subsequent to other therapy.

The antibody and one or more additional therapeutic agents (the combination therapy) may be administered once, twice or at least the period of time until the condition is treated, palliated or cured. Preferably, the combination therapy is administered multiple times. The combination therapy may be administered from three times daily to once every six months. The administering may be on a schedule such as three times daily, twice daily, once daily, once every two days, once every three days, once weekly, once every two weeks, once every month, once every two months, once every three months and once every six months, or may be administered continuously via a minipump. The combination therapy may be administered via an oral, mucosal, buccal, intranasal, inhalable, intravenous, subcutaneous, intramuscular, or parenteral.

In certain aspects, the disclosure provides a method for treating, preventing or alleviating the symptoms of a SARS-CoV-mediated disorder in a subject in need thereof, comprising the step of administering to said subject an antibody or antigen-binding portion according to any one of the preceding embodiments, further comprising at least one additional therapeutic agent selected from the group consisting of:

(a) one or more antibodies from the group consisting of: 1B5, 1G3, 2E8.1, 2E8.2, 2B10. 1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8, 6C1, and 6C2;
(b) one or more antibodies that specifically bind SARS-CoV S protein of a plurality of SARS-CoV strains;
(c) one or more neutralizing antibodies that do not bind SARS-CoV S protein;
(d) one or more agents that bind SARS-CoV S protein receptor; and
(e) one or more anti-viral agents.

In certain embodiments, antibodies with different binding specificities may be used in combination to simultaneously target several neutralizing epitopes and prevent emergence of escape mutants. In certain embodiments, neutralizing epitopes may include regions of S1 or S2, other SARS-CoV proteins, or S protein receptors. In certain embodiments, the neutralizing epitopes are in the S1 RBD domain or upstream of the RBD.

In certain embodiments, antibodies with binding specificities to a plurality of viral strains may be used in combination to simultaneously target multiple viral strains. In certain embodiments, an antibody may find to a single strain or multiple strains. A number of SARS-CoV strains have been described and are known to one of skill in the art, for example some common SARS-CoV strains include: TWJ, Urbani, and Tor2.

In order that this invention may be better understood, the following examples are set forth. These examples are for purposes of illustration only and are not to be construed as limiting the scope of the invention in any manner.

EXAMPLE I

Production of Human Anti-SARS-CoV S Protein Antibodies

Preparation of Purified S Protein Ectodomain

A cDNA encoding amino acids 1-1193 of the ectodomain of the S protein (Tor2; Genbank accession number: AY274119) (kind gift from Marco Marra and Caroline Astell at British Columbia Cancer Agency Genome Sciences Centre) was cloned into the BACULODIRECT™ Baculovirus Expression System (Invitrogen) in frame with a V5-HIS-tag. The protein was expressed in Sf9 cells and purified using PROBOND™ Nickel-Chelating Resin (Invitrogen).

Immunization and Hybridoma Production

Five micrograms of purified S protein was emulsified in TITERMAX™ Gold adjuvant (Sigma) and 6-10 week old IgG2K XENOMOUSE® animals were immunized intraperitoneally. Subsequent boosts were performed sequentially using TITERMAX™ Gold or alum (Sigma) as adjuvants. When the animals developed an anti-S antibody response, a final boost in PBS was performed, four days later the spleen and lymph cells were harvested, fused with P3 myeloma cells and HPRT+ hybridomas were selected in hypoxanthine-azaserine (HA) using a standard protocol (Davis).

Hybridoma supernatants from a total of 11,520 wells were individually screened for S reactivity by ELISA against S-V5-HIS with a counter screen against OVA-V5-HIS as a control. Hybridoma supernatants yielding OD values above 0.7 when tested against S-V5-HIS (Tor2) were further tested against various S1-Ig fragments by ELISA.

EXAMPLE II

Epitope Mapping

Production and Purification of S1-Ig Protein and Fragments

The cDNAs encoding different S1-Ig fragments (i.e. aa 12-672, 12-510, 261-672, 318-510) were transformed into MC1061/P3 cells and the bacteria were grown on tetracycline and ampicillin agar plates. The constructs were confirmed by restriction analysis using Nhe1 and BamHI (FIG. 1A).

The S1-Ig fragments consisted of amino acids 12-672, 12-510, 261-672, or 318-510, the C5 signal sequence and a human Ig Fc lacking the transmembrane domain to allow secretion of the protein. The cDNAs encoding S1-Ig fragments were transfected into 293T cells using a $CaPO_3$ transfection kit (Invitrogen). Briefly, 293T cells were seeded 1 day prior to transfection, and the media changed the following morning. The $CaPO_3$ transfection procedure was performed as follows: 10 μg DNA+50 μl $CaCl_2$ (2.5M)+450 μl sterile $H_2O$ was mixed and added to 500 μl of HBS while aerating (values are per transfected plate.). This mixture was incubated for 20 minutes at room temperature and subsequently was added dropwise to 293T cells. Next day the cells were washed with PBS+1 mM $CaCl_2$+0.5 M $MgCl_2$ and medium replaced with 293T serum free medium supplemented with 2 mM L-glutamine and antibiotic/antimycotic (Gibco). Cells were incubated at 37° C. for two days at which time the medium was harvested and protease inhibitor tablets added (Roche). The supernatant was then spun at 1500 rpm for 5 minutes to remove any cell debris, and protein purified from the supernatant using Protein-A sepharose beads (Santa Cruz Biotechnology) by rocking overnight at 4° C. Beads were then washed with PBS+$CaCl_2$+$MgCl_2$+0.5M $NaCl_2$ one time followed by two additional washes with PBS+$CaCl_2$+$MgCl_2$. Protein was eluted using 50 mM sodium citrate/50 mM glycine at pH 2 and neutralized immediately using Tris-HCl (pH 9.5). Protein was concentrated on CENTRICON™ filters (Amicon) spinning at 3000 rpm for 1 hour at 4° C. Protein was then dialyzed overnight at 4° C. against PBS.

Reactivity of Hybridoma Supernatants with S1 Fragments

As described above, hybridoma supernatants were tested against a recombinant S protein (S-V5-HIS Tor2 isolate), and counter-screened against OVA-V5-HIS protein as a control. This led to the identification of 666 hybridomas producing human monoclonal antibodies against the SARS-CoV S protein (Table 1). From the initial screening, 576 anti-SARS-CoV S protein monoclonal antibodies with OD values above ~0.7 were selected, further tested and characterized. These monoclonal antibodies were examined for their reactivity with the S1 domain of the S protein containing amino acids 12-672.

Initial screening was carried out using the full-length S1-Ig (12-672). Briefly, plates were coated with 50 ng/well of S1-IgG protein overnight at 4° C. The plates were blocked using 5% non-fat milk, 0.05% Tween-20 for 1 hour at room temperature, washed and 50 µl of hybridoma supernatant (diluted 1:3.5) was added to each well and incubated at room temperature for 1 hour. After washing, 50 µl/well of HRP conjugated goat-anti-human antibody was added and incubated for 1 hour at room temperature. Following washing, the antibody binding was detected using 50 µl/well of substrate and the reaction stopped using 25 µl of 10% HCl; the absorbance was then read on an ELISA plate reader (BioRad) at 450 nm. The same procedure was followed for screening of hybridoma supernatants (used at a dilution of 1:6) and purified human monoclonal antibodies (HmAbs) using the other S1-Ig fragments.

Figure 2:
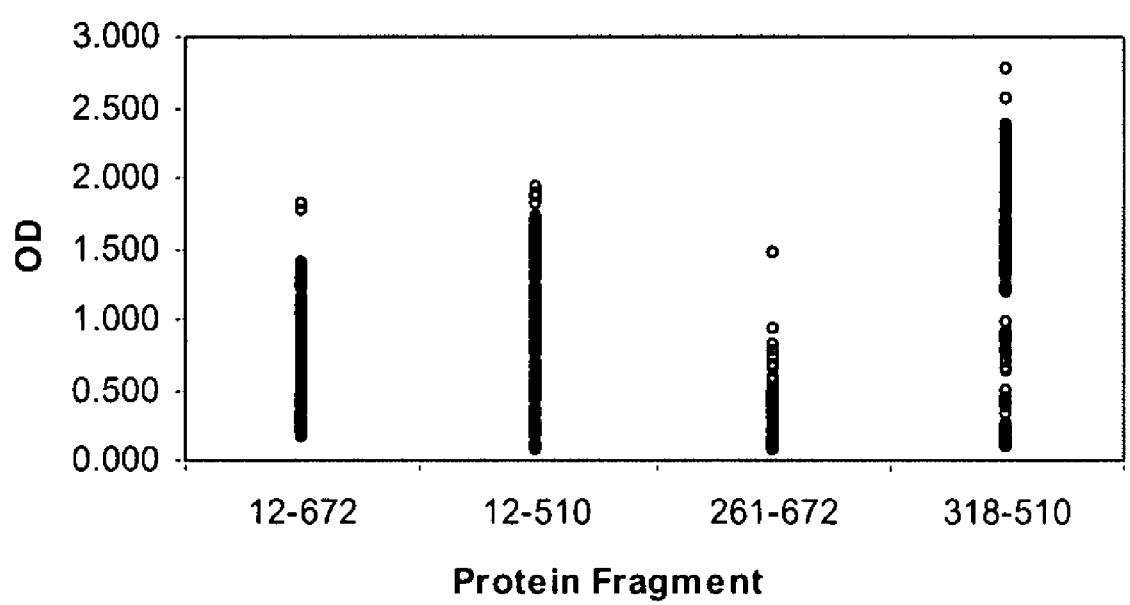
FIG. 2 shows reactivity of anti-SARS-CoV antibodies produced from hybridomas generated from immunized XENOMOUSE® mice against S1-Ig fragments. All S -V5-HIS reacting monoclonal antibodies were tested against S1-Ig (12-672) fragments in an ELISA. A total of 165 human monoclonal antibodies reacted with S1-Ig (12-672). These monoclonal antibodies were then further examined for their reactivity against the other three S1-Ig fragments (12-510, and 318-510). Plates were coated with indicated protein fragments at 50 ng/well, 50 µl of hybridoma supernatant containing S specific human antibodies were used. HRP conjugated anti-human antibody was used to detect the binding of human antibodies. An OD of ≧0.5 was considered to be highly reactive.

This screening identified 165 monoclonal antibodies that were specific to the S1 domain of the S protein with reactivity ranging from 0.171 to 1.817 (FIG. 2). Samples with OD values greater than 2× the average background value (0.0825) were considered positive (FIG. 2). These 165 S1 reacting antibodies were further analyzed for their ELISA reactivity with additional S1 protein fragments (i.e. 12-510, 261-672 and 318-510). The smallest fragment encoding the minimal RBD 318-510 often yielded the highest reactivity for most of the monoclonal antibodies tested relative to the other fragments. Fragments consisting of amino acids 12-672 and 261-672 demonstrated the least reactivity. One explanation for this observation is that the region between 511 and 672 could possibly partially mask epitopes within 318-510 in these S1 fragments (FIG. 2).

The antibodies were grouped based on their reactivity with various S1 fragments (Table 2). Comparison of antibody (Ab) reactivity across all S1 fragments indicated that most Abs react within the receptor binding domain 318-510. Antibodies that bound to 318-510 however fell into four groups (group designation 1A-1D), based on their differential reactivity with the other S1 fragments. The differences in S1 fragment reactivity suggest that the epitope(s) recognized by the monoclonal antibodies in each group, though still within 318-510, are different.

Further epitope mapping experiments were conducted using overlapping peptides derived from the 318-510 region of S1 domain (provided by NIH). These peptides consist of 18 amino acids with 10 amino acid overlap. None of the antibodies showed significant reactivity with any of the peptides indicating that the antibodies recognized either conformational epitopes and/or require glycosylation SARS coronavirus (SARS-CoV) Urbani strain (Genbank accession number: AY278741) was obtained from the CDC. Virus was propagated in VeroE6 cells in OPTIPRO™ serum free medium (SFM). The $TCID_{50}$ value was then determined by infecting 5×10³ VeroE6 cells/well in a 96 well plate with serial 1:10 dilution of SARS-CoV, 8 wells were infected per dilution. After 3 days of incubation at 37° C. in a 5% $CO_2$ humidified incubator cells were evaluated for cytopathic effect (CPE). The $TCID_{50}$ value was calculated as follows: –log $TCID_{50}$=–log dilution above 50% +(–proportionate distance).

Because mice were immunized with full-length S protein, monoclonal antibodies that did not react with the S1 domain were examined for their reactivity with HR1 and HR2 domains in the S2 region. None of the antibodies reacted with HR1 and three showed significant reactivity with HR2. Two of the three HR2 binding Abs resulted in high OD values (1.281 and 1.26), however, none of these three Abs showed neutralizing activity (data not shown).

EXAMPLE III

Identification of Neutralizing Monoclonal Antibodies

ELISA positive monoclonal antibodies were tested for their ability to neutralize SARS-CoV in a microneutralization assay.

VeroE6 cells were seeded at 5×10³ cells per well in a 96 well plate a few hours before the neutralization assay was performed in OPTIPRO™ SFM (Gibco). Neutralizing ability of the Abs in hybridoma supernatants was tested by mixing 50 µl of hybridoma supernatant with 200×$TCID_{50}$ of virus in 50 µl of medium for 1 hour at 37° C. Following incubation, the antibody/virus mixture was added to VeroE6 cells and incubated at 37° C. for 3 days. At this time, cells were visually observed for cytopathic effect (CPE; indicated by rounding of VeroE6 cells) as an indicator of SARS-CoV infection. A similar assay was performed using 1:4 serial dilutions of purified human monoclonal antibodies (HmAbs).

VeroE6 cells were seeded at 5×10³ cells per well in a 96 well plate a few hours before the neutralization assay was performed in OPTIPRO™ SFM (Gibco). Neutralizing ability of the Abs in hybridoma supernatants was tested by mixing 50 µl of hybridoma supernatant with 200×$TCID_{50}$ of virus in 50 µl of medium for 1 hour at 37° C. Following incubation, the antibody/virus mixture was added to VeroE6 cells and incubated at 37° C. for 3 days. At this time, cells were visually observed for cytopathic effect (CPE; indicated by rounding of VeroE6 cells) as an indicator of SARS-CoV infection. A similar assay was performed using 1:4 serial dilutions of purified human monoclonal antibodies (HmAbs).

Of the 165 strongly S1 positive HmAbs, 27 antibodies completely neutralized 200$TCID_{50}$ SARS-CoV as indicated by a total lack of CPE (Table 2). A significant proportion of the neutralizing monoclonal antibodies reacted with the RBD of the S protein consisting of amino acids 318-510. Though fewer Abs belonged to group 1A, the majority of these Abs were neutralizing and suggested that they are reacting with a dominant neutralizing domain containing one or more epitope(s). The same can be said for Abs in group1B, the majority of neutralizing Abs belonged to this group indicating that they are also reacting with a dominant neutralizing domain, but most likely distinct from that recognized by Abs in group 1A.

Three additional neutralizing HmAbs were found that most likely bind to a region between amino acids 12 and 261 of the S1 domain. This is analogous to other studies which have shown neutralizing ability of Abs that bind upstream of the known RBD (i.e. 130-150). However, how these Abs prevent SARS-CoV infection is yet to be determined.

EXAMPLE IV

Characterization of Purified Human Anti-SARS-CoV Monoclonal Antibodies

Figure 3:
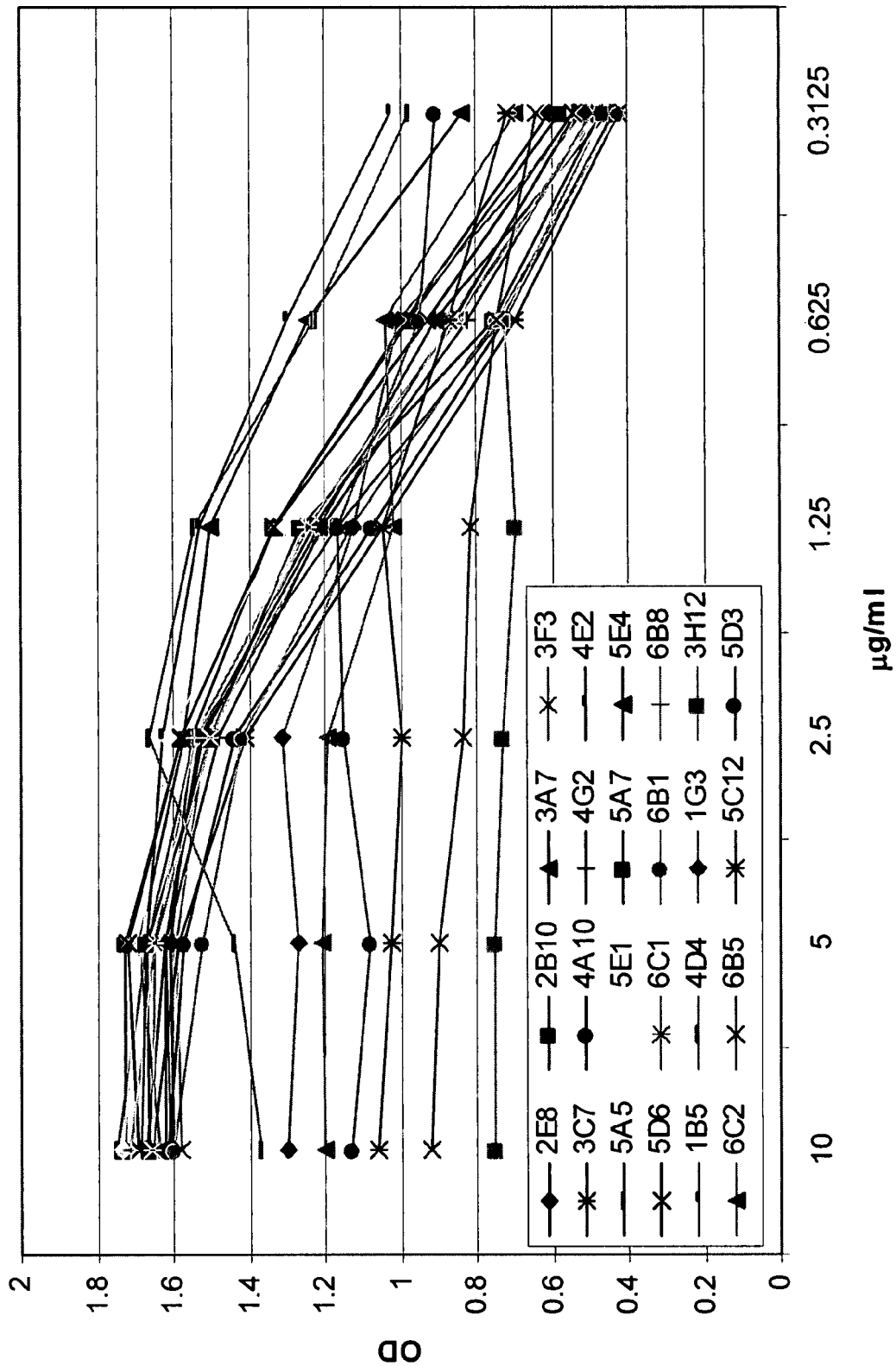
FIG. 3 shows neutralizing monoclonal antibodies were purified and examined for S1-Ig fragment reactivity. Following identification of neutralizing monoclonal antibodies, purified antibodies were examined by ELISA for their reactivity against relevant S1-Ig fragments (318-510 or 12-510). Plates were coated with the indicated protein fragments at 50 ng/well and indicated amounts of human monoclonal antibodies were added. HRP conjugated anti-human antibody was used to detect the binding of human antibodies.
Figure 5A:
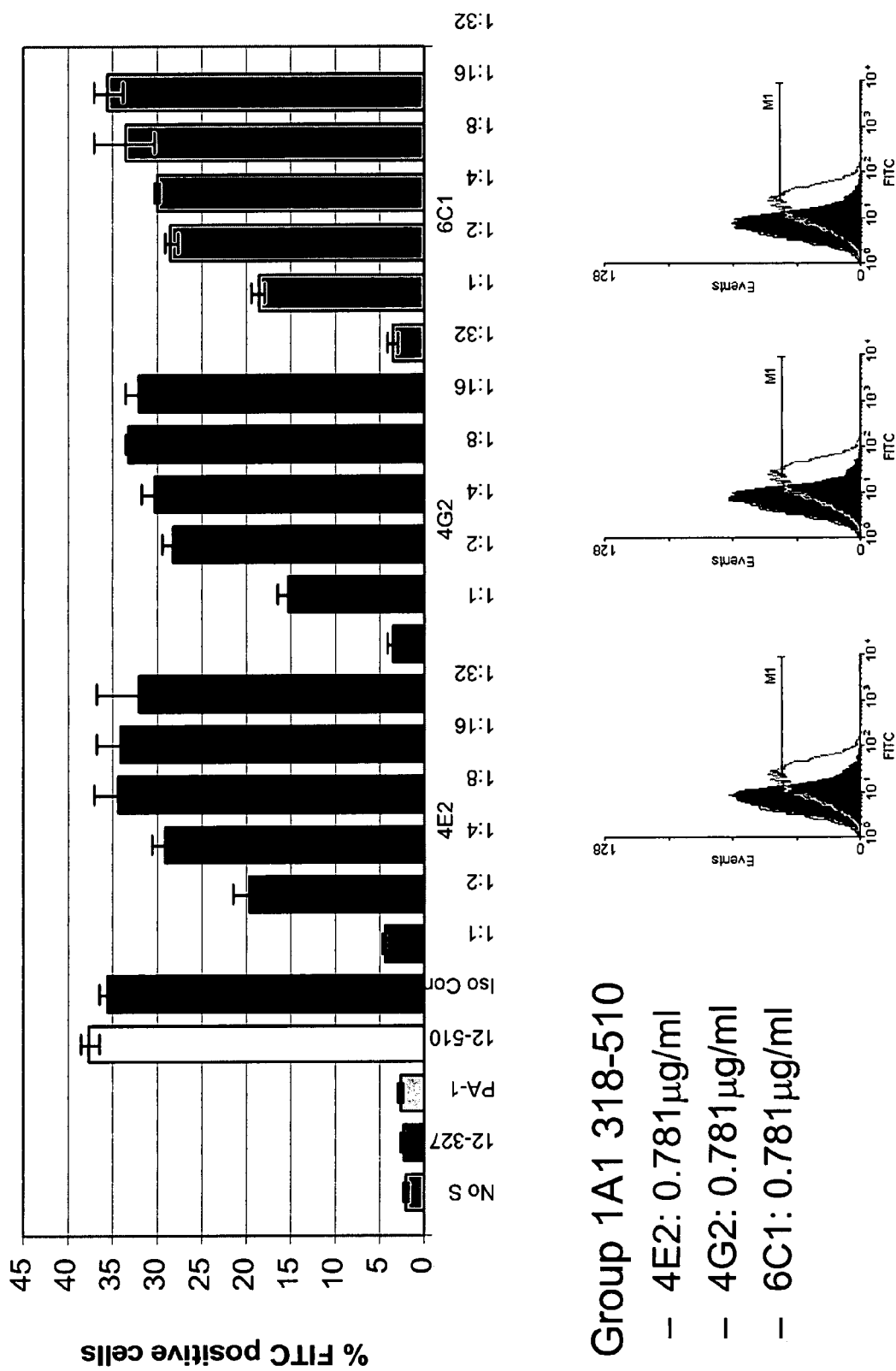
Figure 5B:
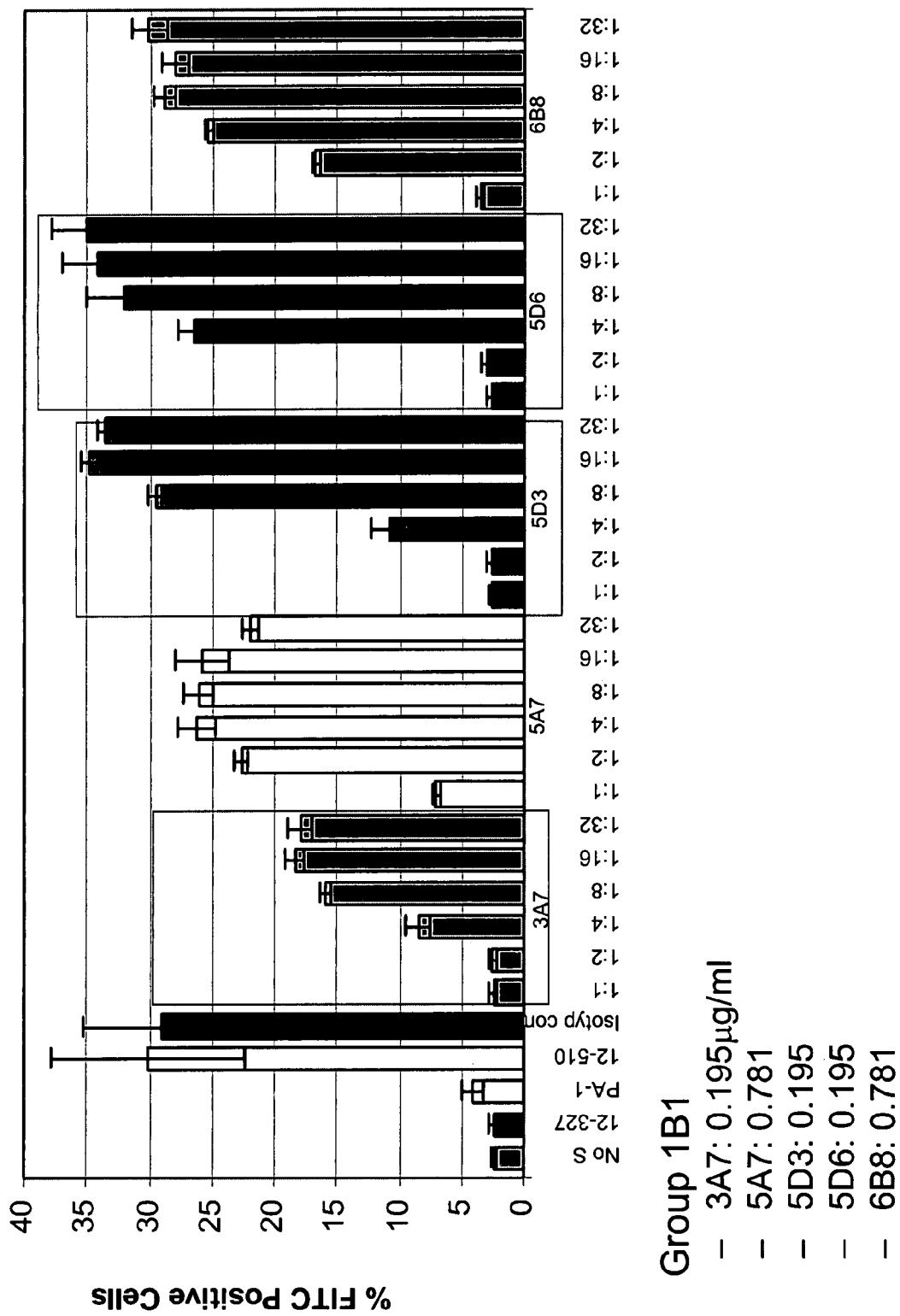
Figure 5C:
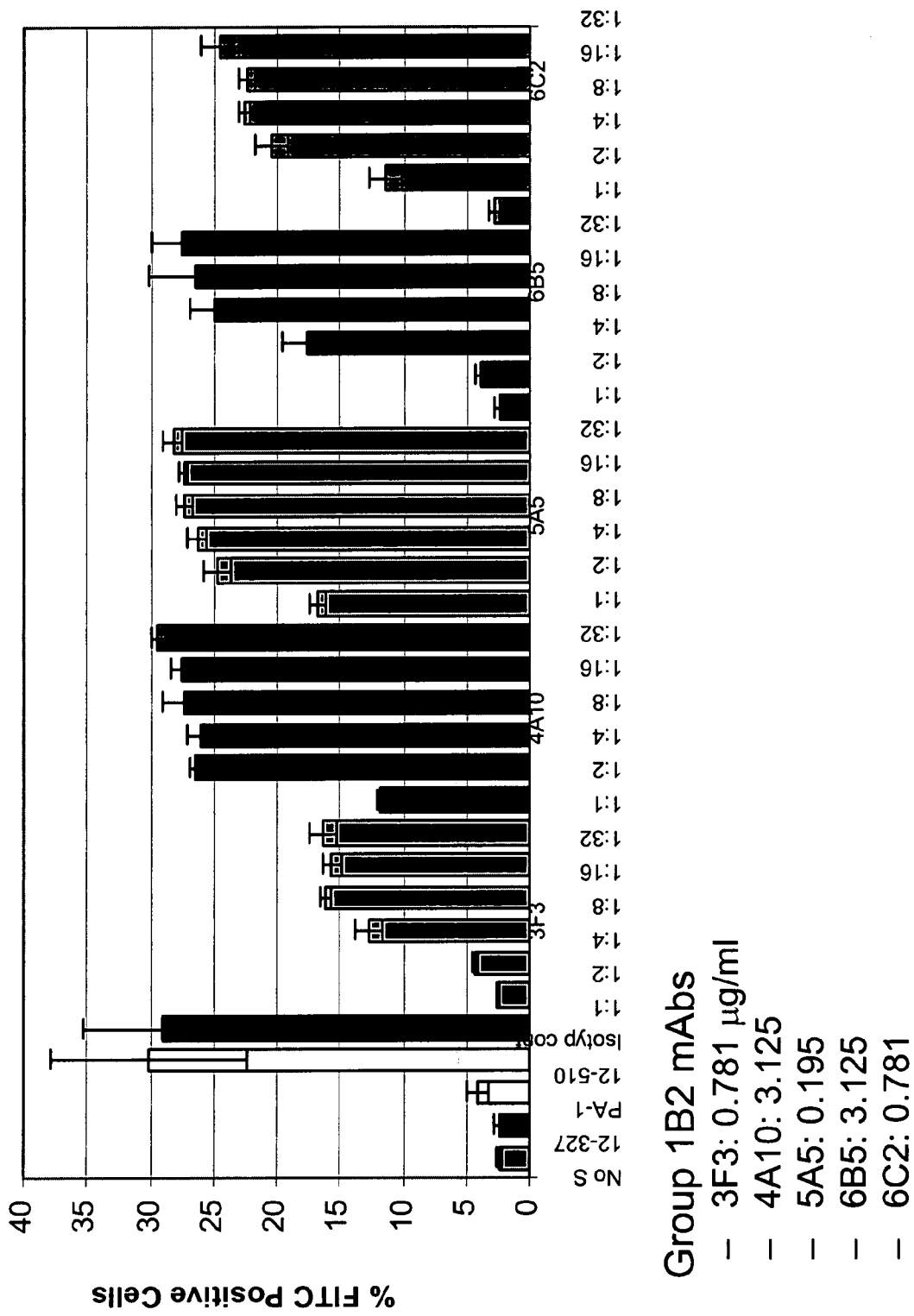
Figure 5D:
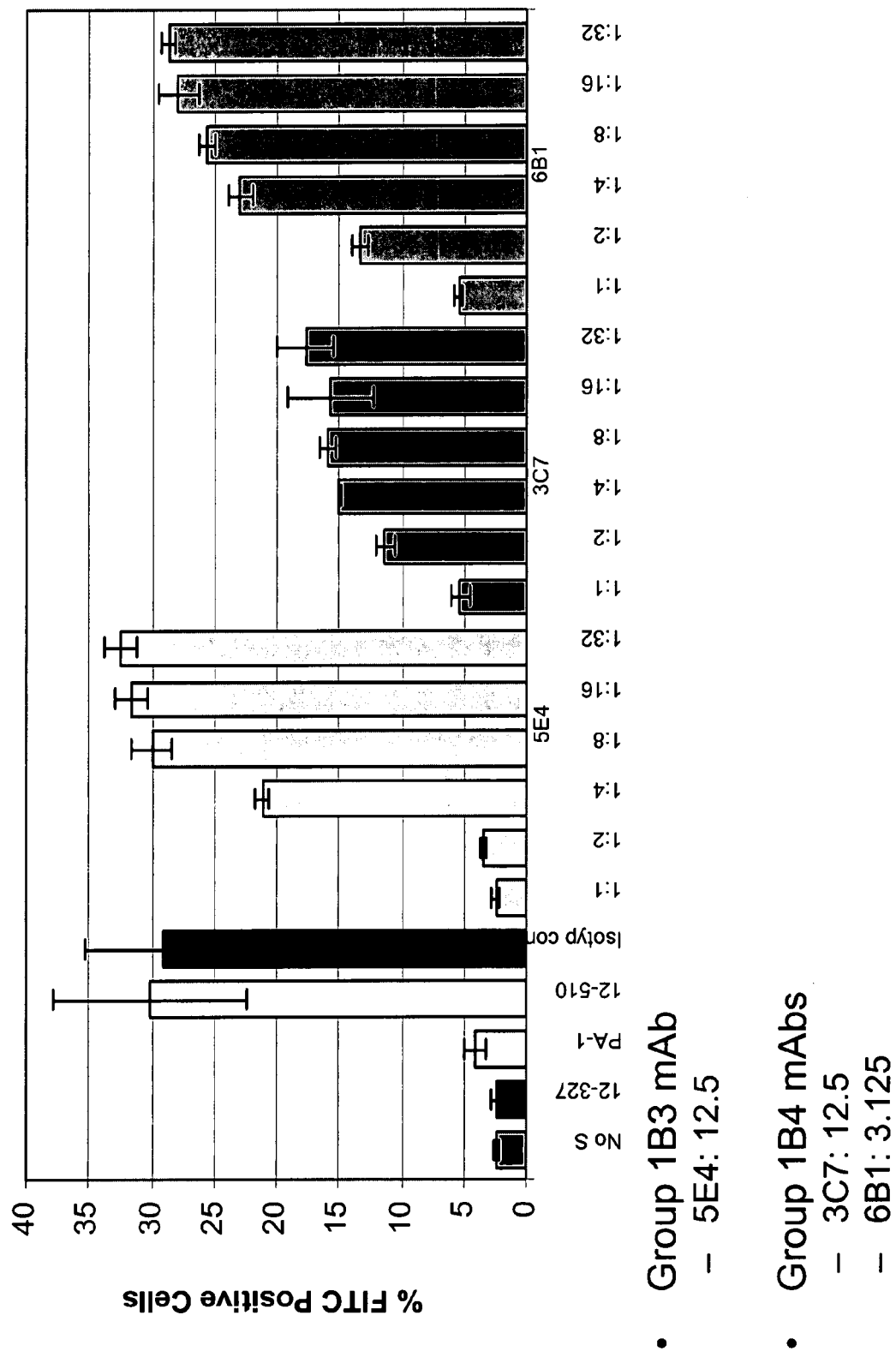
Figure 5E:
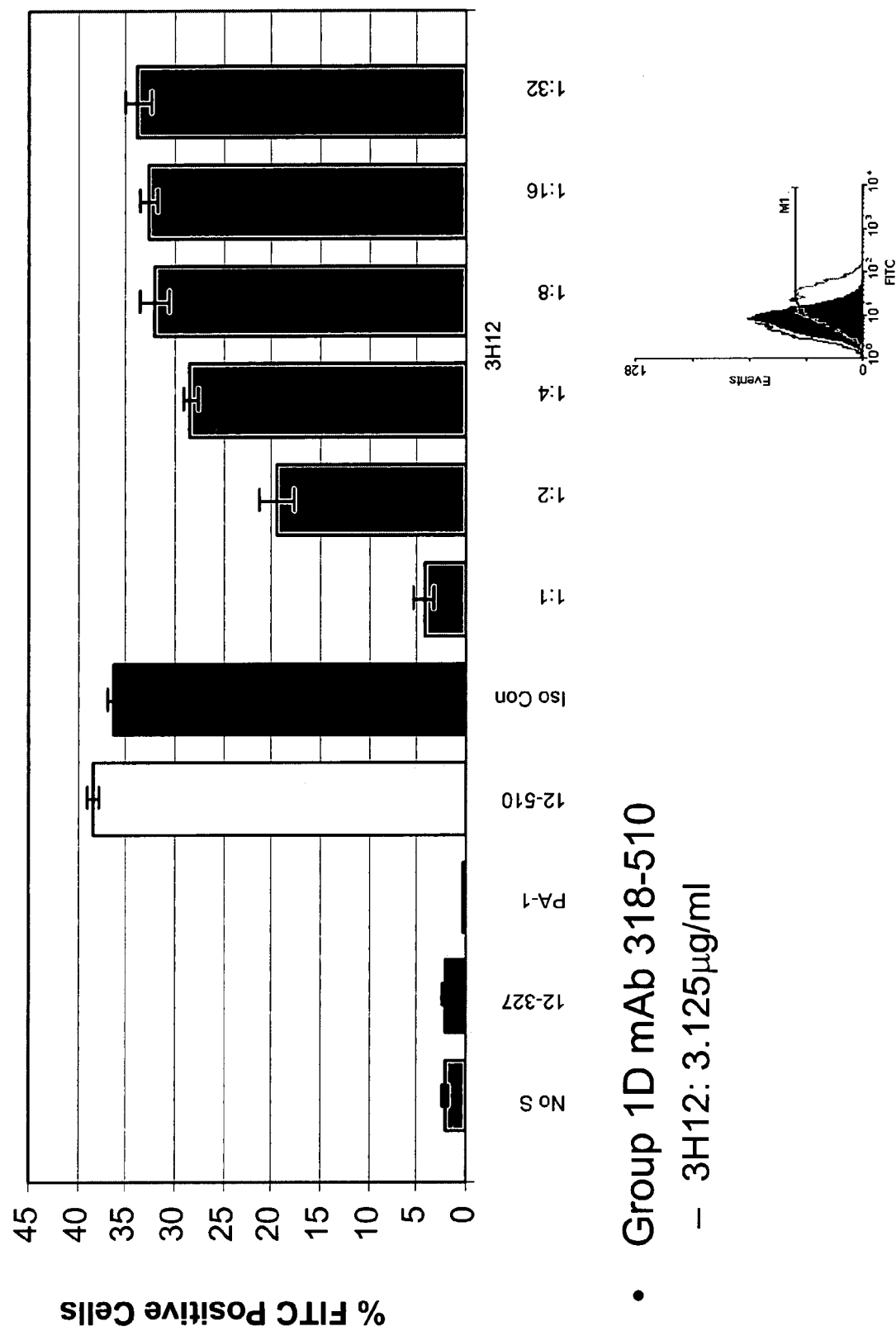

Neutralizing HmAbs were then cloned by limiting dilution and 24 out of 27 antibodies were purified by protein A/G affinity columns, 19 of these were subsequently confirmed as monoclonal by Ig gene sequencing. Following purification, the reactivity of HmAbs was re-tested against the 318-510 fragment, or 12-510 of the S1-Ig for those that failed to bind to 318-510. The range and pattern of reactivity noted in the initial screening was maintained after the purification of HmAbs. Most HmAbs demonstrated a dose dependent binding in which OD values decreased with increasing dilution of the antibody. Other Abs, such as 6B5 and 3H12, maintained high OD values indicating their relative high affinity. Often, the degree of reactivity in ELISA did not correlate with the neutralization titer (FIG. 3 and Table 3). This perhaps suggests limited availability of relevant epitopes in the virally expressed native S protein relative to their availability in a particular recombinant S1-Ig fragment, thus limiting neutralizing ability of certain HmAbs.

Different dilutions of purified HmAbs were tested for their ability to neutralize $200TCID_{50}$ of SARS-CoV. The titer of the antibody was defined as the lowest concentration of HmAb capable of neutralizing $200TCID_{50}$ of SARS-CoV. The HmAbs varied in their neutralizing potential. Some HmAbs neutralized the virus at concentrations as low as 0.195 µg/ml. However, some HmAbs could not neutralize virus below a concentration of 12.5 µg/ml (Table 3). This variance in neutralizing ability between HmAbs may be due to differences in affinities, fine binding specificities and/or the extent of availability of the targeted epitope on virally expressed native S protein.

Hybridomas that were positive for the production of neutralizing antibodies were cloned by limiting dilution and the clones were cultured to produce larger quantities of human monoclonal antibodies. Supernatants from these hybridomas were purified using Protein A/G affinity columns.

EXAMPLE V

Ig gene Utilization in the Human Anti-SARS-CoV Monoclonal Antibodies

Each of the purified HmAbs was sequenced, and previous group designations now can be further divided based on the sequence data suggesting that there are at least 10 different binding specificities among the panel of HmAbs. Unique binding specificities were deduced from the usage of different V and J, and also D gene sequences in the case of heavy chains. There is preferential usage of A30, JK4 rearrangement in the light chain and the VH1-2, D3-10, JH4B rearrangement in the heavy chain. However, several other V(D)J segments were also used (Table 3). Group 1B for example can be divided into likely four different specificities based on different V(D)J usage in the heavy and light chains.

The CDR3 region is formed by the heavy and light chain and is particularly important in determining binding specificity of Abs. Our data demonstrate sequence differences within the CDR3 regions of 4A10 and 4G2 although they both contain the same heavy and light chain genes and both fall into group 1A. Differences seen in the CDR3 region of the heavy chain may be responsible for the higher neutralizing titer of 4G2 by allowing better binding affinity and/or specificity. Two HmAbs showed changes in the CDR1 and CDR2 regions. Although these regions are not as important as the CDR3 region in determining binding specificity they do contribute to the overall binding specificity of the antibody. Therefore, changes within these regions may also affect binding specificity and/or affinity. For example, 4G2 and 6C1 have three amino acid differences within the CDR1 as compared to 4E2 although they all fall into group 1A and have the same V(D)J usage (FIG. 4). Though all antibodies seem to bind within the 318-510 RBD, small changes in amino acid sequence may alter the fine specificity and/or affinity of their binding. HmAb 6B1 has a single amino acid change in the CDR2 region when compared to 3C7; again this change may alter the affinity of 6B1 for the binding region within the S protein (FIG. 4).

Total RNA was purified from approximately $10^5$ hybridoma cells using an RNEASY™ Mini Kit Qiagen (Mississauga, Ontario) as per the manufacturer's instructions. The PCR amplification protocol and primers have previously been described (33, 34). Primers specific for the Ig variable (V) gene family members were pooled or used individually. Sequencing was performed by Lone Star Labs (Houston, Tex.) using the BIGDYE™ Terminator Version 3.0 DNA sequencing kit (Applied Biosystems, Foster City, Calif.) and ABI 3730 or 3100 automated sequencers (Applied Biosystems, Foster City, Calif.).

EXAMPLE VI

Receptor Binding Inhibition of the Human Anti-SARS-CoV Monoclonal Antibodies To understand the mechanism of neutralizing action of the human anti-SARS-CoV monoclonal antibodies, we used a receptor binding inhibition assay determine whether the antibodies inhibit receptor binding and thereby neutralize the virus. The assay was performed by preincubating the antibodies with an S1 fragment (aa 12-510) carrying an IgG1 Fc tag, incubating the mixture with VeroE6 cells expressing S protein receptor, and measuring the percentage of fragment bound cells using flow cytometry via an anti-human IgG FITC tagged secondary antibody. The antibodies were preincubated (starting concentration 10 µg/ml and 1:2 serial dilutions of Ab thereafter) with the S1 protein fragment (10 µg/ml, remains constant) for 1 hour at 4C. If the antibodies prevented binding of the S protein to Ace2, then there was a decrease in the fluorescent signal as measured by anti-human IgG FITC because unbound protein and antibody was washed away during the experiment.

Eighteen of the nineteen neutralizing antibodies tested reduced S protein binding to cells that were positive for the SARS receptor (FIGS. 5A-5F). All of the antibodies that bind to S protein in the region of aa 318-510 reduced receptor binding.

Of the two antibodies that bind upstream of the RBD, one inhibited receptor binding (1B5) and the second did not, and may even slightly enhance binding (4D4).

EXAMPLE VII

Analysis of Epitopes of the Human Anti-SARS-CoV Monoclonal Antibodies

Neutralizing human anti-SARS-CoV monoclonal antibodies were assayed under native or denatured conditions to determine if they recognized conformational or linear epitopes. At least five antibodies appeared to recognize conformational epitopes (Table 4).

EXAMPLE VIII

Pseudotyping Assay

We are establishing a pseudotyping assay in order to test neutralizing antibodies against changes seen in the S protein during an outbreak. An HIV core (HIV-deltaE-GFP) that expresses GFP is used so transfection efficiency during the production of the pseudovirus and infection by the pseudovirus can be measured using the GFP reporter. The mutations that are found in the S protein are introduced and tested to determine if these antibodies can inhibit entry of the pseudotyped virus. In addition, the pseudotyped virus is used to assay the antibodies for inhibition of fusion.

Cited Documents
1. Baker, S. C. 2004. Coronaviruses from common colds to severe acute respiratory syndrome. Pediatr. Infect. Dis. J. 23: 1049-1050.
2. Berry, J. D., S. Jones, M. A. Drebot, A. Andonov, M. Sabara, X. Y. Yuan, H. Weingartl, L. Fernando, P. Marszal, J. Gren, B. Nicolas, M. Andonova, F. Ranada, M. J. Gubbins, T. B. Ball, P.Kitcdhing, Y. Li, A. Kabani, F. Plummer. 2004. Development and characterization of neutralizing monoclonal antibody to the SARS-coronavirus. J. Virol. Methods. 120: 87-96.
3. Bisht, H. A. Roberts, L. Vogel, A. Bukreyev, P. L. Collins, B. R. Murphy, K. Subbarao, and B. Moss. 2004. Severe acute respiratory syndrome coronavirus spike protein expressed by attenuated vaccinia virus protectively immunizes mice. Proc. Natl. Acad. Sci. USA. 101: 6641-6646.
4. Buchholz, U., A. Bukreyev, L. Yang, E. W. Lamirande, B. R. Murphy, K. Subbarao, and P. L. Collins. 2004. Contributions of the structural proteins of severe acute respiratory syndrome to protective immunity. Proc. Natl. Acad. Sci. USA. 101: 9804-9809.
5. Chan, P. K. S., J. W. Tang, and D. S. C. Hui. 2006. SARS: clinical presentation, transmission, pathogenesis and treatment options. Clin. Sci. 110: 193-204.
6. Chen, Y. R. Wong, Y. O. Y. Soo, W. S. Wong, C. K. Lee, M. H. L. Ng, P. Chan, K. C. Wong, C. B Leung, G. Cheng. 2005. Use of convalescent plasma therapy in SARS patients in Hong Kong. Eur J Clin Microbiol. 24: 44-46.
7. Davis, C. G., X. Jia, X. Feng, and M. Haak-Frendscho. 2004. Production of human antibodies from transgenic mice. Methods Mol. Biol. 248: 191-200.
8. Gallo M. L., V. E. Ivanov, A. Jakobovits, C. G. Davis. 2000. The human immunoglobulin loci introduced into mice: V (D) and J gene segment usage similar to that of adult humans. Eur. J. Immunol. 30: 534-40.
9. Greenough, T. C., G. J. Babcock, A. Roberts, H. J. Hernandez, W. D. Thomas Jr, J. A. Coccia, R. F. Graziano, M. Srivivasan, I. Lowy, R. W. Finberg, K. Subbarao, L. Vogel, M. Somasundaran, K. Luzuriaga, J. L. Sullivan, and D. M. Abrosiono. 2005. Development and characterization of a Severe Acute Respiratory Syndrome-associated coronavirus-neutralizing human monoclonal antibody that provides effective immunoprophylaxis in mice. J. Infec. Dis. 191: 507-514.
10. Hanauer S. B., D. H. Present. 2003. The state of the art in the management of inflammatory bowel disease. Rev. Gastroenterol. Disord. 3: 81-92
11. He, Y., H. Lu, P. Siddiqui, Y. Zhou, and S. Jiang. 2005. Receptor-binding domain of severe acute respiratory syndrome coronavirus spike protein contains multiple conformation-dependent epitopes that induce highly potent neutralizing antibodies. J. Immunol. 174: 4908-4915.
12. He, Y., Q. Zhou, S. Liu, Y. Zhou, B. Yang, J. Li, S. Jiang. 2005. Identification of a critical neutralization determinant of severe acute respiratory syndrome (SARS)-associated coronavirus: importance for designing SARS vaccines. Virology. 334: 74-82.
13. He, Y., Y. Zhou, S. Liu, Z. Kou, W. Li, M. Farzan, S. Jiang. 2004. Receptor-binding domain of SARS-CoV spike protein induces highly potent neutralizing antibodies: implication for developing subunit vaccine. Biochem. Biophys. Res. Commun. 324: 773-781.
14. Hofmann, H. K., Hattermann, A. Marzi, T. Gramberg, M. Geier, M. Krumbiegel, S. Kuate, K. Uberla, M. Niedrig, and S. Pohlmann. 2004. S protein of severe acute respiratory syndrome-associated coronavirus mediates entry into hepatoma cell lines and is targeted by neutralizing antibodies in infected patients. J. Virol. 78: 6134-6142.
15. Huang S., L. Mills, B. Mian, C. Tellez, M. McCarty, X. D. Yang, J. M. Gudas, M. Bar-Eli. 2002. Fully humanized neutralizing Abs to interleukin-8 (ABX-IL8) inhibits angiogenesis, tumor growth, and metastasis of human melanoma. Am. J. Pathol. 161: 125-34.
16. Li, F. W. Li, M. Farzan, S. C. Harrison. 2005. Structure of SARS coronavirus spike receptor-binding domain complexed with receptor. Science. 309: 1864-1868.
17. Li, W., M. J. Moore, N. Vasilieva, J. Sui, S. K. Wong, M. A. Berne, M. Somasudaran, J. L. Sullivan, K. Luzuriaga, T. C. Greenough, H. Choe, and M. Farzan. 2003. Angiotensin-converting enzyme 2 is a functional receptor for the SARS coronavirus. Nature. 426: 450-454.
18. Li, W., Z. Shi, M. Yu, W. Ren, C. Smith, J. H. Epstein, H. Wang, G. Crameri, Z. Hu, H. Zhang, J. Zhang, J. McEachern, H. Field, P. Daszak, B. T. Eaton, S. Zhang, L. Wang. 2005. Bats are the natural reservoirs of SARS-like coronaviruses. Science. 310: 676-679.
19. Lonberg, N. 2005. Human antibodies from transgenic animals. Nat. Biotechnol. 23: 1117-1125.
20. Marks J. D., M. Tristem, A. Karpas, G. Winter. 1991. Oligonucleotide primers for polymerase chain reaction amplification of human immunoglobulin variable genes and design of family-specific oligonucleotide probes. Eur. J. Immunol. 21: 980-91.
21. Piedimonte G., K. A. King, N. L. Holmgren, P. J. Bertrand, M. M. Rodriguez, R. L Hirsch. 2000. A humanized monoclonal antibody against respiratory syncytial virus (palivizumab) inhibits RSV-induced neurogenic-mediated inflammation in rat airways. Pediatr. Res. 47: 351-6.
22. Peiris, J. S. M. and K. Y. Yuen. 2004. Severe acute respiratory syndrome. Nat. Med. 10: S88-S97.
23. Rathanaswami P., S. Roalstad, L. Roskos, Q. J. Su, S. Lackie, J. Babcook. 2005. Demonstration of an in vivo generated sub-picomolar affinity fully human monoclonal antibody to interleukin-8. Biochem. Biophys. Res. Commun. 334: 1004-13.
24. Ross J. S., J. A. Fletcher, G. P. Linette, J. Stec, E. Clark, M. Ayers, W. F. Symmans, L. Pusztai, K. J. Bloom. 2003. The Her-2/neu gene and protein in breast cancer 2003: biomarker and target of therapy. Oncologist. 8: 307-25.
25. Subbarao, K., J. McAuliffe, L. Vogel, G. Fahle, S. Fischer, K. Tatti, M. Packard, U. Shieh, S. Zaki, and B. Murphy. 2004. Prior infection and passive transfer of neutralizing antibody prevent replication of severe acute respiratory syndrome coronavirus in the respiratory tract of mice. J. Virol. 78: 3572-3577.
26. Sui, J., W. Li, A. Murakami, A. Tamin, L. J. Matthews, S. K. Wong, M. J. Moore, A. St. Clair Tallarico, M. Olurinde, H. Choe, L. J. Anderson, W. J. Bellini, M. Farzan, and W. A. Marasco. 2004. Potent neutralization of severe acute respiratory syndrome (SARS) coronavirus by a human mAb to S1 protein that blocks receptor association. Proc. Natl. Acad. Sci. USA. 101:2 536-2541.
27. Sui, J., W. Li, A. Roberts, L. J. Matthews, A. Murakami, L. Vogel, S. K. Wong, K. Subbarao, M. Farzan, and W. A. Marasco. 2005. Evaluation of human monoclonal antibody 80R for immunoprophylaxis of severe acute respiratory syndrome by an animal study, epitope mapping, and analysis of spike variants. J. Virol. 79: 5900-5906.
28. The Chinese SARS Molecular Epidemiology Consortium. 2004. Molecular evolution of the SARS coronavirus during the course of the SARS epidemic in China. Science. 303: 1666-1669.
29. Traggiai, E., S. BGecker, K. Subbarao, L. Kolesnikova, Y. Uematsu, M. R. Gismondo, B. R. Murphy, R. Rappuoli, and A. Lanzavecchia. 2004. An efficient method to make human monoclonal antibodies from memory B cells: potent neutralization of SARS coronavirus. Nat. Med. 10: 871-875.
30. Wong, S. K., W. Li, M. J. Moore, H. Choe, and M. Farzan. 2004. A 193-amino acid fragment of the SARS coronavirus S protein efficiently binds angiotensin-converting enzyme 2. J. Biol. Chem. 279: 3197-3201.
31. Yang, Z, W. Kong, Y. Huang, A. Roberts, B. R. Murphy, K. Subbarao, and G. Nabel. 2004. A DNA vaccine induces SARS coronavirus neutralization and protective immunity in mice. Nature. 428: 561-564.
32. Yang, Z., H. C. Werner, W. Kong, K. Leung, E. Traggiai, A. Lanzavecchia, and G. J. Nabel. 2005. Evasion of antibody neutralization in emerging severe acute respiratory syndrome coronaviruses. Proc. Natl. Acad. Sci. USA. 102: 797-801.
33. Yi, C. E., L. Ba, L. Zhang, D. D. Ho, and Z. Chen. 2005. Single amino acid substitutions in the severe acute respiratory syndrome coronavirus spike glycoprotein determine viral entry and immunogenicity of a major neutralizing domain. J. Virol. 79: 11638-11646.
34. Zhang, H., G. Wang, J. Li, Y. Nie, X. Shi, G. Lian, W. Wang, X. Yin, Y. Zhao, X. Qu, M. Ding, and H. Deng. 2004. Identification of an antigenic determinanat on the S2 domain of the severe acute respiratory syndrome coronavirus spike glycoprotein capable of inducing neutralizing antibodies. J. Virol. 78: 6938-6945.

TABLE 1

Reactivity to the ectodomain of S protein determined by ELISA reactivity to recombinant S protein (a.a. 12-1193)

| Plate Breakdown | V5-S-HIS | V5-OVA-HIS |
|---|---|---|
| OD > 0.0 | 1152 | 1152 |
| 0.1 | 893 | 439 |
| 0.2 | 739 | 94 |
| 0.3 | 688 | 22 |
| 0.4 | 657 | 11 |
| 0.5 | 620 | 7 |
| 0.6 | 593 | 6 |
| 0.7 | 565 | 6 |
| 0.8 | 541 | 6 |
| 0.9 | 520 | 6 |
| 1.0 | 508 | 4 |
| 1.5 | 438 | 3 |
| 2.0 | 401 | 3 |
| 2.5 | 375 | 3 |
| 3.0 | 352 | 2 |
| 3.5 | 298 | 2 |
| 4.0 | 136 | 0 |

[a]numbers of positive reacting supernatants within OD value range at left as determined by ELISA

TABLE 2

Likely binding region of human hybridoma supernatants determined by ELISA reactivity with S1-IgG protein fragments

| ELISA reactivity | Group Designation | Number of Supernatants | Number Neutralizing | Likely Binding Region |
|---|---|---|---|---|
| All S1-IgG fragments | 1A | 13 | 9 | 318-510 |
| 12-672 | 3A | 1 | 0 | 510-672 |
| 12-672, 12-510 | 2A | 4 | 1 | 12-261 |
| 12-672, 12-510, 318-510 | 1B | 45 | 14 | 318-510 |
| 12-672, 261-672 | 3B | 2 | 0 | 510-672 |
| 12-510 | 2B | 29 | 2 | 12-261 |
| 12-510, 318-510 | 1C | 41 | 0 | 318-510 |
| 318-510 | 1D | 29 | 1 | 318-510 |
| Total | | 165 | 27 | |

Table 3. Summary of HmAbs reactivity, neutralizing titer and heavy (H) and light (L) chain usage.

TABLE 3

Summary of HmAbs reactivity, neutralizing titer and heavy (H) and light (L) chain usage.

| HmAb | Group | Reactivity S1-IgG (12-672, 12-510, 261672, 318510) | Binding region | Neutralizing titer 200TCID$_{50}$ (μg/mL) | H chain | L chain | H CDR3 | SEQ ID NO: | L CDR3 | SEQ ID NO: |
|---|---|---|---|---|---|---|---|---|---|---|
| 4-E2 | 1A1 | 0.019, 1.518, 0.551, 1.839 | 318-510 | 0.781 | VH1-2, D3-10, JH4B | A30, JK4 | GPHSFG-SGSYPFDY | 122 | QQYNS-YPLT | 129 |
| 4-G2 | 1A1 | 1.200, 1.662, 0.665, 1.811 | 318-510 | 0.781 | VH1-2, D3-10, JH4B | A30, JK4 | GPHSFG-SGSYPFDY | 122 | QQYNS-YPLT | 129 |
| 6-C1 | 1A1 | 1.226, 1.586, 0.649, 2.405 | 318-510 | 0.781 | VH1-2, D3-10, JH4B | A30, JK4 | GPHSFG-SGSYPFDY | 122 | QQYNS-YPLT | 129 |
| 3-A7 | 1B1 | 1.307, 1.523, 0.379, 1.964 | 318-510 | 0.195 | VH1-18, D1-26, JH4B | A30, JK4 | GRYLDY | 123 | LQYNS-YPLT | 130 |
| 5-A7 | 1B1 | 1.111, 1.449, 0.366, 1.997 | 318-510 | 0.781 | VH1-18, D1-26, JH4B | A30, JK4 | GRYLDY | 123 | LQYNS-YPLT | 130 |
| 5-D3 | 1B1 | 0.968, 1.316, 0.403, 2.020 | 318-510 | 0.195 | VH1-18, D1-26, JH4B | A30, JK4 | GRYLDY | 123 | LQYNS-YPLT | 130 |
| 5-D6 | 1B1 | 0.747, 1.313, 0.355, 2.117 | 318-510 | 0.195 | VH1-18, D1-26, JH4B | A30, JK4 | GRYLDY | 123 | LQYNS-YPLT | 130 |
| 6-B8 | 1B1 | 1.045, 1.704, 0.497, 2.133 | 318-510 | 0.781 | VH1-18, D1-26, JH4B | A30, JK4 | GRYLDY | 123 | LQYNS-YPLT | 130 |
| 4-A10 | 1B2 | 1.013, 1.524, 0.567, 1.792 | 318-510 | 3.125 | VH1-2, D3-10, JH4B | A30, JK4 | GPHTFG-SGSYPFDY | 124 | QQYNS-YPLT | 129 |
| 6-C2 | 1B2 | 1.005, 1.603, 0.586, 1.849 | 318-510 | 0.781 | VH1-2, D3-10, JH4B | A30, JK4 | GPHTFG-SGSYPFDY | 124 | QQYNS-YPLT | 129 |
| 3-F3 | 1B2 | 1.075, 1.349, 0.325, 1.887 | 318-510 | 0.781 | VH1-2, D3-10, JH4B | A30, JK4 | GPHTFG-SGSYPFDY | 124 | QQYNS-YPLT | 129 |
| 5-A5 | 1B2 | 0.986, 1.187, 0.337, 2.310 | 318-510 | 0.195 | VH1-2, D3-10, JH4B | A30, JK4 | GPHTFG-SGSYPFDY | 124 | QQYNS-YPLT | 129 |
| 6-B5 | 1B2 | 1.040, 1.324, 0.430, 2.087 | 318-510 | 3.125 | VH1-2, D3-10, JH4B | A30, JK4 | GPHTFG-SGSYPFDY | 124 | QQYNS-YPLT | 129 |
| 5-E4 | 1B3 | 0.735, 1.199, 0.298, 2.275 | 318-510 | 12.5 | VH1-2, N/A, JH4B | A30, JK5 | GRYLDY | 123 | LQYNS-YPIT | 131 |
| 3-C7 | 1B4 | 1.092, 1.422, 0.357, 2.193 | 318-510 | 12.5 | VH3-33, D2-2, JH4B | L5, JK4 | DPLGYC-SSTSCS-YFDY | 125 | QQANN-FPLT | 132 |
| 6-B1 | 1B4 | 1.128, 1.166, 0.369, 2.093 | 318-510 | 3.125 | VH3-33, D2-2, JH4B | L5, JK4 | DPLGYC-SSTSCS-YFDY | 125 | QQANN-FPLT | 132 |
| 3-H12 | 1D | 0.185, 0.318, 0.090, 1.304 | 318-510 | 3.125 | VH4-59, D3-9, JH6B | A30, JK3 | DYDILT-GYSNYY-GMDV | 126 | LQHNS-YPFT | 133 |
| 4-D4 | 2B1 | 0.258, 0.761, 0.103, 0.101 | 12-261 | 12.5 | VH3-33, D4-17, JH4B | A1, JK2 | GGDGER-FDY | 127 | MQGTH-WPPYVQ | 134 |
| 1-B5 | 2B2 | 0.463, 1.292, 0.110, 0.191 | 12-261 | 0.195 | VH3-33, N/A JH5B | A30, JK4 | GDFYWF-DP | 128 | QQYNS-YPLT | 129 |

TABLE 4

Evaluation of epitope type for selected neutralizing human anti-SARS-CoV monoclonal antibodies

| | Native | | | | | | Denatured | | | | | |
|---|---|---|---|---|---|---|---|---|---|---|---|---|
| | 1G3 | 5C12 | 2B10 | 2E8 | 5E1 | Cont | 1G3 | 5C12 | 2B10 | 2E8 | 5E1 | Cont |
| 10 μg/ml | 1.378 | 1.242 | 1.562 | 1.426 | 1.231 | 0.738 | 0.062 | 0.069 | 0.062 | 0.049 | 0.094 | 0.146 |
| | 1.315 | 1.308 | 1.615 | 1.379 | 1.197 | 0.587 | 0.053 | 0.062 | 0.061 | 0.07 | 0.076 | 0.157 |
| 1:5 | 1.348 | 1.066 | 1.608 | 1.225 | 1.071 | 0.052 | 0.059 | 0.058 | 0.057 | 0.053 | 0.054 | 0.06 |
| | 1.276 | 1.137 | 1.53 | 1.184 | 1.199 | 0.049 | 0.053 | 0.053 | 0.056 | 0.065 | 0.049 | 0.045 |
| 1:25 | 0.91 | 1.053 | 1.107 | 0.921 | 0.828 | | 0.052 | 0.051 | 0.054 | 0.05 | 0.045 | |
| | 1.051 | 0.499 | 1.077 | 0.999 | 0.687 | | 0.051 | 0.055 | 0.065 | 0.052 | 0.046 | |
| 1:125 | 0.322 | 0.337 | 0.385 | 0.4 | 0.264 | | 0.054 | 0.05 | 0.051 | 0.047 | 0.04 | |
| | 0.298 | 0.161 | 0.395 | 0.342 | 0.251 | | 0.048 | 0.043 | 0.039 | 0.054 | 0.035 | |

ANTIBODY SEQUENCES

SEQ ID NO: 1
Antibody 5D6 Nucleotide sequence of heavy chain variable region
5'CAGGTTCAGCTGGTGCAGTCTGGAGCTGAGGTGAAGAAGCCTGGGGCC
TCAGTGAAGGTCTCCTGCAAGGCTTCTGGTTACACCTTTACCAGCTATGG
TATCAGCTGGGTGCGACAGGCCCCTGGACAAGGGCTTGAGTGGATGGGAT
GGATCAGCGCTTATAATGGTAACACAAACTATGCACAGAAGCTCCAGGGC
AGAGTCACCATGACCACAGACACATCCACTAACACAGCCTACATGGAGCT
GAGGAGCCTGAGATCTGACGACACGGCCGTGTATTACTGTGCGGTTGGGA
GGTACCTTGACTACTGGGGCCAGGGAACCCTGGTCACCGTCTCCTCA3'

SEQ ID NO: 2
Antibody 5D6 Amino acid sequence of heavy chain variable region
QVQLVQSGAEVKKPGASVKVSCKASGYTFTSYGISWVRQAPGQGLEWMGW
ISAYNGNTNYAQKLQGRVTMTTDTSTNTAYMELRSLRSDDTAVYYCAVGR
YLDYWGQGTLVTVSS SEQ ID NO: 3
Antibody 5D6 Nucleotide sequence of light chain variable region
5'GACATCCAGATGACCCAGTCTCCATCCTCCCTGTCTGCATCTGTAGGA
GACAGAGTCACCATCACTTGCCGGGCAAGTCAGGACATTAGAAATGATTT
AGGCTGGTATCAGCAGAAACCAGGGAAAGCCCCTAAGCGCCTGATCTATG
CTGCATCCAGTTTGCAAAGTGGGGTCCCATCAAGGTTCAGCGGCAGTGGA
TCTGGGACAGAATTCACTCTCACAATCAGCAGCCTGCAGCCTGAAGATTT
TGCAACTTATTACTGTCTACAGTATAATAGTTACCCTCTCACTTTCGGCG
GAGGGACCAAGGTGGAGATCAAA3'

SEQ ID NO: 4
Antibody 5D6 Amino acid sequence of light chain variable region
DIQMTQSPSSLSASVGDRVTITCRASQDIRNDLGWYQQKPGKAPKRLIYA
ASSLQSGVPSRFSGSGSGTEFTLTISSLQPEDFATYYCLQYNSYPLTFGG
GTKVEIK SEQ ID NO: 5
Antibody 5D3 = 6B8 = 3A7 = 5A7 = 2E8.1 = 2E8.2 = 5D1.2 Nucleotide sequence of heavy chain variable region
5'CAGGTTCAGCTGGTGCAGTCTGGAGCTGAGGTGAAGAAGCCTGGGGCC
TCAGTGAAGGTCTCCTGCAAGGCTTCTGGTTACACCTTTACCAGCTATGG
TATCAGCTGGGTGCGACAGGCCCCTGGACAAGGTCTTGAGTGGATGGGAT
GGATCAGCGCATATAATGGTAACACAAACTATGCACAGAAGCTCCAGGGC
AGAGTCACCATGACCACAGACACATCCACGAGCACAGCCTACATGGAGCT
GAGGAGCCTGAGATCTGACGACACGGCCGTGTATTACTGTGCGGTTGGGA
GGTACCTTGACTACTGGGGCCAGGGAACCCTGGTCACCGTCTCCTCA3'

SEQ ID NO: 6
Antibody 5D3 = 6B8 = 3A7 = 5A7 = 2E8.1 = 2E8.2 = 5D1.2 Amino acid sequence of heavy chain variable region
QVQLVQSGAEVKKPGASVKVSCKASGYTFTSYGISWVRQAPGQGLEWMGW
ISAYNGNTNYAQKLQGRVTMTTDTSTSTAYMELRSLRSDDTAVYYCAVGR
YLDYWGQGTLVTVSS SEQ ID NO: 7
Antibody 5D3 = 6B8 = 3A7 = 5A7 = 2E8.1 = 2E8.2 = 5D1.2 Nucleotide sequence of light chain variable region
5'GACATCCAGATGACCCAGTCTCCATCCTCCCTGTCTGCATCTGTAGGA
GACAGAGTCACCATCACTTGCCGGGCAAGTCAGGACATTAGAAATGATTT
AGGCTGGTATCAGCAGAAACCAGGGAAAGCCCCTAAGCGCCTGATCTATG
CTGCATCCAGTTTGCAAAGTGGGGTCCCATCAAGGTTCAGCGGCAGTGGA
TCTGGGACAGAATTCACTCTCACAATCAGCAGCCTGCAGCCTGAAGATTT
TGCAACTTATTACTGTCTACAGTATAATAGTTACCCTCTCACTTTCGGCG
GAGGGACCAAGGTGGAGATCAAA3'

SEQ ID NO: 8
Antibody 5D3 = 6B8 = 3A7 = 5A7 = 2E8.1 = 2E8.2 = 5D1.2 Amino acid sequence of light chain variable region
DIQMTQSPSSLSASVGDRVTITCRASQDIRNDLGWYQQKPGKAPKRLIYA
ASSLQSGVPSRFSGSGSGTEFTLTISSLQPEDFATYYCLQYNSYPLTFGG
GTKVEIK SEQ ID NO: 9
Antibody 5E4 Nucleotide sequence of heavy chain variable region
5'CAGGTACACCTGGTGCAGTCTGGGGCTGAGGTGAAGAAGCCTGGGGCC
TCAGTGAAGGTCTCCTGCAAGGCTTCTGGATACACCTTCACCGGCTACTA
TGTACACTGGGTGCGACAGGCCCCTGGACAGGGGCTTGAGTGGATGGGAT
GGATCAACCCTAACAGTGGTGGCACAAACTATGCACAGAAGTTTCAGGGC
AGGGTCACCATGACCAGGGACACGTCCATCAGCACAGCCTACATGGAGCT
GAGCAGGCTGAGATCTGACGACACGGCCGTGTATTTCTGTGCGGGTGGGC
GCTACTTGGACTACTGGGGCCAGGGAACCCTGGTCACCGTCTCCTCA3'

SEQ ID NO: 10
Antibody 5E4 Amino acid sequence of heavy chain variable region
QVHLVQSGAEVKKPGASVKVSCKASGYTFTGYYVHWVRQAPGQGLEWMGW
INPNSGGTNYAQKFQGRVTMTRDTSISTAYMELSRLRSDDTAVYFCAGGR
YLDYWGQGTLVTVSS SEQ ID NO: 11
Antibody 5E4 Nucleotide sequence of light chain variable region
5'GACATCCAGATGACCCAGTCTCCATCCTCCCTGTCTGCATCTGTAGGA
GACAGAGTCACCATCACTTGCCGGGCAAGTCAGGGCATTAGAAATGATTT
AGGCTGGTATCAGCAGAAACCAGGGAAAGCCCCTAAGCGCCTGATCTATG
CTGCATCCAGTTTGCAAAGTGGGGTCCCATCAAGGTTCAGCGGCAGCGGA
TCTGGGACAGAATTCACTCTCACAATCAGCAGCCTGCAGCCTGAAGATTT
TGCAACTTATTACTGTCTACAGTATAATAGTTACCCGATCACCTTCGGCC
AAGGGACACGACTGGAGATTAAA3'

SEQ ID NO: 12
Antibody 5E4 Amino acid sequence of light chain variable region
DIQMTQSPSSLSASVGDRVTITCRASQGIRNDLGWYQQKSGKAPKRLIYA
ASSLQSGVPSRFSGSGSGTEFTLTISSLQPEDFATYYCLQYNSYPITFGQ
GTRLEIK SEQ ID NO: 13
Antibody 5E1.1.1 = 5E1.2 = 5E1.3 Nucleotide sequence of heavy chain variable region
5'CAGGTGCAGCTGGTGCAGTCTGGGGCTGAGGTGAAGAAGCCTGGGGCC
TCAGTGAAGGTCTCCTGCAAGGCTTCTGGATACACCTTCACCGGCTACTA
TATGCACTGGGTGCGACAGGCCCCTGGACAAGGGCTTGAGTGGATGGGAT
GGATCAACCCTAACAGTGGTGGCACAAACTATGCACAGAAGTTTCAGGGC
AGGGTCACCATGACCAGGGACACGTCCATCAGCACAGCCTACATGGAGCT
GAGCAGGCTGAGATCTGACGACACGGCCGTGTTTTACTGTGCGGGTGGGA
CCTACTTGGACTACTGGGGCCAGGGAACCCTGGTCACCGTCTCCTCA3'

SEQ ID NO: 14
Antibody 5E1.1.1 = 5E1.2 = 5E1.3 Amino acid sequence of heavy chain variable region
QVQLVQSGAEVKKPGASVKVSCKASGYTFTGYYMHWVRQAPGQGLEWMGW
INPNSGGTNYAQKFQGRVTMTRDTSISTAYMELSRLRSDDTAVFYCAGGT
YLDYWGQGTLVTVSS SEQ ID NO: 15
Antibody 5E1.1.1 = 5E1.2 = 5E1.3 Nucleotide sequence of light chain variable region
5'GACATCCAGATGACCCAGTCTCCATCCTCCCTGTCTGCATCTGTAGGA
GACAGAGTCACCATCACTTGCCGGGCAAGTCAGGGCATTAGAAATGATTT
AGGCTGGTATCAGCAGAAACCAGGGAAAGCCCCTAAGCGCCTGATCTATG
CTGCATCCAGTTTGCAAAGTGGGGTCCCATCAAGGTTCAGCGGCAGTGGA
TCTGGGACAGAATTCACTCTCACAATCAGCAGCCTGCAGCCTGAAGATTT
TGCAACTTATTACTGTCTACAGTATAATAGTTACCCGATCACCTTCGGCC
AAGGGACACGACTGGAGATTAAA3'

SEQ ID NO: 16
Antibody 5E1.1.1 = 5E1.2 = 5E1.3 Amino acid sequence of light chain variable region
DIQMTQSPSSLSASVGDRVTITCRASQGIRNDLGWYQQKPGKAPKRLIYA
ASSLQSGVPSRFSGSGSGTEFTLTISSLQPEDFATYYCLQYNSYPITFGQ
GTRLEIK

ANTIBODY SEQUENCES

SEQ ID NO: 17
Antibody 5E1.1.2 Nucleotide sequence of heavy chain variable region
5'CAGGTGCAGCTGGTGCAGTCTGGGGCTGAGGTGAAGAAGCCTGGGGCC
TCAGTGAAGGTCTCCTGCAAGGCTTCTGGATACACCTTCACCGGCTACTA
TATGCACTGGGTGCGACAGGCCCCTGGACAAGGGCTTGAGTGGATGGGAT
GGATCAACCCTAACAGTGGTGGCACAAACTATGCACAGAAGTTTCAGGGC
AGGGTCACCATGACCAGGGACACGTCCATCAGCACAGCCTACATGGAGCT
GAGCAGGCTGAGATCTGACGACACGGCCCTGTTTTACTGTGCGGGTGGGA
CCTACTTGGACTACTGGGGCCAGGGAACCCTGGTCACCGTCTCCTCA3'

SEQ ID NO: 18
Antibody 5E1.1.2 Amino acid sequence of heavy chain variable region
QVQLVQSGAEVKKPGASVKVSCKASGYTFTGYYMHWVRQAPGQGLEWMGW
INPNSGGTNYAQKFQGRVTMTRDTSISTAYMELSRLRSDDTAVFYCAGGT
YLDYWGQGTLVTVSS SEQ ID NO: 19
Antibody 5E1.1.2 Nucleotide sequence of light chain variable region
5'GACATCGTGATGACCCAGTCTCCAGACTCCCTGGCTGTGTCTCTGGGC
GAGAGGGCCACCATCAACTGCAAGTCCAGCCAGAGTGTTTTATACAGCTC
CAACAATAAGAACTACTTAGCTTGGTACCAGCAGAAACCAGGACAGCCTC
CTAAGCTGCTCATTTACTGGGCATCTACCCGGGAATCCGGGGTCCCTGAC
CGATTCAGTGGCAGCGGGTCTGGGACAGATTTCACTCTCACCATCAGCAG
CCTGCAGGCTGAAGATGTGGCAGTTTATTACTGTCAGCAATATTATAGTA
CTCCTCGGACGTTCGGCCAAGGGACCAAGGTGGAAATCAAA3'

SEQ ID NO: 20
Antibody 5E1.1.2 Amino acid sequence of light chain variable region
DIVMTQSPDSLAVSLGERATINCKSSQSVLYSSNNKNYLAWYQQKPGQPP
KLLIYWASTRESGVPDRFSGSGSGTDFTLTISSLQAEDVAVYYCQQYYST
PRTFGQGTKVEIK SEQ ID NO: 21
Antibody 3F3 = 6C2 Nucleotide sequence of heavy chain variable region
5'CAGGTGCAACTGGTGCAGTCTGGGGCTGAGGTGAAGAAGCCTGGGGCC
TCAGTGAAGGTCTCCTGCAAGGCTTCTGGATACACCTTCACCGGCTACTA
TATGCACTGGGTGCGACAGGCCCCTGGACAAGGGCTTGAGTGGATGGGAT
GGATCAACCCTAACAGTGGTGGCACAAACTATGCACAGAAGTTTCAGGGC
AGGGTCACCATGACCAGGGACACGTCCATCAGCTCGGCCTACATGGAACT
GAGCAGCCTGAGATCTGACGACACGGCCGTTTATTACTGTGCGAGAGGGC
CCCATACCTTCGGTTCGGGGAGTTACCCCTTTGACTACTGGGGCCAGGGA
ACCCTGGTCACCGTCTCCTCA3'

SEQ ID NO: 22
Antibody 3F3 = 6C2 Amino acid sequence of heavy chain variable region
QVQLVQSGAEVKKPGASVKVSCKASGYTFTGYYMHWVRQAPGQGLEWMGW
INPNSGGTNYAQKFQGRVTMTRDTSISSAYMELSSLRSDDTAVYYCARGP
HTFGSGSYPFDYWGQGTLVTVSS SEQ ID NO: 23
Antibody 3F3 = 6C2 Nucleotide sequence of light chain variable region
5'GACATCCAGATGACCCAGTCTCCATCCTCCCTGTCTGCATCTGTAGGA
GACAGAGTCACCATCACTTGCCGGGCAAGTCAGGGCATTAGAAGTGATTT
AGGCTGGTATCAGCAGAGACCAGGGAACACCCCTAAGCGCCTGATCTATG
CTGCATCCAGTTTACAAAGTGGGGTCCCATCAAGGTTCAGCGGCAGTGGA
TCTGGGACAGAATTCACTCTCACAATCAGCAGCCTGCAGCCTGAAGATTT
TGCAACTTATTACTGTCAACAGTATAATAGTTACCCGCTCACTTTCGGCG
GAGGGACCAAGGTGGAGATCAAA3'

SEQ ID NO: 24
Antibody 3F3 = 6C2 Amino acid sequence of light chain variable region
DIQMTQSPSSLSASVGDRVTITCRASQGIRSDLGWYQQRPGNTPKRLIYA
ASSLSGVPSRFSGSGSGTEFTLTISSLQPEDFATYYCQQYNSYPLTFGGG
TKVEIK SEQ ID NO: 25
Antibody 6C1 = 4G2 = 5C12.2 Nucleotide sequence of heavy chain variable region
5'CAGGTGCAGCTGGTGCAGTCTGGGGCTGAGGTGAAGAAGCCTGGGGCC
TCAGTGAAGGTCTCCTGCAAGGCTTCTGGATTCCCCTTCACCGACTACTA
TATGCACTGGGTGCGACAGGCCCCTGGACAAGGGCTTGAGTGGATGGGAT
GGATCAACTCTAACAGTGGTGGCACAAACTATGCACAGAAGTTTCAGGGC
AGGGTCACCATGACCAGGGACACGTCCATCAGCACAGCCTACATGGAGCT
CAGCAGGCTGAGATCTGACGACACGGCCGTGTATTACTGTGCGAGAGGGC
CCCATTCCTTTGGTTCGGGGAGTTACCCCTTTGACTACTGGGGCCAGGGA
ACCCTGGTCACCGTCTCCTCA3'

SEQ ID NO: 26
Antibody 6C1 = 4G2 = 5C12.2 Amino acid sequence of heavy chain variable region
QVQLVQSGAEVKKPGASVKVSCKASGFPFTDYYMHWVRQAPGQGLEWMGW
INSNSGGTNYAQKFQGRVTMTRDTSISTAYMELSRLRSDDTAVYYCARGP
HSFGSGSYPFDYWGQGTLVTVSS SEQ ID NO: 27
Antibody 6C1 = 4G2 = 5C12.2 Nucleotide sequence of light chain variable region
5'GACATCCAGATGACCCAGTCTCCATCCTCCCTGTCTGCATCTGTAGGA
GACAGAGTCACCATCACTTGCCGGGCAAGTCAGGGCATTAGAAGTGATTT
AGGCTGGTATCAGCAGAGACCAGGGAAAACCCCTAAGCCCCTGATCTATG
CTGCATCCAGTTTGCAAAGTGGGGTCCCATCAAGGTTCAGCGGCAGTGGA
TCTGGGACAGAATTCACTCTCACAATCAGCAGCCTGCAGCCTGAAGATTT
TGCAACTTATTACTGTCAACAGTATAATAGTTACCCGCTCACTTTCGGCG
GAGGGACCAAGGTGGAGATCAAA3'

SEQ ID NO: 28
Antibody 6C1 = 4G2 = 5C12.2 Amino acid sequence of light chain variable region
DIQMTQSPSSLSASVGDRVTITCRASQGIRSDLGWYQQRPGKTPKRLIYA
ASSLQSGVPSRFSGSGSGTEFTLTISSLQPEDFATYYCQQYNSYPLTFGG
GTKVEIK SEQ ID NO: 29
Antibody 4E2 Nucleotide sequence of heavy chain variable region
5'CAGGTGCAGCTGGTGCAGTCTGGGGCTGAGGTGAAGAAGCCTGGGGCC
TCAGTGAAGGTCTCCTGCAAGGCTTCTGGATACACCTTCACCGGCTACTA
TATGCACTGGGTGCGACAGGCCCCTGGACAAGGGCTTGAGTGGATGGGAT
GGATCAACTCTAACAGTGGTGGCACAAACTATGCACAGAAGTTTCAGGGC
AGGGTCACCATGACCAGGGACACGTCCATCAGCACAGCCTACATGGAGCT
GAGCAGGCTGAGATCTGACGACACGGCCGTGTATTACTGTGCGAGAGGGC
CCCATTCCTTTGGTTCGGGAGTTACCCCTTTGACTACTGGGGCCAGGGA
ACCCTGGTCACCGTCTCCTCA3'

SEQ ID NO: 30
Antibody 4E2 Amino acid sequence of heavy chain variable region
QVQLVQSGAEVKKPGASVKVSCKASGYTFTGYYMHWVRQAPGQGLEWMGW
INSNSGGTNYAQKFQGRVTMTRDTSISTAYMELSRLRSDDTAVYYCARGP
HSFGSGSYPFDYWGQGTLVTVSS SEQ ID NO: 31
Antibody 4E2 Nucleotide sequence of light chain variable region
5'GACATCCAGATGACCCAGTCTCCATCCTCCCTGTCTGCATCTGTAGGA
GACAGAGTCACCATCACTTGCCGGGCAAGTCAGGGCATTAGAAGTGATTT
AGGCTGGTATCAGCAGAGACCAGGGAAAACCCCTAAGCGCCTGATCTATG
CTGCATCCAGTTTGCAAAGTGGGGTCCCATCAAGGTTCAGCGGCAGTGGA
TCTGGGACAGAATTCACTCTCACAATCAGCAGCCTGCAGCCTGAAGATTT
TGCAACTTATTACTGTCAACAGTATAATAGTTACCCGCTCACTTTCGGCG
GAGGGACCAAGGTGGAGATCAAA3'

SEQ ID NO: 32
Antibody 4E2 Amino acid sequence of light chain variable region
DIQMTQSPSSLSASVGDRVTITCRASQGIRSDLGWYQQRPGKTPKRLIYA
ASSLQSGVPSRFSGSGSGTEFTLTISSLQPEDFATYYCQQYNSYPLTFGG
GTKVEIK

ANTIBODY SEQUENCES

SEQ ID NO: 33
Antibody 5A5 = 4A10 Nucleotide sequence of heavy chain variable region
5'CAGGTGCAGCTGGTGCAGTCTGGGGCTGAGGTGAAGAAGCCTGGGGCC
TCAGTGAAGGTCTCCTGCAAGGCTTCTGGATACACCTTCACCGGCTACTA
TATGCACTGGGTGCGACAGGCCCCTGGACAAGGGCTTGAGTGGATGGGAT
GGATCAACCCTAACAGTGGTGGCACAAACTATGCACAGAAGTTTCAGGGC
AGGGTCACCATGACCAGGGACTCGTCCATCAGCACAGCCTACATGGAACT
GAGCAGGCTGAGATCTGACGACACGGCCGTGTATTACTGTGCGAGAGGGC
CCCATACCTTTGGTTCGGGGAGTTACCCCTTTGACTACTGGGGCCAGGGA
ACCCTGGTCCCCGTCTCCTCA3'

SEQ ID NO: 34
Antibody 5A5 = 4A10 Amino acid sequence of heavy chain variable region
QVQLVQSGAEVKKPGASVKVSCKASGYTFTGYYMHWVRQAPGQGLEWMGW
INPNSGGTNYAQKFQGRVTMTRDSSISTAYMELSRLRSDDTAVYYCARGP
HTFGSGSYPFDYWGQGTLVPVSS SEQ ID NO: 35
Antibody 5A5 = 4A10 Nucleotide sequence of light chain variable region
5'GACATCCAGTTGACCCAGTCTCCATCTTCCCTGTCTGCATCTGTAGGA
GACAGAGTCACCATCACTTGCCGGGCAAGTCAGGGCATTAGAAGTGATTT
AGGCTGGTATCAGCAGAGACCAGGGAAAACCCCTAAGCGCCTGATCTATG
CTGCATCCAGTTTGCAAAGTGGGGTCCCATCAAGGTTCAGCGGCAGTGGA
TCTGGGACAGAATTCACTCTCACAATCAGCAGCCTGCAGCCTGAAGATTT
TGCAACTTATTACTGTCAACAGTATAATAGTTACCCGCTCACTTTCGGCG
GAGGGACCAAGGTGGAGATCAAA3'

SEQ ID NO: 36
Antibody 5A5 = 4A10 Amino acid sequence of light chain variable region
DIQLTQSPSSLSASVGDRVTITCRASQGIRSDLGWYQQRPGKTPKRLIYA
ASSLQSGVPSRFSGSGSGTEFTLTISSLQPEDFATYYCQQYNSYPLTFGG
GTKVEIK SEQ ID NO: 37
Antibody 6B5 = 5C12.1 Nucleotide sequence of heavy chain variable region
5'CAGGTGCAGCTGGTGCAGTCTGGGGCTGAGGTGAAGAAGCCTGGGGCC
TCAGTGAAGGTCTCCTGCAAGGCTTCTGGATACACCTTCACCGGCTACTA
TATGCACTGGGTGCGACAGGCCCCTGGACAAGGGCTTGAGTGGATGGGAT
GGATCAACCCTAACAGTGGTGGCACAAACTATGCACAGAAGTTTCAGGGC
AGGGTCACCATGACCAGGGACACGTCCATCAGCACAGCCTACATGGAGCT
GAGCAGGCTGAGATCTGACGACACGGCCGTGTATTACTGTGCGGAGGGGC
CCCATACCTTTGGTTCGGGGAGTTACCCCTTTGACTACTGGGGCCAGGGA
ACCCTGGTCACCGTCTCCTCA3'

SEQ ID NO: 38
Antibody 6B5 = 5C12.1 Amino acid sequence of heavy chain variable region
QVQLVQSGAEVKKPGASVKVSCKJkSGYTFTGYYMHWVRQAPGQGLEWMG
WINPNSGGTNYAQKFQGRVTMTRDTSISTAYMELSRLRSDDTAVYYCARG
PHTFGSGSYPFDYWGQGTLVTVSS SEQ ID NO: 39
Antibody 6B5 = 5C12.1 Nucleotide sequence of light chain variable region
5'GACATCCAGATGACCCAGTCTCCATCCTCCCTGTCTGCATCTGTAGGA
GACAGAGTCACCATCACTTGCCGGGCAAGTCAGGGCATTAGAAGTGATTT
AGGCTGGTATCAGCAGAGACCAGGGAAAACCCCTAAGCGCCTGATCTATG
CTGCATCCAGTTTGCAAAGTGGGGTCCCATCAAGGTTCAGCGGCAGTGGA
TCTGGGACAGAATTCACTCTCACAATCAGCAGCCTGCAGCCTGAAGATTT
TGCAACTTATTACTGTCAACAGTATAATAGTTACCCGCTCACTTTCGGCG
GAGGGACCAAGGTGGAGATCAAA3'

SEQ ID NO: 40
Antibody 6B5 = 5C12.1 Amino acid sequence of light chain variable region
DIQMTQSPSSLSASVGDRVTITCRASQGIRSDLGWYQQRPGKTPKRLIYA
ASSLQSGVPSRFSGSGSGTEFTLTISSLQPEDFATYYCQQYNSYPLTFGG
GTKVEIK SEQ ID NO: 41
Antibody 1B5 Nucleotide sequence of heavy chain variable region
5'CAGGTGCAGCTGGTGGAGTCTGGGGGAGGCGTGGTCCAGCCTGGGAGG
TCCCTGAGACTCTCCTGTGCAGCGTCTGGATTCACCTTCAGTAGCTATGG
CATGCACTGGGTCCGCCAGGCTCCAGGCAAGGGGCTGGAGTGGGTGGCAG
TTATATGGTATGATGGAAGTAATAAATACTATGCAGACTCCGTGAAGGGC
CGATTCACCATCTCCAGAGACAATTCCAAGAACACGCTGTATCTGCAAAT
GAACAGCCTGAGAGCCGAGGACACGGCTGTGTATTACTGTGCGAGAGGGG
ACTTTTACTGGTTCGACCCCTGGGGCCAGGGAACCCTGGTCACCGTCTCC
TCA3'

SEQ ID NO: 42
Antibody 1B5 Amino acid sequence of heavy chain variable region
QVQLVESGGGVVQPGRSLRLSCAASGFTFSSYGMHWVRQAPGKGLEWVAV
IWYDGSNKYYADSVKGRFTISRDNSKNTLYLQMNSLRAEDTAVYYCARGD
FYWFDPWGQGTLVTVSS SEQ ID NO: 43
Antibody 1B5 Nucleotide sequence of light chain variable region
5'GACATCCAGATGACCCAGTCTCCATCTTCCCTGTCTGCATCTGTAGGA
GACAGAGTCACCATCACTTGCCGGGCAAGTCAGGGCATTAGAAGTGATTT
AGGCTGGTATCAGCAGAGACCAGGGAAAACCCCTAAGCGCCTGATCTATG
CTGCATCCAGTTTGCAAAGTGGGGTCCCATCAAGGTTCAGCGGCAGTGGA
TCTGGGACAGAATTCACTCTCACAATCAGCAGCCTGCAGCCTGAAGATTT
TGCAACTTATTACTGTCAACAGTATAATAGTTACCCGCTCACTTTCGGCG
GAGGGACCAAGGTGGAGATCAAA3'

SEQ ID NO: 44
Antibody 1B5 Amino acid sequence of light chain variable region
DIQMTQSPSSLSASVGDRVTITCRASQGIRSDLGWYQQRPGKTPKRLIYA
ASSLQSGVPSRFSGSGSGTEFTLTISSLQPEDFATYYCQQYNSYPLTFGG
GTKVEIK SEQ ID NO: 45
Antibody 2B10.1 = 2B10.2 = 2B10.3 Nucleotide sequence of heavy chain variable region
5'CAGGTGCAGCTGGTGCAGTCTGGGGCTGAGGTGAAGAAGCCTGGGGCC
TCAGTGAAGGTCTCCTGCAAGGCTTCTGGATACACCTTCACCGGCTACTA
TATGCACTGGGTGCGACAGGCCCCTGGACAAGGGCTTGAGTGGATGGGAT
GGATCAACCCTAACAGTGGTGGCACAAACTATGCACAGAAGTTTCAGAGC
AGGGTCACCATGACCAGGGACACGTCCATCAGCACAGCCTACATGGAGCT
GAGCAGGCTGAGATCTGACGACACGGCCGTGTATTACTGTGCGGGGGGGA
TGGGGGACGTCTGGGGCCAAGGGACCACGGTCACCGTCTCCTCA3'

SEQ ID NO: 46
Antibody 2B10.1 = 2B10.2 = 2B10.3 Amino acid sequence of heavy chain variable region
QVQLVQSGAEVKKPGASVKVSCKASGYTFTGYYMHWVRQAPGQGLEWMGW
INPNSGGTNYAQKFQSRVTMTRDTSISTAYMELSRLRSDDTAVYYCAGGM
GDVWGQGTTVTVSS SEQ ID NO: 47
Antibody 2B10.1 = 2B10.2 = 2B10.3 Nucleotide sequence of light chain variable region
5'GACATCCAGATGACCCAGTCTCCATCCTCCCTGTCTGCATCTGTAGGA
GACAGAGTCACCATCACTTGCCGGGCAAGTCAGGGCATTAGAAATGATTT
AGGCTGGTATCAGCAGAGACCAGGGAAAGCCCCTAAGCGCCTGATCTATG
CTGCATCCAGTTTGCAAAGTGGGGTCCCATCAAGGTTCAGCGGCAGTGGA
TCTGGGACAGAATTCACTCTCACAATCAGCAGCCTGCAGCCTGAAGATTT
TGCAACTTATTACTGTCTACAGTATAATAGTTACCCGTGGACGTTCGGCC
AAGGGACCAAGGTGGAAATCAAA3'

SEQ ID NO: 48
Antibody 2B10.1 = 2B10.2 = 2B10.3 Amino acid sequence of light chain variable region
DIQMTQSPSSLSASVGDRVTITCRASQGIRNDLGWYQQKPGKAPKRLIYA
ASSLQSGVPSRFSGSGSGTEFTLTISSLQPEDFATYYCLQYNSYPWTFGQ
GTKVEIK

ANTIBODY SEQUENCES

SEQ ID NO: 49
Antibody 2B10.4 Nucleotide sequence of heavy chain variable region
5'CAGGTGCAGCTGGTGGAGTCCGGGGGAGGCGTGGTCCAGCCTGGGAGG
TCCCTGAGACTCTCCTGTGCAGCGTCTGGATTCACCTTCAGTAGCTATGG
CATGCACTGGGTCCGCCAGGCTCCAGGCAAGGGGCTGGAGTGGGTGGCAG
TTATATGGTATGATGGAAGTAATAAATACTATGCAGACTCCGTGAAGGGC
CGATTCACCATCTCCAGAGACAATTCCAAGAACACGCTGTATCTGCAAAT
GAACAGCCTGAGAGCCGAGGACACGGCTGTGTATTACTGTGCGAGAGGGG
ACTTTTACTGGTTCGACCCCTGGGGCCAGGGAACCCTGGTCACCGTCTCC
TCA3'

SEQ ID NO: 50
Antibody 2B10.4 Amino acid sequence of heavy chain variable region
QVQLVESGGGVVQPGRSLRLSCAASGFTFSSYGMHWVRQAPGKGLEWVAV
IWYDGSNKYYADSVKGRFTISRDNSKNTLYLQMNSLRAEDTAVYYCARGD
FYWFDPWGQGTLVTVSS SEQ ID NO: 51
Antibody 2B10.4 Nucleotide sequence of light chain variable region
5'GACATCCAGATGACCCAGTCTCCATCCTCCCTGTCTGCATCTGTAGGA
GACAGAGTCACCATCACTTGCCGGGCAAGTCAGGGCATTAGAAATGATTT
AGGCTGGTATCAGCAGAAACCAGGGAAAGCCCCTAAGCGCCTGATCTATG
CTGCATCCAGTTTGCAAAGTGGGGTCCCATCAAGGTTCAGCGGCAGTGGA
TCTGGGACAGAATTCACTCTCACAATCAGCAGCCTGCAGCCTGAAGATTT
TGCAACTTATTACTGTCTACAGTATAATAGTTACCCGTGGACGTTCGGCC
AAGGGACCAAGGTGGAAATCAAA3'

SEQ ID NO: 52
Antibody 2B10.4 Amino acid sequence of light chain variable region
DIQMTQSPSSLSASVGDRVTITCRASQGIRNDLGWYQQKPGKAPKRLIYA
ASSLQSGVPSRFSGSGSGTEFTLTISSLQPEDFATYYCLQYNSYPWTFGQ
GTKVEIK SEQ ID NO: 53
Antibody 6B1 Nucleotide sequence of heavy chain variable region
5'CAGGTGCAGCTGGTGGAGTCTGGGGGAGGCGTGGTCCAGCCTGGGACG
TCCCTGAGACTCTCCTGTGCAGCGTCTGGATTCACCTTCAGTAGCTATGG
CATACACTGGGTCCGCCAGGCTCCAGGCAAGGGGCTGGAGTGGGTGGCAG
TTATATGGTATGATGGAAGTAATAAATTCCATGCAGACTCCGTGAAGGGC
CGATTCACCATCTCCAGAGACAATTCCAAGAACACGCTGTATCTGCAAAT
GAACAGCCTGAGAGCCGAGGACACGGCTGTGTATTACTGTGCGAGAGACC
CACTAGGATATTGTAGTAGTACCAGCTGCTCTTACTTTGACTACTGGGGC
CAGGGAACCCTGGTCACCGTCTCCTCA3'

SEQ ID NO: 54
Antibody 6B1 Amino acid sequence of heavy chain variable region
QVQLVESGGGVVQPGTSLRLSCAASGFTFSSYGIHWVRQAPGKGLEWVAV
IWYDGSNKFHADSVKGRFTISRDNSKNTLYLQMNSLRAEDTAVYYCARDP
LCYCSSTSCSYFDYWGQGTLVTVSS SEQ ID NO: 55
Antibody 6B1 Nucleotide sequence of light chain variable region
5'GACATCCAGATGACCCAGTCTCCATCTTCCGTGTCTGCATCTGTAGGA
GACAGAGTCACCATCACTTGTCGGGCGAGTCAGGGTATTAGCAACTGGTT
AGCCTGGTATCAGCAGAAACCAGGGAAAGCCCCTAAGCTCCTGATCTATG
CTGCATCCAGTTTGCAAAGTGGGGTCCCATCAAGGTTCAGCGGCAGTGGA
TCTGGGACAGATTTCACTCTCACCATCAGCAGCCTGCAGCCTGAAGATTT
TGCAACTTACTATTGTCAACAGGCTAACAATTTCCCGCTCACTTTCGGCG
GAGGGACCAAGGTGGAGATCAAA3'

SEQ ID NO: 56
Antibody 6B1 Amino acid sequence of light chain variable region
DIQMTQSPSSVSASVGDRVTITCRASQGISNWLAWYQQKPGKAPKLLIYA
ASSLQSGVSRFSGSGSGTDFTLTISSLQPEDFATYYCQQANNFPLTFGGG
TKVEIK SEQ ID NO: 57
Antibody 3C7 Nucleotide sequence of heavy chain variable region
5'CAGGTGCAGCTGGTGGAGTCTGGGGGAGGCGTGGTCCAGCCTGGGACG
TCCCTGAGACTCTCCTGTGCAGCGTCTGGATTCACCTTCAGTAGCTATGG
CATACACTGGGTCCGCCAGGCTCCAGGCAAGGGGCTGGAGTGGGTGGCAG
TTATATGGTATGATGGAAGTAATAAATTCTATGCAGACTCCGTGAAGGGC
CGATTCACTATCTCCAGAGACAATTCCAAGAACACGCTGTATCTGCAAAT
GAACAGCCTGAGAGCCGAGGACACGGCTGTGTATTACTGTGCGAGAGACC
CACTAGGATATTGTAGTAGTACCAGCTGCTCTTACTTTGACTACTGGGGC
CAGGGAACCCTGGTCACCGTCTCCTCA3'

SEQ ID NO: 58
Antibody 3C7 Amino acid sequence of heavy chain variable region
QVQLVESGGGVVQPGTSLRLSCAASGFTFSSYGIHWVRQAPGKGLEWVAV
IWYDGSNKFYADSVKGRFTLSRDNSKNTLYLQMNSLRAEDTAVYYCARDP
LGYCSSTSCSYFDYWGQGTLVTVSS SEQ ID NO: 59
Antibody 3C7 Nucleotide sequence of light chain variable region
5'GACATCCAGATGACCCAGTCTCCATCTTCCGTGTCTGCATCTGTAGGA
GACAGAGTCACCATCACTTGTCGGGCGAGTCAGGGTATTAGCAACTGGTT
AGCCTGGTATCAGCAGAAACCAGGGAAAGCCCCTAAGCTCCTGATCTATG
CTGCATCCAGTTTGCAAAGTGGGGTCCCATCACGGTTCAGCGGCAGTGGA
TCTGGGACAGATTTCACTCTCACCATCCGCAGCCTGCAGCCTGAAGATTT
TGCAACTTACTATTGTCAACAGGCTAACAATTTCCCGCTCACTTTCGGCG
GAGGGACCAAGGTGGAGATCAAA3'

SEQ ID NO: 60
Antibody 3C7 Amino acid sequence of light chain variable region
DIQMTQSPSSVSASVGDRVTITCRASQGISNWLAWYQQKPGKAPKLLIYA
ASSLQSGVPSRFSGSGSGTDFTLTIRSLQPEDFATYYCQQANNFPLTFGG
GTKVEIK SEQ ID NO: 61
Antibody 4D4.1 = 4D4.2 = 4D4.3 Nucleotide sequence of heavy chain variable region
5'CAGGTGCAGCTGGTGGAGTCTGGGGGAGGCGTGGTCCAGCCTGGGAGG
TCCCTGAGACTCTCCTGTGCAGCGTCTGGATTCACCTTCAGTAGCTATGG
CATGCACTGGGTCCGCCAGGCTCCAGGCAAGGGGCTGGAGTGGGTGGCAG
TTATATGGTATGATGGAAGTAATAAATACTATGCAGACTCCGTGAAGGGC
CGATTCACCATCTCCAGAGACAATTCCAAGAACACGCTGTATCTGCAAAT
GAACAGCCTGAGAGCCGAGGACACGGCTGTGTATTACTGTGCGAGAGGAG
GGGACGGTGAACGGTTTGACTACTGGGGCCAGGGAACCCTGGTCACCGTC
TCCTCA3'

SEQ ID NO: 62
Antibody 4D4.1 = 4D4.2 = 4D4.3 Amino acid sequence of heavy chain variable region
QVQLVESGGGVVQPGRSLRLSCAASGFTFSSYGMHWVRQAPGKGLEWVAV
IWYDGSNKYYADSVKGRFTISRDNSKNTLYLQMNSLRAEDTAVYYCARGG
DGERFDYWGQGTLVTVSS SEQ ID NO: 63
Antibody 4D4.1 = 4D4.2 = 4D4.3 Nucleotide sequence of light chain variable region
5'GATGTTGTGATGACTCAGTCTCCACTCTCCCTGCCCGTCACCCTTGGA
CAGCCGGCCTCCATCTCCTGCAGGTCTAGTCAAAGCCGCGTATACAGTGA
TGGAAACACCTTCTTGAATTGGTTTCAGCAGAGGCCAGGCCAATTTCCAA
GGCGCCTAATTTATAAGGTTTCCAACTGGGACTCTGGGGTCCCAGACAGA
TTCAGCGGCAGTGGGTCAGGCACTGATTTCACACTGAAAATCAGCAGGGT
GGAGGCTGAGGATGTTGGGGTTTATTACTGCATGCAAGGTACACACTGGC
CTCCTTATGTGCAGTTTTGGCCAGGGGACCAAGCTGGAGATCAA3'

SEQ ID NO: 64
Antibody 4D4.1 = 4D4.2 = 4D4.3 Amino acid sequence of light chain variable region
DVVMTQSPLSLPVTLGQPASISCRSSQSRVYSDGNTFLNWFQQRPGQFPR
RLIYKVSNWDSGVPDRFSGSGSGTDFTLKISRVEAEDVGVYYCMQGTHWP
PYVQFWPGDQAGDQ

ANTIBODY SEQUENCES

SEQ ID NO: 65
Antibody 5E10.1 = 5E10.2 Nucleotide sequence of heavy chain variable region
5'CAGGTGCAGCTGGTGGAGTCTGGGGGAGGCGTGGTCCAGCCTGGGAGG
TCCCTGAGACTCTCCTGTGCAGCGTCTGGATTCACCTTCAGAAGCTATGG
CATGCACTGGGTCCGCCAGGCTCCAGGCAAGGGGCTGGAGTGGGTGGCAG
TTTATAAGGCATGATGGAAGTAATAAATATAATGCAGACTCCGTGAAGGGC
CGATTCACCATCTCCAGAGACAATTCCAAGAACACGCTGTATCTGCAAAT
GAACAGTCTGAGAGCCGAGGACACGGCTGTGTATTACTGTGCGAGAGACC
CACTAGGATATTGTAGTAGTACCAGCTGCTCTTACTTTGACTACTGGGGC
CAGGGAACCCTGGTCACCGTCTCCTCA3'

SEQ ID NO: 66
Antibody 5E10.1 = 5E10.2 Amino acid sequence of heavy chain variable region
QVQLVESGGGVVQPGRSLRLSCAASGFTFRSYGMHWVRQAPGKGLEWVAV
IRHDGSNKYNADSVKGRFTISRDNSKNTLYLQMNSLRAEDTAVYYCARDP
LGYCSSTSCSYFDYWGQGTLVTVSS SEQ ID NO: 67
Antibody 5E10.1 = 5E10.2 Niicleotide sequence of light chain variable region
5'GACATCCAGATGACCCAGTCTCCATCTTCCGTGTCTGCATCTGTAGGA
GACAGAGTCACCATCACTTGTCGGGCGAGTCAGGGTATTAGCAGCTGGTT
AGCCTGGTATCAGCAGAAACCAGGGAAAGCCCCTAAGCTCCTGATCTATG
CTACATCCAGTTTGCAAAGTGGGGTCCCATCAAGGTTCAGCGGCAGTGGA
TCTGGGACAGATTTCACTCTCACCATCAGCAGCCTGCAGCCTGAAGATTT
TGCAACTTACTATTGTCAACAGGCTAACAATTTCCCGCTCACTTTCGGCG
GAGGGACCAAGGTGGAGATCAAA3'

SEQ ID NO: 68
Antibody 5E10.1 = 5E10.2 Amino acid sequence of light chain variable region
DIQMTQSPSSVSASVGDRVTITCRASQGISSWLAWYQQKPGKAPKLLIYA
TSSLQSGVPSRFSGSGSGTDFTLTISSLQPEDFATYYCQQANNFPLTFGG
GTKVEIK SEQ ID NO: 69
Antibody 3H12 Nucleotide sequence of heavy chain variable region
5'CAGGTGCAGCTGCAGGAGTCGGGCCCAGGACTGGTGAAGCCTTCGGAG
ACCCTGTCCCTCACCTGCACTGTCTCTGATGGCTCCATCAGTAGTTTCTA
CTGGAGCTGGATCCGGCAGCCCCCAGGGAAGGGACTGGAGTGGATTGGGT
ATATCTATTACAGTGGGAGCACCAACTACAACCCCTCCCTCAAGAGTCGA
GTCACCATATCAGTAGACACGTCCAAGAACCAGTTCTCCCTGAAGCTGAG
CTCTGTGACCGCTGCGGACACGGCCGTGTATTACTGTGCGAGAGATTACG
ATATCTTGACTGGTTATTCCAACTACTACGGTATGGACGTCTGGGGCCAA
GGGACCACGGTCACCGTCTCCTCA3'

SEQ ID NO: 70
Antibody 3H12 Amino acid sequence of heavy chain variable region
QVQLQESGPGLVKPSETLSLTCTVSDGSISSFYWSWIRQPPGKGLEWIGY
IYYSGSTNYNPSLKSRVTISVDTSKNQFSLKLSSVTAADTAVYYCARDYD
ILTGYSNYYGMDVWGQGTTVTVSS SEQ ID NO: 71
Antibody 3H12 Nucleotide sequence of light chain variable region
5'GACATCCAGATGACCCAGTCTCCATCCTCCCTGTCTGCATCTGTAGGA
GACAGAGTCACCATCACTTGCCGGGCAAGTCAGGGCATTAGAAATGATTT
AGGCTGGTATCAGCAGAAACCAGGGAAAGCCCCTAAGCGCCTGATCTATG
CTGCATCCAGTTTGCAAAGTGGGGTCCCATCAAGGTTCAGCGGCAGTGGA
TCTGGGACAGAATTCACTCTCACAATCAGCAGCCTGCAGCCTGAAGATTT
TGCAACTTATTACTGTCTGCAGCATAATAGTTACCCATTCACTTTCGGCC
CTGGGACCAAACTGGATATCAAA3'

SEQ ID NO: 72
Antibody 3H12 Amino acid sequence of light chain variable region
DIQMTQSPSSLSASVGDRVTITCRASQGIRNDLGWYQQKPGKAPKRLIYA
ASSLQSGVPSRFSGSGSGTEFTLTISSLQPEDFATYYCLQHNSYPFTFGP
GTKLDIK SEQ ID NO: 73
Antibody 1G3 Nucleotide sequence of heavy chain variable region
5'CAGGTGCAGCTGGTGCAGTCTGGGGCTGAGGTGAAGAAGCCTGGGGCC
TCAGTGAAGGTCTCCTGCAAGGCTTCTGGATACACCTTCACCGGCTACTA
TATGCACTGGGTGCGACAGGCCCCTGGACAAGGGCTTGAGTGGATGGGAT
GGATCAACCCTAACAGTGGTGGCACAAACTATGCACAGAAGTTTCAGGGC
AGGGTCACCATGACCAGGGACACGTCCATCAGCACAGCCTACATGGAGCT
GAGCAGGCTGAGATCTGACGACACGGCCGTGTTTTACTGTGCGGGTGGGA
CCTACTTGGACTACTGGGGCCAGGGAACCCTGGTCACCGTCTCCTCA3'

SEQ ID NO: 74
Antibody 1G3 Amino acid sequence of heavy chain variable region
QVQLVQSGAEVKKPGASVKVSCKASGYTFTGYYMHWVRQAPGQGLEWMGW
INPNSGGTNYAQKFQGRVTMTRDTSISTAYMELSRLRSDDTAVFYCAGGT
YLDYWGQGTLVTVSS SEQ ID NO: 75
Antibody 1G3 Nucleotide sequence of light chain variable region
5'GACATCCAGATGACCCAGTCTCCATCCTCCCTGTCTGCATCTGTAGGA
GACAGAGTCACCATCACTTGCCGGGCAAGTCAGGGCATTAGAAATGATTT
AGGCTGGTATCAGCAGAAACCAGGGAAAGCCCCTAAGCGCCTGATCTATG
CTGCATCCAGTTTGCAAAGTGGGGTCCCATCAAGGTTCAGCGGCAGTGGA
TCTGGGACAGAATTCACTCTCACAATCAGCAGCCTGCAGCCTGAAGATTT
TGCAACTTATTACTGTCTACAGTATAATAGTTACCCGATCACCTTCGGCC
AAGGGACACGACTGGAGATTAAA3'

SEQ ID NO: 76
Antibody 1G3 Amino acid sequence of light chain variable region
DIQMTQSPSSLSASVGDRVTITCRASQGIRNDLGWYQQKPGKAPKRLIYA
ASSLQSGVPSRFSGSGSGTEFTLTISSLQPEDFATYYCLQYNSYPITFGQ
GTRLEIK SEQ ID NO: 77
Antibody 5D1.1 Nucleotide sequence of heavy chain variable region
5'CAGGTTCAGCTGGTGCAGTCTGGAGCTGAGGTGAAGAAGCCTGGGGCC
TCAGTGAAGGTCTCCTGCAAGGCTTCTGGTTACACCTTTACCAGCTATGG
TATCAGCTGGGTGCGACAGGCCCCTGGACAAGGGCTTGAGTGGATGGGAT
GGATCGCTTATAATGGTAACACAAACTATGCACAGAAGCTCCAGGGC
AGAGGCACCATGACCACAGACACATCCACGAGCACAGCCTACATGGAGCT
GAGGAGCCTGAGATCTGACGACACGGCCGTGTATTACTGTGCGGTTGGGA
GGTACCTTGACTACTGGGGCCAGGGAACCCTGGTCACCGTCTCCTCA3'

SEQ ID NO: 78
Antibody 5D1.1 Amino acid sequence of heavy chain variable region
QVQLVQSGAEVKKPGASVKVSCKASGYTFTSYGISWVRQAPGQGLEWMGW
ISAYNGNTNYAQKLQGRGTMATDTSTSTAYMELSRLRSDDTAVYYCAVGR
YLDYWGQGTLVTVSS SEQ ID NO: 79
Antibody 5D1.1 Nucleotide sequence of light chain variable region
5'GACATCCAGATGACCCAGTCTCCATCCTCCCTGTCTGCATCTGTAGGA
GACAGAGTCACCATCACTTGCCGGGCAAGTCAGGACATTAGAAATGATTT
AGGCTGGTATCAGCAGAAACCAGGGAAAGCCCCTAAGCGCCTGATCTATG
CTGCATCCAGTTTGCAAAGTGGGGTCCCATCAAGGTTCAGCGGCAGTGGA
TCTGGGACAGAATTCACTCTCACAATCAGCAGCCTGCAGCCTGAAGATTT
TGCAACTTATTACTGTCTACAGTATAATAGTTACCCTCTCACTTTCGGCG
GAGGGACCAAGGTGGAGATCAAA3'

SEQ ID NO: 80
Antibody 5D1.1 Amino acid sequence of light chain variable region
DIQMTQSPSSLSASVGDRVTITCRASQDIRNDLGWYQQKPGKAPKRLIYA
ASSLQSGVPSRFSGSGSGTEFTLTISSLQPEDFATYYCLQYNSYPLTFGG
GTKVEIK -continued

| ANTIBODY SEOUENCES |
| --- |
| SEQ ID NO: 81<br>Antibody 5D1.3 Nucleotide sequence of heavy chain variable region<br>5'CAGGTGCAGCTGGTGGAGTCTGGGGGAGGCGTGGTCCAGCCTGGGAGG<br>TCCCTGAGACTCTCCTGTGCAGCGTCTGGATTCACCYFCAGTAGCTATGG<br>CATGCACTGGGTCCGCCAGGCTCCAGGCAAGGGGCTGGAGTGGGTGGCAG<br>TTATATGGTATGATGGAAGTAATAAATACTATGCAGACTCCGTGAAGGGC<br>CGATTCACCATCTCCAGAGACAATTCCAAGAACACGCTGTATCTGCAAAT<br>GAACAGCCTGAGAGCCGAGGACACGGCTGTGTATTACTGTGCGAGAGGGG<br>ACTTTTACTGGTTCGACCCCTGGGGCCAGGGAACCCTGGTCACCGTCTCC<br>TCA3' |
| SEQ ID NO: 82<br>Antibody 5D1.3 Amino acid sequence of heavy chain variable region<br>QVQLVESGGGVVQPGRSLRLSCAASGFTFSSYGMHWVRQAPGKGLEWVAV<br>IWYDGSNKYYADSVKGRFTISRDNSKNTLYLQMNSLRAEDTAVYYCARGD<br>FYWFDPWGQGTLVTVSS |
| SEQ ID NO: 83<br>Antibody 5D1.3 Nucleotide sequence of light chain variable region<br>5'GACATCCAGATGACCCAGTCTCCATCCTCCCTGTCTGCATCTGTAGGA<br>GACAGAGTCACCATCACTTGCCGGGCAAGTCAGGACATTAGAAATGATTT<br>AGGCTGGTATCAGCAGAAACCAGGGAAAGCCCCTAAGCGCCTGATCTATG<br>CTGCATCCAGTTTGCAAAGTGGGGTCCCATCAAGGTTCAGCGGCAGTGGA<br>TCTGGGACAGAATTCACTCTCACAATCAGCAGCCTGCAGCCTGAAGATTT<br>TGCAACTTATTACTGTCTACAGTATAATAGTTACCCTCTCACTTTCGGCG<br>GAGGGACCAAGGTGGAGATCAAA3' |
| SEQ ID NO: 84<br>Antibody 5D1.3 Amino acid sequence of light chain variable region<br>DIQMTQSPSSLSASVGDRVTITCRASQDIRNDLGWYQQKPGKAPKRLIYA<br>ASSLQSGVPSRFSGSGSGTEFTLTISSLQPEDFATYYCLQYNSYPLTFGG<br>GTKVEIK |
| SEQ ID NO: 80<br>Antibody 5D1.4 Nucleotide sequence of heavy chain variable region<br>5'CAGGTGCAGCTGGTGCAGTCTGGGGCTGAGGTGAAGAAGCCTGGGGCC<br>TCAGTGAAGGTCTCCTGCAAGGCTTCTGGATACACCTTCACCGGCTACTA<br>TATGCACTGGGTGCGACAGGCCCCTGGACAAGGGCTTGAGTGGATGGGAT<br>GGATCAACCCTAACAGTGGTGGCACAAACTATGCACAGAAGTTTCAGGGC<br>AGGGTCACCATGACCAGGGACACGTCCATCAGCACAGCCTACATGGAGCT<br>GAGCAGGCTGAGATCTGACGACACGGCCGTGTATTACTGTGCGAGAGGGC<br>CCCATACCTTTGGTTCGGGGAGTTACCCCTTTGACTACTGGGGCCAGGGA<br>ACCCTGGTCACCGTCTCCTCA3' |
| SEQ ID NO: 86<br>Antibody 5D1.4 Amino acid sequence of heavy chain variable region<br>QVQLVQSGAEVKKPGASVKVSCKASGYTFTGYYMHWVRQAPGQGLEWMGW<br>INPNSGGTNYAQKFQGRVTMTRDTSISTAYMELSRLRSDDTAVYYCARGP<br>HTFGSGSYPFDYWGQGTLVTVSS |
| SEQ ID NO: 87<br>Antibody 5D1.4 Nucleotide sequence of light chain variable region<br>5'GACATCCAGATGACCCAGTCTCCATCCTCCCTGTCTGCATCTGTAGGA<br>GACAGAGTCACCATCACTTGCCGGGCAAGTCAGGACATTAGAAATGATTT<br>AGGCTGGTATCAGCAGAAACCAGGGAAAGCCCCTAAGCGCCTGATCTATG<br>CTGCATCCAGTTTGCAAAGTGGGGTCCCATCAAGGTTCAGCGGCAGTGGA<br>TCTGGGACAGAATTCACTCTCACAATCAGCAGCCTGCAGCCTGAAGATTT<br>TGCAACTTATTACTGTCTACAGTATAATAGTTACCCTCTCACTTTCGGCG<br>GAGGGACCAAGGTGGAGATCAAA3' |
| SEQ ID NO: 88<br>Antibody 5D1.4 Amino acid sequence of light chain variable region<br>DIQMTQSPSSLSASVGDRVTITCRASQDIRNDLGWYQQKPGKAPKRLIYA<br>ASSLQSGVPSRFSGSGSGTEFTLTISSLQPEDFATYYCLQYNSYPLTFGG<br>GTKVEIK |

-continued

| ANTIBODY SEOUENCES |
| --- |
| SEQ ID NO: 89<br>Antibody 5D1.5 Nucleotide sequence of heavy chain variable region<br>5'CAGGTGCAGCTGGTGCAGTCTGGGGCTGAGGTGAAGAAGCCTGGGGCC<br>TCAGTGAAGGTCTCCTGCAAGGCTTCTGGATACACCTTCACCGGCTACTA<br>TATGCACTGGGTGCGACAGGCCCCCGGACAAGGGCTTGAGTGGATGGGAT<br>GGATCAACCCTAACAGTGGTGGCACAAACTATGCACAGAAGTTTCAGGGC<br>AGGGTCACCATGACCAGGGACACGTCCATCAGCACAGCCTACATGGAGCT<br>GAGCAGGCTGAGATCTGACGACACGGCCGTGTTTTACTGTGCGGGTGGGA<br>CCTACTTGGACTACTGGGGCCAGGGAACCCTGGTCACCGTCTCCTCA3' |
| SEQ ID NO: 90<br>Antibody 5D1.5 Amino acid sequence of heavy chain variable region<br>QVQLVQSGAEVKKPGASVKVSCKASGYTFTGYYMHWVRQAPGQGLEWMGW<br>INPNSGGTNYAQKFQGRVTMTRDTSISTAYMELSRLRSDDTAVFYCAGGT<br>YLDYWGQGTLVTVSS |
| SEQ ID NO: 91<br>Antibody 5D1.5 Nucleotide sequence of light chain variable region<br>5'GACATCCAGATGACCCAGTCTCCATCCTCCCTGTCTGCATCTGTAGGA<br>GACAGAGTCACCATCACTTGCCGGGCAAGTCAGGACATTAGAAATGATTT<br>AGGCTGGTATCAGCAGAAACCAGGGAAAGCCCCTAAGCGCCTGATCTATG<br>CTGCATCCAGTTTGCAAAGTGGGGTCCCATCAAGGTTCAGCGGCAGTGGA<br>TCTGGGACAGAATTCACTCTCACAATCAGCAGCCTGCAGCCTGAAGATTT<br>TGCAACTTATTACTGTCTACAGTATAATAGTTACCCTCTCACTTTCGGCG<br>GAGGGACCAAGGTGGAGATCAAA3' |
| SEQ ID NO: 92<br>Antibody 5D1.5 Amino acid sequence of light chain variable region<br>DIQMTQSPSSLSASVGDRVTITCRASQDIRNDLGWYQQKPGKAPKRLIYA<br>ASSLQSGVPSRFSGSGSGTEFTLTISSLQPEDFATYYCLQYNSYPLTFGG<br>GTKVEIK |
| SEQ ID NO: 93<br>SARS CoV S protein nucleotide sequence<br>atgtttattttcttattatttcttactctcactagtggtagtgaccttga<br>ccggtgcaccacttttgatgatgttcaagctcctaattacactcaacata<br>cttcatctatgaggggggtttactatcctgatgaaatttttagatcagac<br>actctttatttaactcaggatttatttcttccattttattctaatgttac<br>agggtttcatactattaatcatacgtttgacgaccctgtcatacctttta<br>aggatggtatttattttgctgccacagagaaatcaaatgttgtccgtggt<br>tgggttttggttctaccatgaacaacaagtcacagtcggtgattattat<br>taacaattctactaatgttgttatacgagcatgtaactttgaattgtgtg<br>acaaccctttctttgttgtttctaaacccatgggtacacggacacatact<br>atgatattcgataatgcatttaattgcactttcgagtacatatctgatgc<br>cttttcgcttgatgtttcagaaaagtcaggtaattttaaacacttacgag<br>agtttgtgtttaaaaataaagatgggtttctctatgtttataagggctat<br>caacctatagatgtagttcgtgatctaccttctggttttaacactttgaa<br>acctatttttaagttgcctcttggtattaacattacaaattttagagcca<br>ttcttacagccttttcacctgctcaagacacttggggcacgtcagctgca<br>gcctattttgttggctatttaaagccaactacatttatgctcaagtatga<br>tgaaaatggtacaatcacagatgctgttgattgttctcaaaatccacttg<br>ctgaactcaaatgctctgttaagagctttgagattgacaaaggaatttac<br>cagacctctaatttcagggttgttccctcaggagatgttgtgagattccc<br>taatattacaaacttgtgtccttttggagaggtttttaatgctactaaat<br>tcccttctgtctatgcatgggagaggaaaagaatttctaattgtgttgct<br>gattactctgtgctctacaactcaacatctttttcaacctttaagtgcta<br>tggcgtttctgccactaagttgaatgatctttgcttctccaatgtctatg<br>cagattcttttgtagtcaagggagatgatgtaagacaaatagcgccagga<br>caaactggtgttattgctgattataattataaattgccagatgatttcat<br>gggttgtgtccttgcttggaatactaggaacattgatgctacttcaactg<br>gtaattataattataaatataggtatcttagacatggcaagcttaggccc<br>tttgagagagacatatctaatgtgcctttctctcctgatggcaaaccttg<br>caccccacctgctcctaattgttattggccattaaatggttatggttttt<br>acaccactagtggcattggctaccaaccttacagagttgtagtactttct<br>tttgaacttttaaatgcaccggccacggtttgtggaccaaaattatccac<br>tgaccttattaagaaccagtgtgtcaattttaattttaatggactcactg<br>gtactggtgtgttaactccttcttcaaagagatttcaaccatttcaacaa<br>tttggccgtgatgtttctgatttcactgattccgttcgagatcctaaaac<br>atctgaaatattagacatttcaccttgctcttttggggtgtaagtgtaa<br>ttacacctggaacaaatgcttcatctgaagttgctgttctatatcaagat<br>gttaactgcactgatgtttctacattaattcatgcagaacaactcacacc<br>agcttggcgcatatattctactggaaacaatgtattccagactcaagcag |

-continued

ANTIBODY SEOUENCES gctgtcttataggagctgagcatgtcgacacttcttatgagtgcgacatt
cctattggagctggcatttgtgctagttaccatacagtttcttcattacg
tagtactagccaaaaatctattgtggcttatactatgtctttaggtgctg
atagttcaattgcttactctaataacaccattgctatacctactaacttt
tcaattagcattactacagaagtaatgcctgtttctatggctaaaacctc
cgtagattgtaatatgtacatctgcggagattctactgaatgtgctaatt
tgcttctccaatatggtagcttttgcagacaactaaatcgtgcactctca
ggtattgctgctgaacaggatcgcaacacacgtgaagtgttcgttcaagt
caaacaaatgtacaaaaccccaactttgaaagattttggtggttttaatt
tttcacaaatattacctgaccctctaaagccaactaagaggtcttttatt
gaggacttgctctttaataaggtgacactcgctgatgctggcttcatgaa
gcaatatggcgaatgcctaggtgatattaatgctagagatctcatttgtg
cgcagaagttcaatggacttacagtgttgccacctctgctcactgatgat
atgattgctgcctacactgctgctctagttagtggtactgccactgctgg
atggacatttggtgctggcgctgctcttcaaatacctttttgctatgcaaa
tggcatataggttcaatggcattggagttacccaaaatgttctctatgag
aaccaaaaacaaatcgccaaccaatttaacaaggcgattagtcaaattca
agaatcacttacaacaacatcaactgcattgggcaagctgcaagacgttg
ttaaccagaatgctcaagcattaaacacacttgttaaacaacttagctct
aattttggtgcaatttcaagtgtgctaaatgatatcctttcgcgacttga
taaagtcgaggcggaggtacaaattgacaggttaattacaggcagacttc
aaagccttcaaacctatgtaacacaacaactaatcagggctgctgaaatc
agggcttctgctaatcttgctgctactaaaatgtctgagtgtgttcttgg
acaatcaaaaagagttgacttttgcggaaagggctaccaccttatgtcct
tcccacaagcagccccgcatggtgttgtcttcctacatgtcacgtatgtg
ccatcccaggagaggaacttcaccacagcgccagcaatttgtcatgaagg
caaagcatacttccctcgtgaaggtgtttttgtgtttaatggcacttctt
ggtttattacacagaggaacttcttttctccacaaataattactacagac
aatacatttgtctcaggaaattgtgatgtcgttattggcatcattaacaa
cacagtttatgatcctctgcaacctgagcttgactcattcaaagaagagc
tggacaagtacttcaaaaatcatacatcaccagatgttgatcttggcgac
atttcaggcattaacgcttctgtcgtcaacattcaagaagaaattgaccg
cctcaatgaggtcgctaaaaatttaaatgaatcactcatcgaccttcaag
aattgggaaaatatgagcaatatattaaatggccttggtatgtttggctc
ggcttcattgctggactaattgccatcgtcatggttacaatcttgctttg
ttgcatgactagttgttgcagttgcctcaagggtgcatgctcttgtggtt
cttgctgcaagtttgatgaggatgactctgagccagttctcaagggtgtc
aaattacattacacataa

SEQ ID NO: 94

SARS CoV S Protein amino acid sequence
MFIFLLFLTLTSGSDLDRCTTFDDVQAPNYTQHTSSMRGVYYPDEIFRSD
TLYLTQDLFLPFYSNVTGFHTINHTFDDPVIPFKDGIYFAATEKSNVVRG
WVFGSTMNNKSQSVIIINNSTNVVIRACNFELCDNPFFVVSKPMGTRTHT
MIFDNAFNCTFEYISDAFSLDVSEKSGNFKHLREFVFKNKDGFLYVYKGY
QPIDVVRDLPSGFNTLKPIFKLPLGINITNFRAILTAFSPAQDTWGTSAA
AYFVGYLKPTTFMLKYDENGTITDAVDCSQNPLAELKCSVKSFEIDKGIY
QTSNFRVVPSGDVVRFPNITNLCPFGEVFNATKFPSVYAWERKRISNCVA
DYSVLYNSTSFSTFKCYGVSATKLNDLCFSNVYADSFVVKGDDVRQIAPG
QTGVIADYNYKLPDDFMGCVLAWNTRNIDATSTGNYNYKYRYLRHGKLRP
FERDISNVPFSPDGKPCTPPAPNCYWPLNGYGFYTTSGIGYQPYRVVVLS
FELLNAPATVCGPKLSTDLIKNQCVNFNFNGLTGTGVLTPSSKRFQPFQQ
FGRDVSDFTDSVRDPKTSEILDISPCSFGGVSVITPGTNASSEVAVLYQD
VNCTDVSTLIHAEQLTPAWRIYSTGNNVFQTQAGCLIGAEHVDTSYECDI
PIGAGICASYHTVSSLRSTSQKSIVAYTMSLGADSSIAYSNNTIAIPTNF
SISITTEVMPVSMAKTSVDCNMYICGDSTECANLLLQYGSFCRQLNRALS
GIAAEQDRNTREVFVQVKQMYKTPTLKDFGGFNFSQILPDPLKPTKRSFI
EDLLFNKVTLADAGFMKQYGECLGDINARDLICAQKFNGLTVLPPLLTDD
MIAAYTAALVSGTATAGWTFGAGAALQIPFAMQMAYRFNGIGVTQNVLYE
NQKQIANQFNKAISQIQESLTTTSTALGKLQDVVNQNAQALNTLVKQLSS
NFGAISSVLNDILSRLDKVEAEVQIDRLITGRLQSLQTYVTQQLIRAAEI
RASANLAATKMSECVLGQSKRVDFCGKGYHLMSFPQAAPHGVVFLHVTYV
PSQERNFTTAPAICHEGKAYFPREGVFVFNGTSWFITQRNFFSPQIITTD
NTFVSGNCDVVIGIINNTVYDPLQPELDSFKEELDKYFKNHTSPDVDLGD
ISGINASVVNIQEEIDRLNEVAKNLNESLIDLQELGKYEQYIKWPWYVWL
GFIAGLIAIVMVTILLCCMTSCCSCLKGACSCGSCCKFDEDDSEPVLKGV
KLHYT

SEQ ID NO: 95

SARS CoV S protein 12-261 amino acid sequence
SGSDLDRCTTFDDVQAPNYTQHTSSMRGVYYPDEIFRSDTLYLTQDLFLP
FYSNVTGFHTINHTFDDPVIPFKDGIYFAATEKSNVVRGWVFGSTMNNKS
QSVIIINNSTNVVIRACNFELCDNPFFVVSKPMGTRTHTMIFDNAFNCTF
EYISDAFSLDVSEKSGNFKHLREFVFKNKDGFLYVYKGYQPIDVVRDLPS
GFNTLKPIFKLPLGINITNFRAILTAFSPAQDTWGTSAAAYFVGYLKPTT

SEQ ID NO: 96

SARS CoV S Protein 318-510 amino acid sequence
NITNLCPFGEVFNATKFPSVYAWERKRISNCVADYSVLYNSTSFSTFKCY
GVSATKLNDLCFSNVYADSFVVKGDDVRQIAPGQTGVIADYNYKLPDDFM
GCVLAWNTRNIDATSTGNYNYKYRYLRHGKLRPFERDISNVPFSPDGKPC
TPPAPNCYWPLNGYGFYTTSGIGYQPYRVVVLSFELLNAPATV

SEQ ID NO: 97

SARS CoV S Protein 15-680 amino acid sequence
DLDRCTTFDDVQAPNYTQHTSSMRGVYYPDEIFRSDTLYLTQDLFLPFYS
NVTGFHTINHTFDDPVIPFKDGIYFAATEKSNVVRGWVFGSTMNNKSQSV
IIINNSTNVVIRACNFELCDNPFFVVSKPMGTRTHTMIFDNAFNCTFEYI
SDAFSLDVSEKSGNFKHLREFVFKNKDGFLYVYKGYQPIDVVRDLPSGFN
TLKYIFKLPLGINITNFRAILTAFSPAQDTWGTSAAAYFVGYLKPTTFML
KYDENGTITDAVDCSQNPLAELKCSVKSFEIDKGIYQTSNFRVVPSGDVV
RFPNITNLCPFGEVFNATKFPSVYAWERKRISNCVADYSVLYNSTSFSTF
KCYGVSATKLNDLCFSNVYADSFVVKGDDVRQIAPGQTGVIADYNYKLPD
DFMGCVLAWNTRNIDATSTGNYNYKYRYLRHGKLRPFERDISNVPFSPDG
KPCTPPAPNCYWPLNGYGFYTTSGIGYQPYRVVVLSFELLNAPATVCGPK
LSTDLIKNQCVNFNFNGLTGTGVLTPSSKRFQPFQQFGRDVSDFTDSVRD
PKTSEILDISPCSFGGVSVITPGTNASSEVAVLYQDVNCTDVSTLIHAEQ
LTPAWRIYSTGNNVFQTQAGCLIGAEHVDTSYECDIPIGAGICASYHTVS
SLRSTSQKSIVAYTMS

SEQ ID NO: 98

SARS CoV S Protein 681-1255 amino acid sequence
LGADSSIAYSNNTIAIPTNFSISITTEVMPVSMAKTSVDCNMYICGDSTE
CANLLLQYGSFCRQLNRALSGIAAEQDRNTREVFVQVKQMYKTPTLKDFG
GFNFSQILPDPLKPTKRSFIEDLLFNKVTLADAGFMKQYGECLGDINARD
LICAQKFNGLTVLPPLLTDDMIAAYTAALVSGTATAGWTFGAGAALQIPF
AMQMAYRFNGIGVTQNVLYENQKQIANQFNKAISQIQESLTTTSTALGKL
QDVVNQNAQALNTLVKQLSSNFGAISSVLNDILSRLDKVEAEVQIDRLIT
GRLQSLQTYVTQQLIRAAEIRASANLAATKMSECVLGQSKRVDFCGKGYH
LMSFPQAAPHGVVFLHVTYVPSQERNFTTAPAICHEGKAYFPREGVFVFN
GTSWFITQRNFFSPQIITTDNTFVSGNCDVVIGIINNTVYDPLQPELDSF
KEELDKYFKNHTSPDVDLGDISGINASVVNIQEEIDRLNEVAKNLNESLI
DLQELGKYEQYIKWPWYVWLGFIAGLIAIVMVTILLCCMTSCCSCLKGAC
SCGSCCKFDEDDSEPVLKGVKLHYT

What is claimed is:

1. An isolated human monoclonal antibody, or antigen-binding portion thereof, that specifically binds SARS-CoV S protein, comprising light chain variable (VL) and heavy chain variable (VH) domains that are at least 99% identical in amino acid sequence to the VL domain shown as SEQ ID NO:60 and the VH domain shown as SEQ ID NO:58, respectively, of the monoclonal antibody 3C7.

2. An isolated human monoclonal antibody, or antigen-binding portion thereof, that specifically binds SARS-CoV S protein, comprising:
   (a) a heavy chain variable domain amino acid sequence that comprises the amino acid sequence of SEQ ID NO:58
   (b) a light chain variable domain amino acid sequence that comprises the amino acid sequence of SEQ ID NO:60; or
   (c) a heavy chain variable domain of (a) and a light chain variable domain of (b).

3. An isolated monoclonal antibody, or antigen-binding portion thereof, that specifically binds human SARS-CoV S protein, comprising:
   (a) a heavy chain variable domain that comprises the amino acid sequences of the heavy chain CDR1, CDR2 and CDR3 of the antibody 3C7 shown in SEQ ID NO:58; and
   (b) a light chain variable domain that comprises the amino acid sequences of the light chain CDR1, CDR2 and CDR3 of the antibody 3C7 shown in SEQ ID NO:60.

4. An isolated monoclonal antibody that specifically binds SARS-CoV S protein comprising:
   (a) a heavy chain of the antibody 3C7 that comprises the amino acid sequence of SEQ ID NO:58;
   (b) a light chain of the antibody 3C7 that comprises the amino acid sequence of SEQ ID NO:60; or
   (c) a heavy chain of (a) and a light chain of (b).

5. A composition comprising at least one isolated monoclonal antibody, or antigen-binding portion thereof, of claim 1, 2, 3 or 4, and further comprising a pharmaceutically-acceptable carrier.

6. The composition according to claim 5, further comprising at least one additional therapeutic agent selected from the group consisting of:
   (a) one or more antibodies or an antigen binding portion thereof, wherein said antibody is from the group consisting of: 1B5, 1G3, 2E8.1, 2E8.2, 2B10.1, 2B10.2, 2B10.3, 2B10.4, 3A7, 3C7, 3F3, 3H12, 4E2, 4A10, 4D4.1, 4D4.2, 4D4.3, 4G2, 5E1.1.1, 5E1.1.2, 5E1.2, 5E1.3, 5E10.1, 5E10.2, 5E4, 5A5, 5A7, 5C12.1, 5C12.2, 5D1.1, 5D1.2, 5D1.3, 5D1.4, 5D1.5, 5D3, 5D6, 6B1, 6B5, 6B8 , 6C1, and 6C2;
   (b) one or more antibodies that specifically bind SARS-CoV S protein of a different SARS-CoV strain;
   (c) one or more SARS-CoV neutralizing antibodies, wherein said antibodies do not bind SARS-CoV S protein;
   (d) one or more agents that bind a SARS-CoV S protein receptor and blocks binding of S protein to the receptor; and
   (e) one or more anti-viral agents.

7. The composition according to claim 5, further comprising at least two antibodies that specifically bind to different regions of human SARS-CoV S protein selected from the group consisting of: amino acid residues 1-1255 (SEQ ID NO: 94), a region that is at least 80% identical to SEQ ID NO:94, amino acid residues 12-261 (SEQ ID NO: 95), a region that is at least 80% identical to SEQ ID NO:95, amino acid residues 318-510(SEQ ID NO:96), a region that is at least 80% identical to SEQ ID NO:96, amino acid residues 15-680(SEQ ID NO:97), and a region that is at least 80% identical to SEQ ID NO:97.

8. An isolated cell line that produces the antibody, or the antigen-binding portion thereof, of claims 1, 2, 3 or 4.

9. A method for decreasing S protein-mediated SARS-CoV binding to cells, the method comprising the step of contacting the S protein with the composition of claim 5.

10. The method according to claim 9, wherein said cells express angiotensin converting enzyme 2 (Ace2).

11. A method for decreasing a SARS-CoV S protein-mediated activity, comprising contacting the S protein with the composition of claim 5.

12. The method according to claim 11, wherein the SARS-CoV S protein-mediated activity is selected from: viral attachment to a cell, fusing of viral membrane with a cell, or combinations thereof.

13. The method according to claim 11, wherein the method is performed in a subject.

14. The antigen-binding portion according to any of claims 1-3 or 4, wherein the antigen-binding portion is selected from the group consisting of Fab, Fab', $F(ab')_2$, Fd, Fv, dAb, single-chain antibodies (scFv), chimeric antibodies, and diabodies.

15. The isolated human monoclonal antibody or antigen-binding portion according to any of claims 1-3 or 4, wherein said antibody or antigen-binding portion is labeled.

* * * * *

UNITED STATES PATENT AND TRADEMARK OFFICE
CERTIFICATE OF CORRECTION

PATENT NO. : 7,728,110 B2 Page 1 of 1
APPLICATION NO. : 11/805129
DATED : June 1, 2010
INVENTOR(S) : John Babcook et al.

It is certified that error appears in the above-identified patent and that said Letters Patent is hereby corrected as shown below:

In The Claims

In Claim 6, column 161, line 63, please delete "3C7".

Signed and Sealed this

Ninth Day of November, 2010

David J. Kappos
*Director of the United States Patent and Trademark Office*